(12) United States Patent
Yu

(10) Patent No.: US 8,680,129 B2
(45) Date of Patent: Mar. 25, 2014

(54) COMPOUNDS, COMPOSITION, METHODS, TARGETS FOR CANCER THERAPY

(76) Inventor: Ming Yu, Los Angeles, CA (US)

( * ) Notice: Subject to any disclaimer, the term of this patent is extended or adjusted under 35 U.S.C. 154(b) by 758 days.

(21) Appl. No.: 12/667,687

(22) Filed: Jan. 4, 2010

(65) Prior Publication Data

US 2011/0142815 A1 Jun. 16, 2011

Related U.S. Application Data

(63) Continuation of application No. PCT/US2008/069106, filed on Jul. 2, 2008.

(60) Provisional application No. 61/156,507, filed on Mar. 1, 2009.

(51) Int. Cl.
*A01N 43/64* (2006.01)
*A61K 31/41* (2006.01)

(52) U.S. Cl.
USPC .......................... 514/381; 514/183

(58) Field of Classification Search
None
See application file for complete search history.

(56) References Cited

U.S. PATENT DOCUMENTS

| 2004/0059100 | A1* | 3/2004 | Buchholz et al. | 536/8 |
| 2005/0176086 | A1* | 8/2005 | Yonehara et al. | 435/25 |
| 2005/0257291 | A1* | 11/2005 | Mizutani et al. | 800/284 |
| 2008/0194019 | A1* | 8/2008 | Cantley et al. | 435/375 |

FOREIGN PATENT DOCUMENTS

WO PCT/JP1997/001324 10/1997
WO PCT/JP2004/009953 7/2004

OTHER PUBLICATIONS

Stoetzer et al., Modulation of apoptosis by mitochondrial uncouplers: apoptosis-delaying features despite intrinsic cytotoxicity, 2002, Biochemical Pharmacology, vol. 63, pp. 471-483.*
Wang et al., Induction of Apoptosis by Apigenin and Related Flavonoids Through Cytochrome c Release and Activation of Caspase-9 and Caspase-3 in Leukemia HL-60 cells, 1999, Eur. J. Cancer, vol. 35, No. 10, pp. 1517-1525. Submitted by Applicant on Jul. 13, 2012.*
Patries M. herst and Michael V. berridge, Plasma membrane Electron Trans[ort: A new Target for Cancer Drug Development, Current Molecular Medicine, 2006, 6:895-904.
08781309.3-2107/21, Dec. 9, 2001, EPO, Search report only, dated 2011.

* cited by examiner

*Primary Examiner* — Jeffrey S. Lundgren
*Assistant Examiner* — Meghan Finn

(57) ABSTRACT

This invention describes methods and pharmaceutical compositions for combinational cancer treatments that are capable of inducing JNK phosphorylation and induce programmed cell death. It also identified genes as target for anti-cancer drug development and enhancement of the chemotherapeutic drug effect for the treatment of cancer. This invention points to a novel method and principle for a new avenue of developing more efficient and low or non cytotoxic cancer treatment.

1 Claim, 18 Drawing Sheets

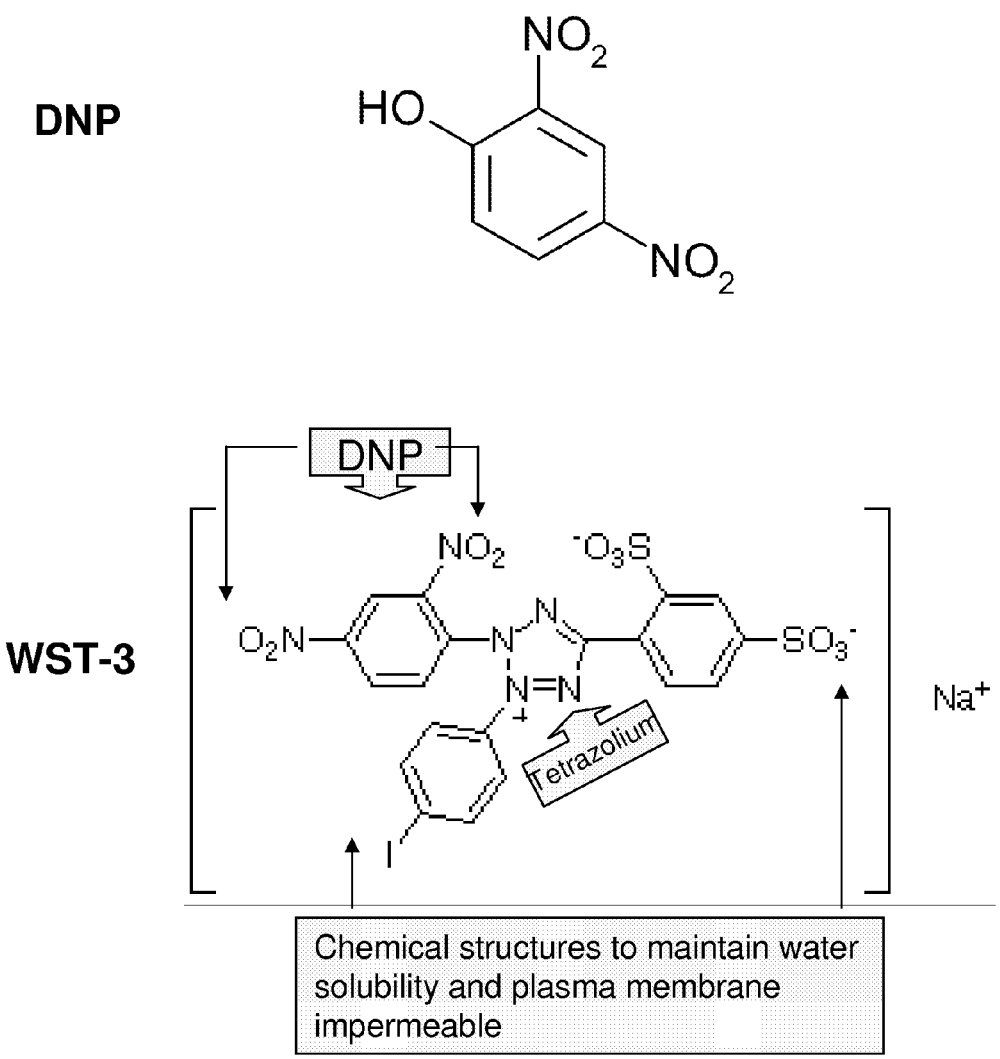
Fig 1 A Chemical Structure of 2,4-Dinitrophenol (DNP) and WST-3

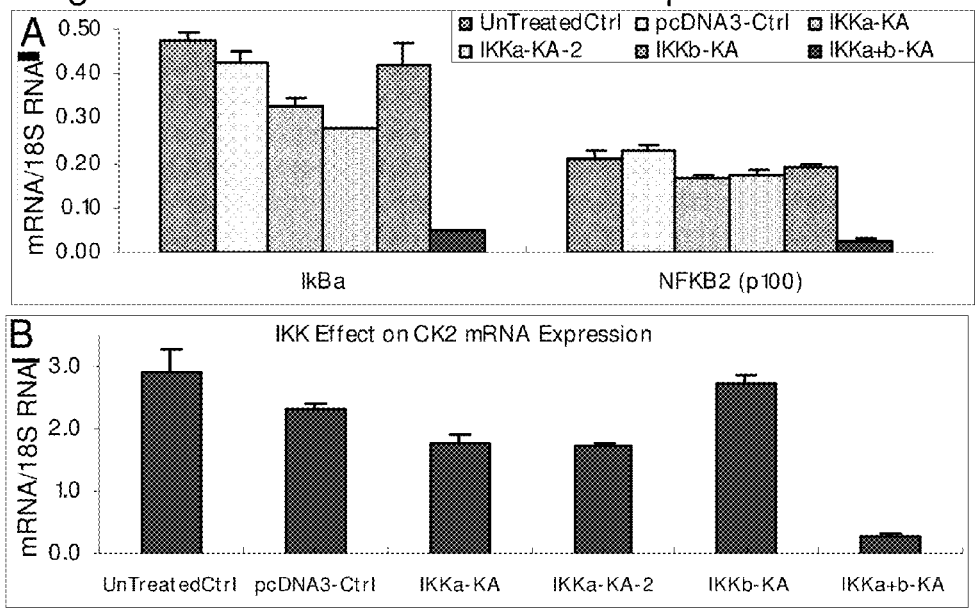
Fig 2 NF-κB Down Stream Gene Expression Levels
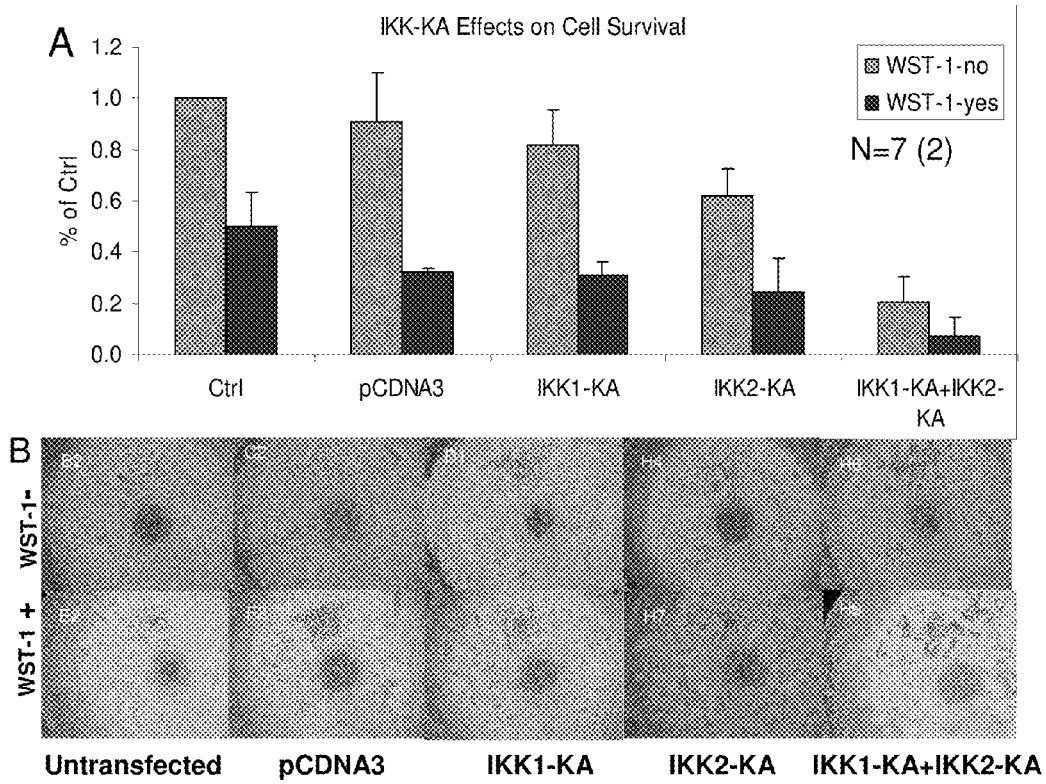
Fig 3 Combinational Effect of IKK-KA Transfection and WST-1 Treatment

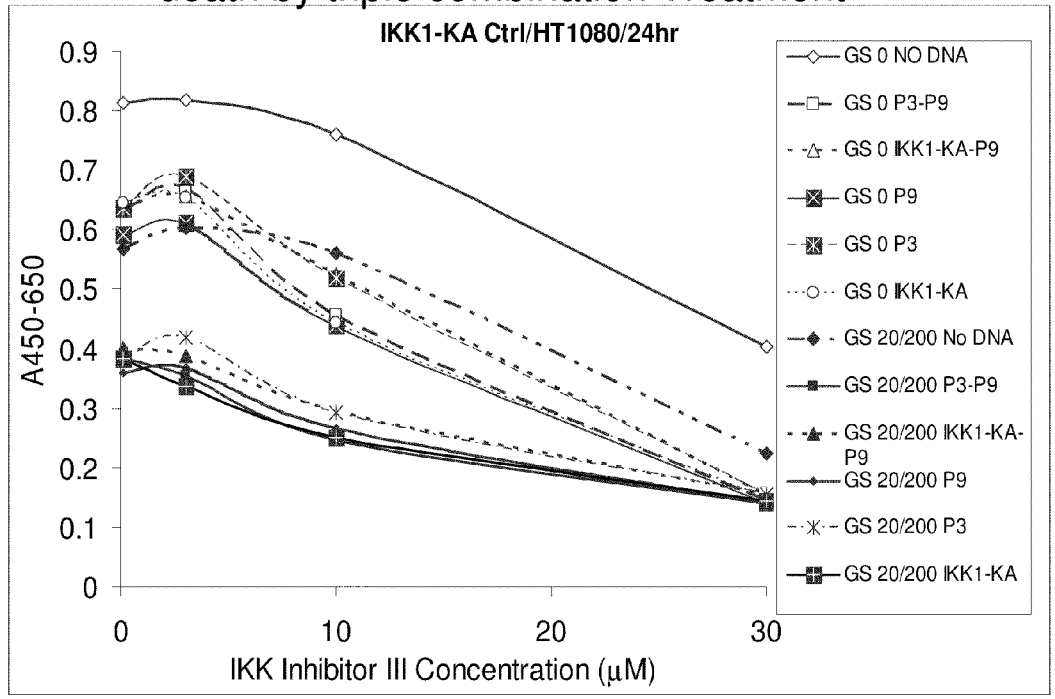
Fig 4 WST-1 promotes HT1080 Human Sarcoma cell death by triple combination Treatment
GS=WST-1, P9=Puc19, P3=pCDNA3
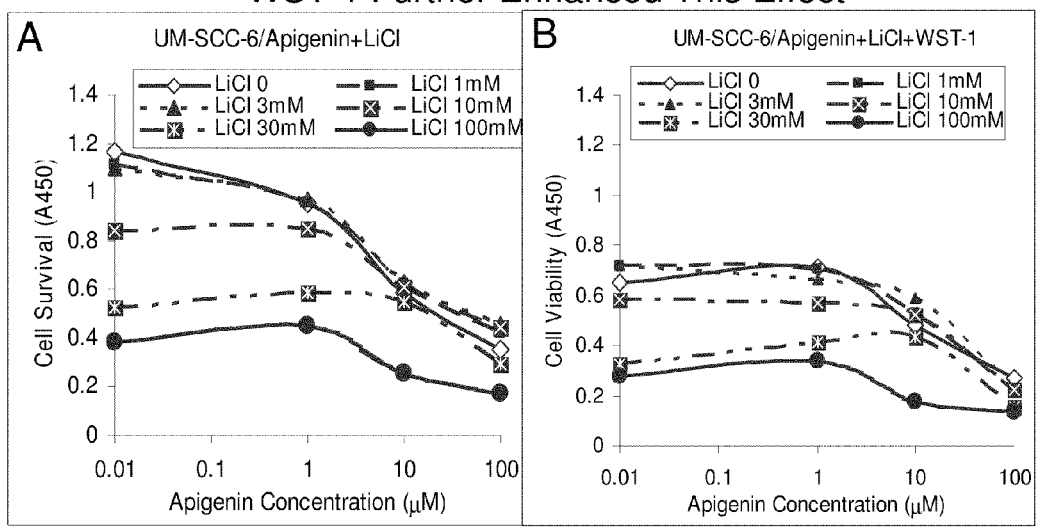
Fig 5 LiCl + Apigenin Synergized SCC-6 Cell Death, WST-1 Further Enhanced This Effect

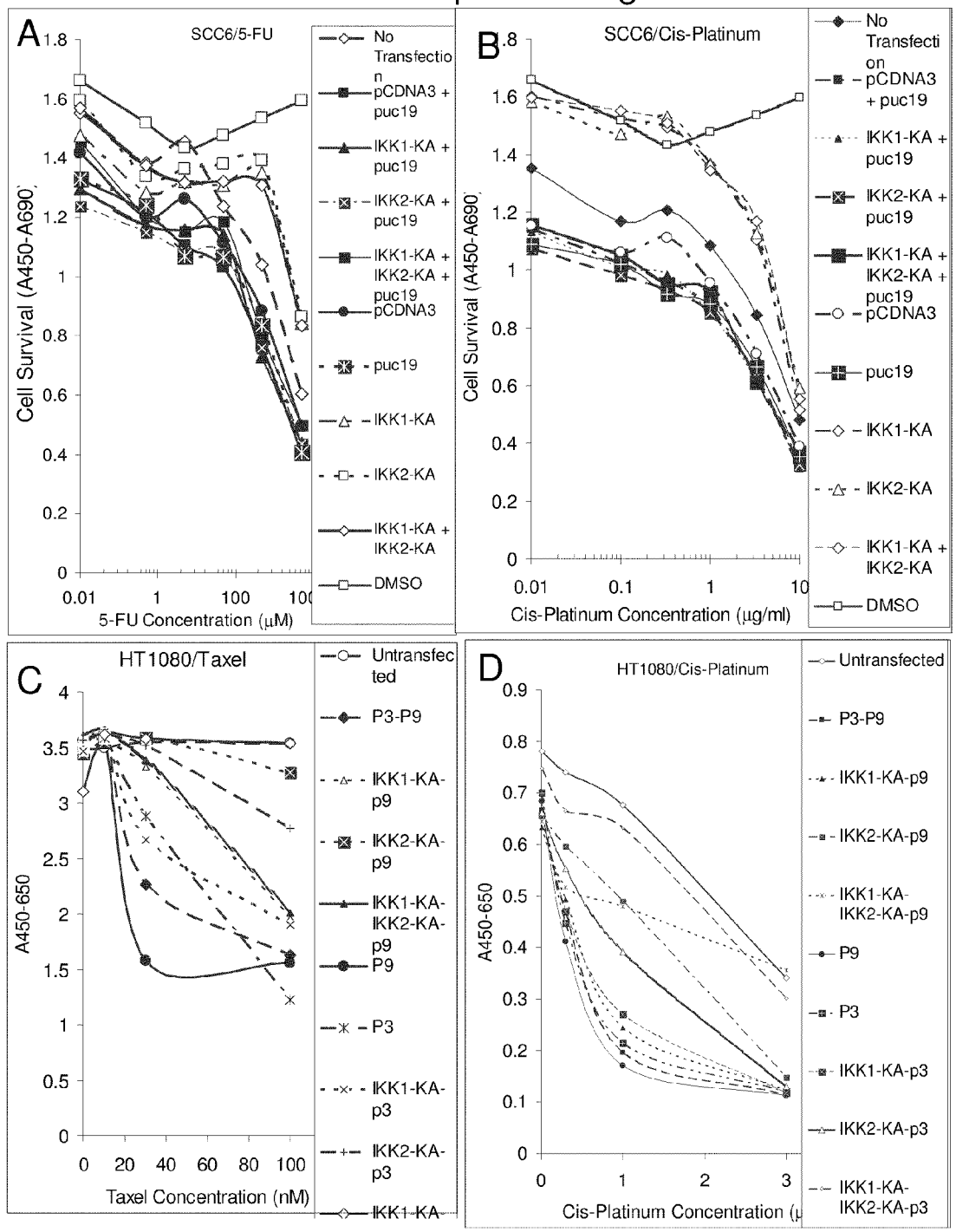
Fig 6 pUC19 DNA transfection synergize chemotherapeutic drug effect

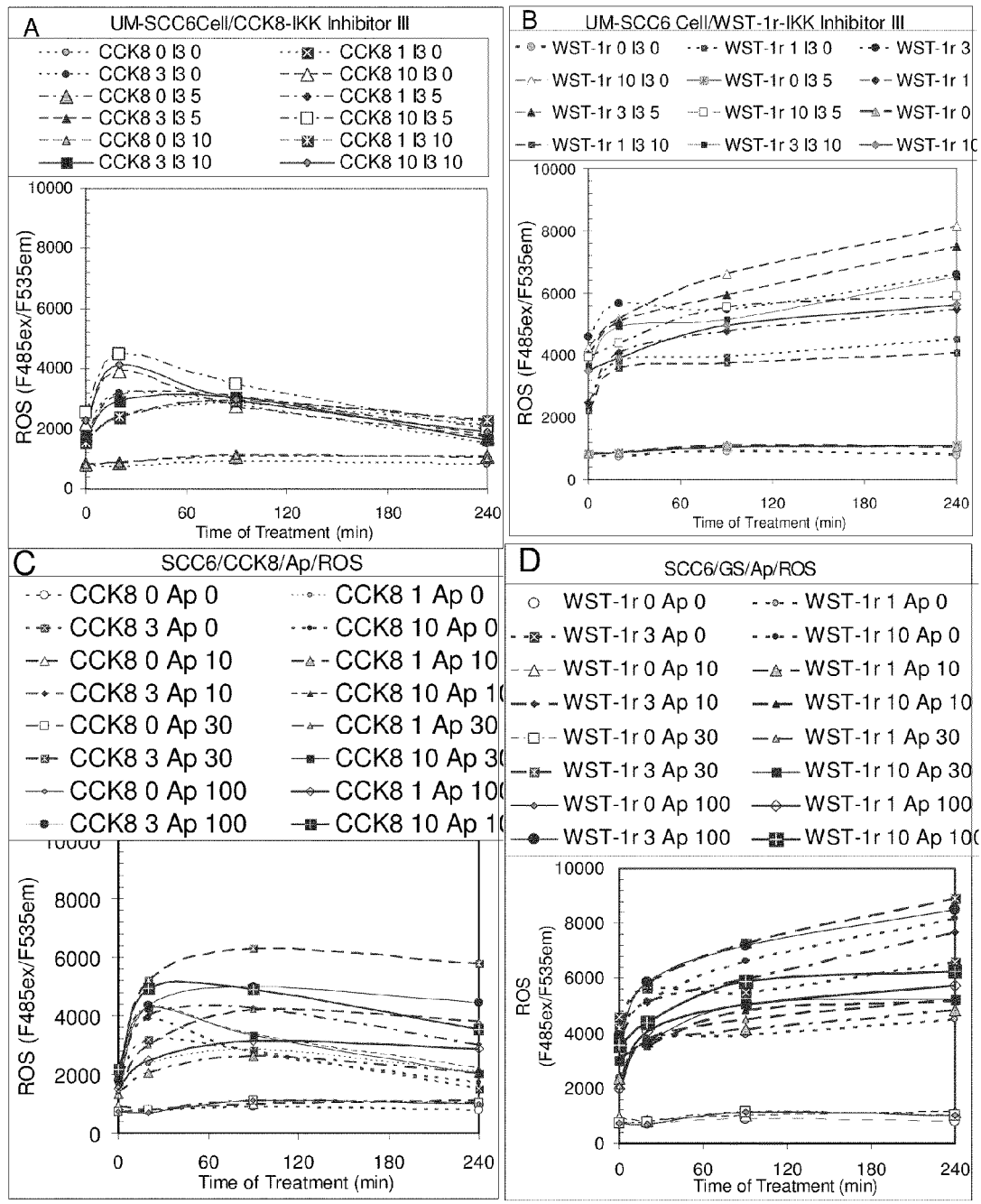
Fig7. Reactive Oxygen Species Generation from Combination Treatment
Ap=Apigenin   I3=IKK Inhibitor III

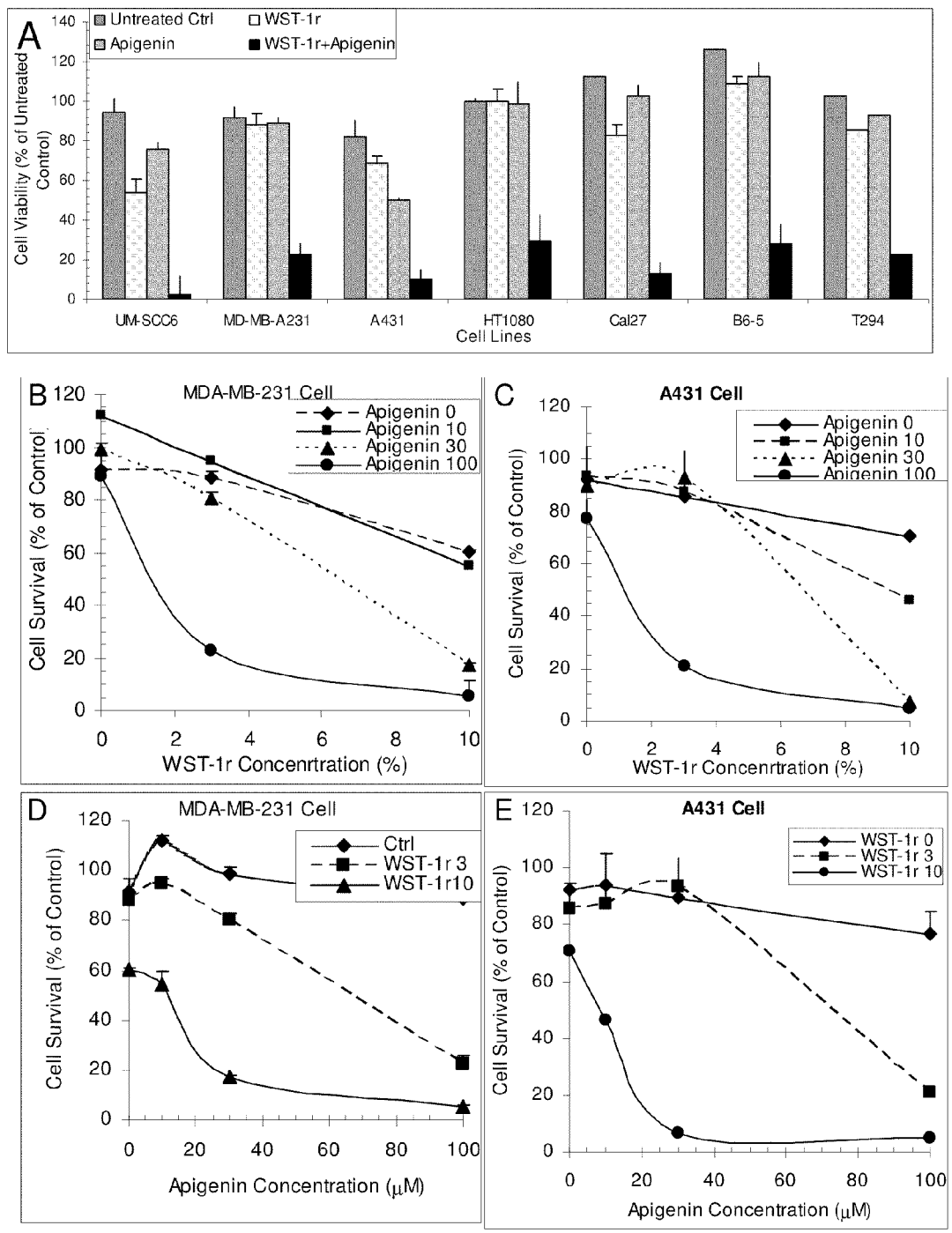
Fig 8. Combination Treatment with Apigenin and WST-1r Induces Cancer Cell Death

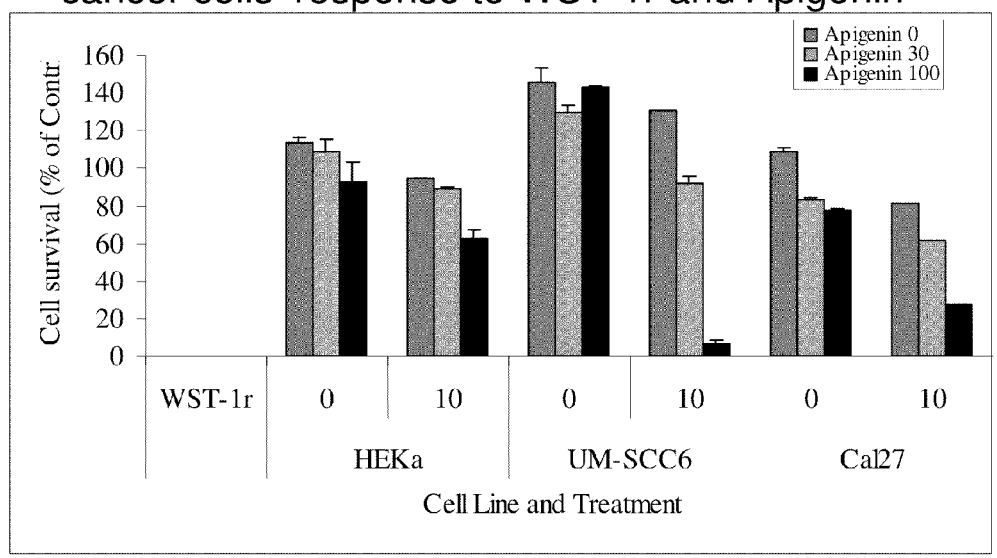
Fig 9. Comparison of Cancer cells and non cancer cells' response to WST-1r and Apigenin

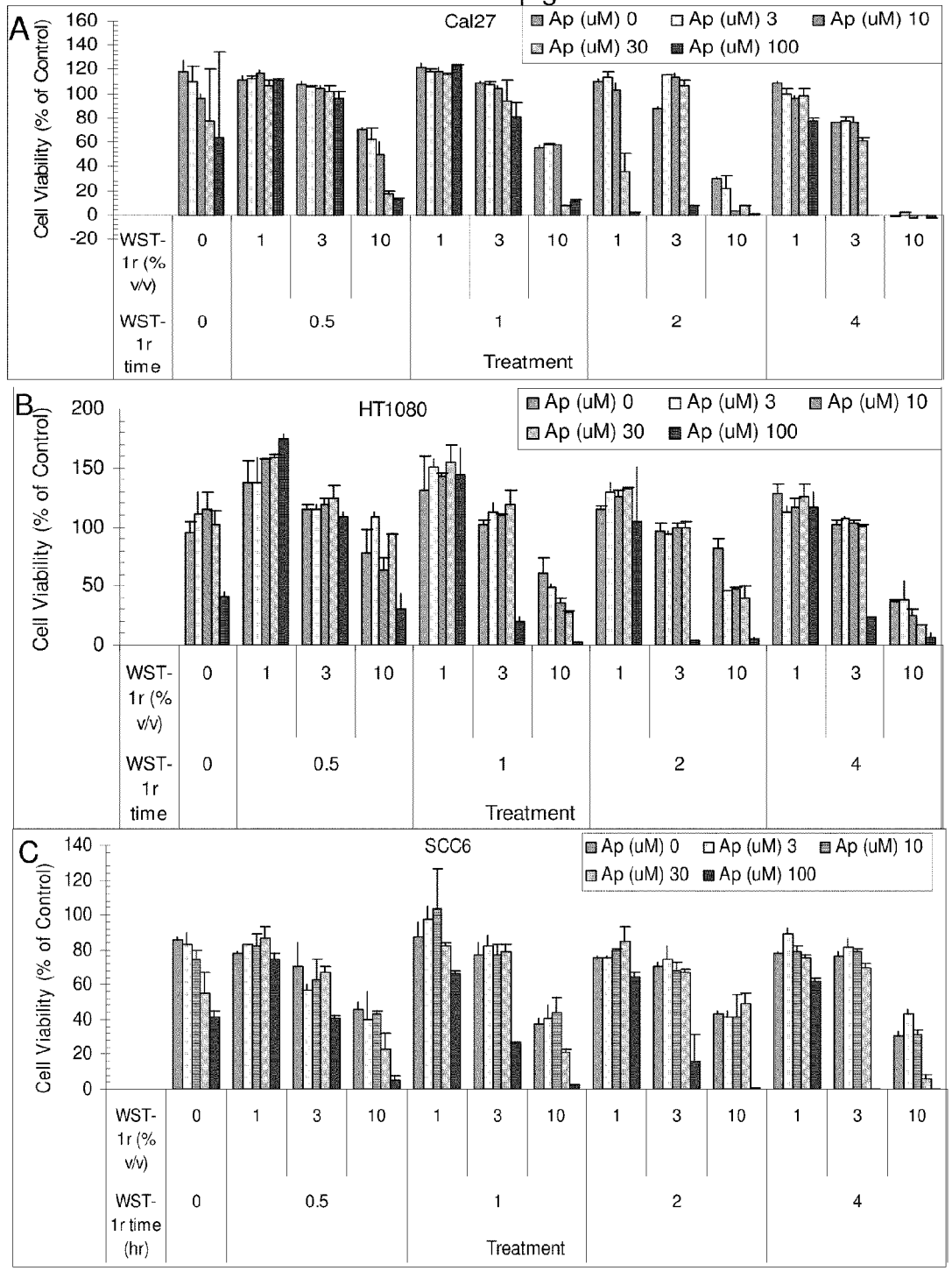
Fig 10 Time course and Dose Response of WST-1r and Dose-Response of Apigenin (Ap) Involved in the Combination Treatment of WST-1r with Apigenin Fig 11.
Effect of IKK Inhibitor III-WST-1r Combination Treatment
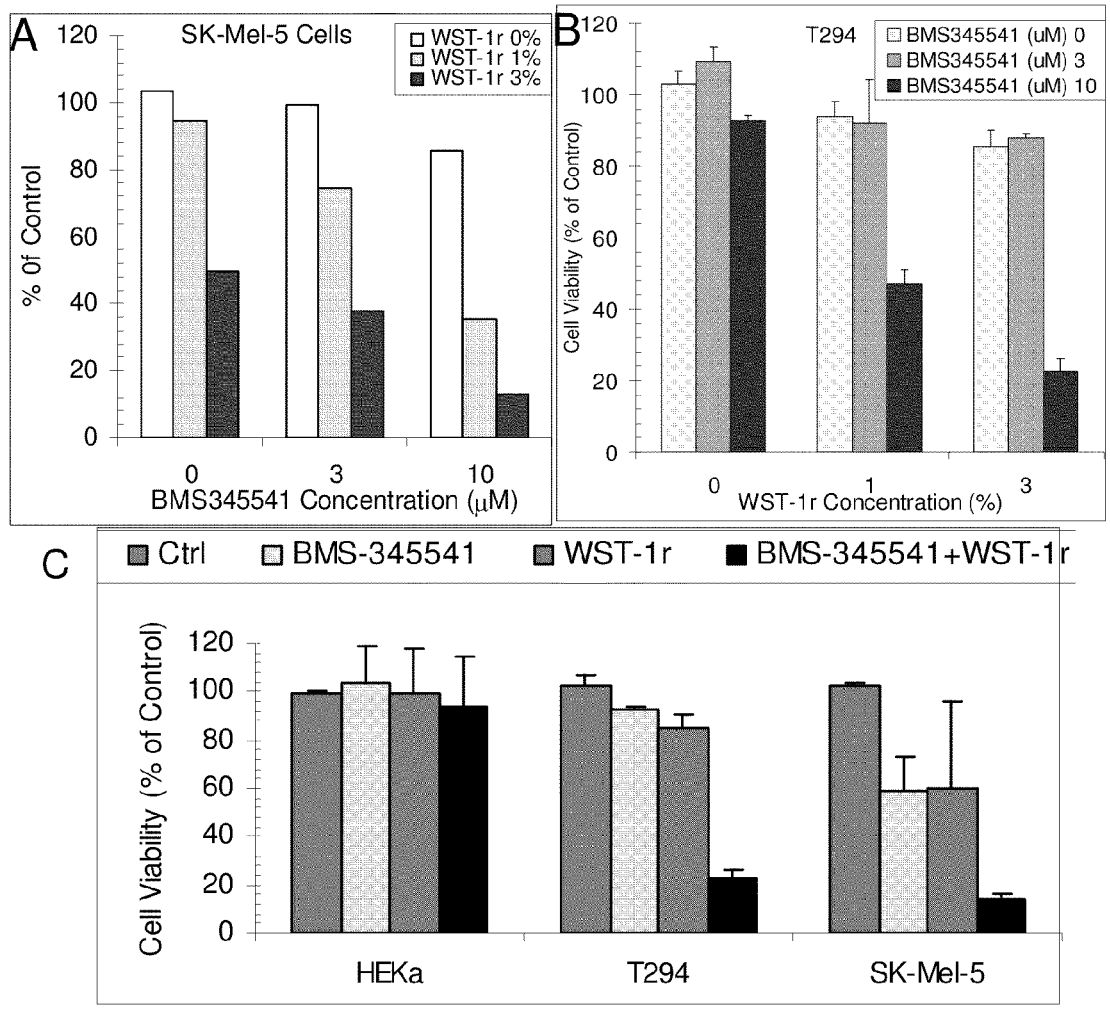
Fig 12. Treatment order of BMS345541 and WST-1r
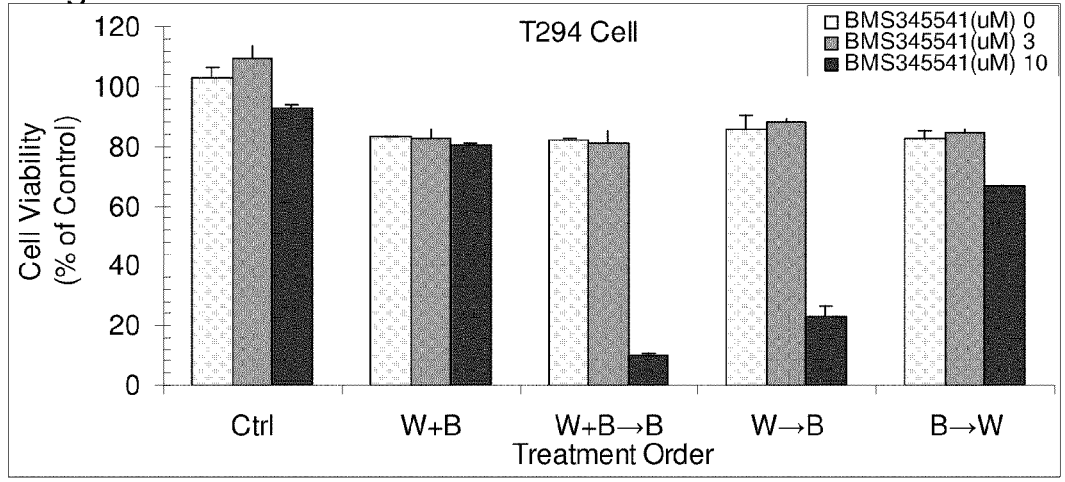

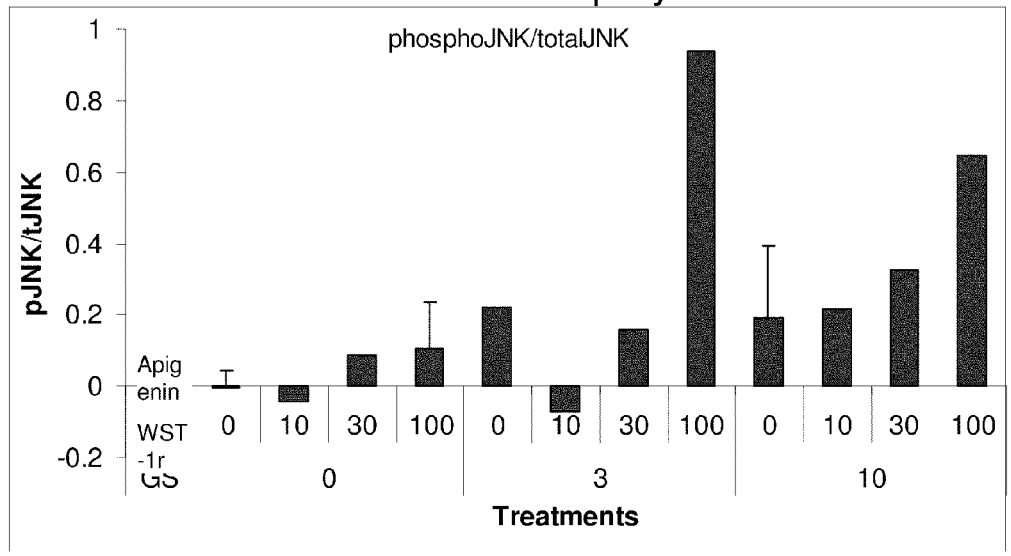
Fig 13 WST-1r and Apigenin combination treatment induced JNK Phosphrylation
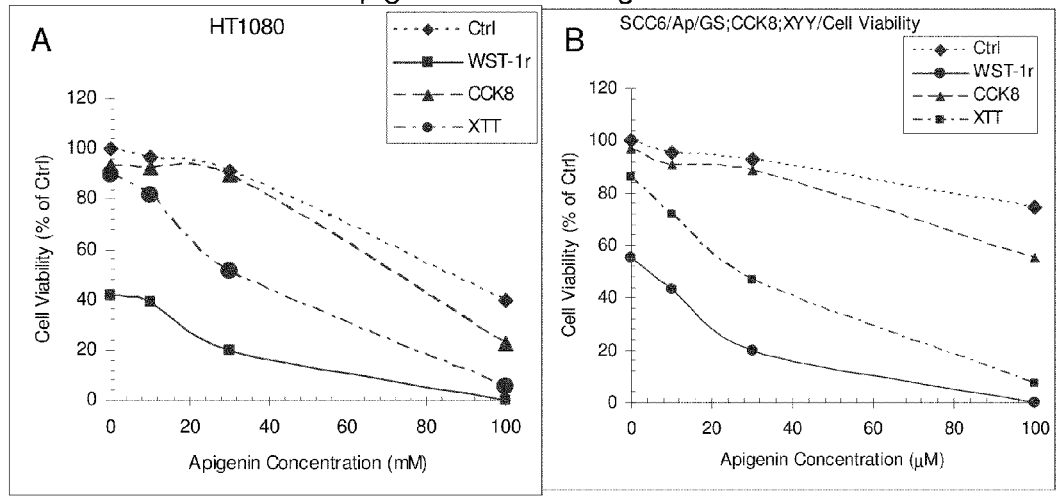
Fig 14 Effect of CCK8 and XTT as substitute of WST-1r in combination treatment with apigenin for inducing cancer cell death

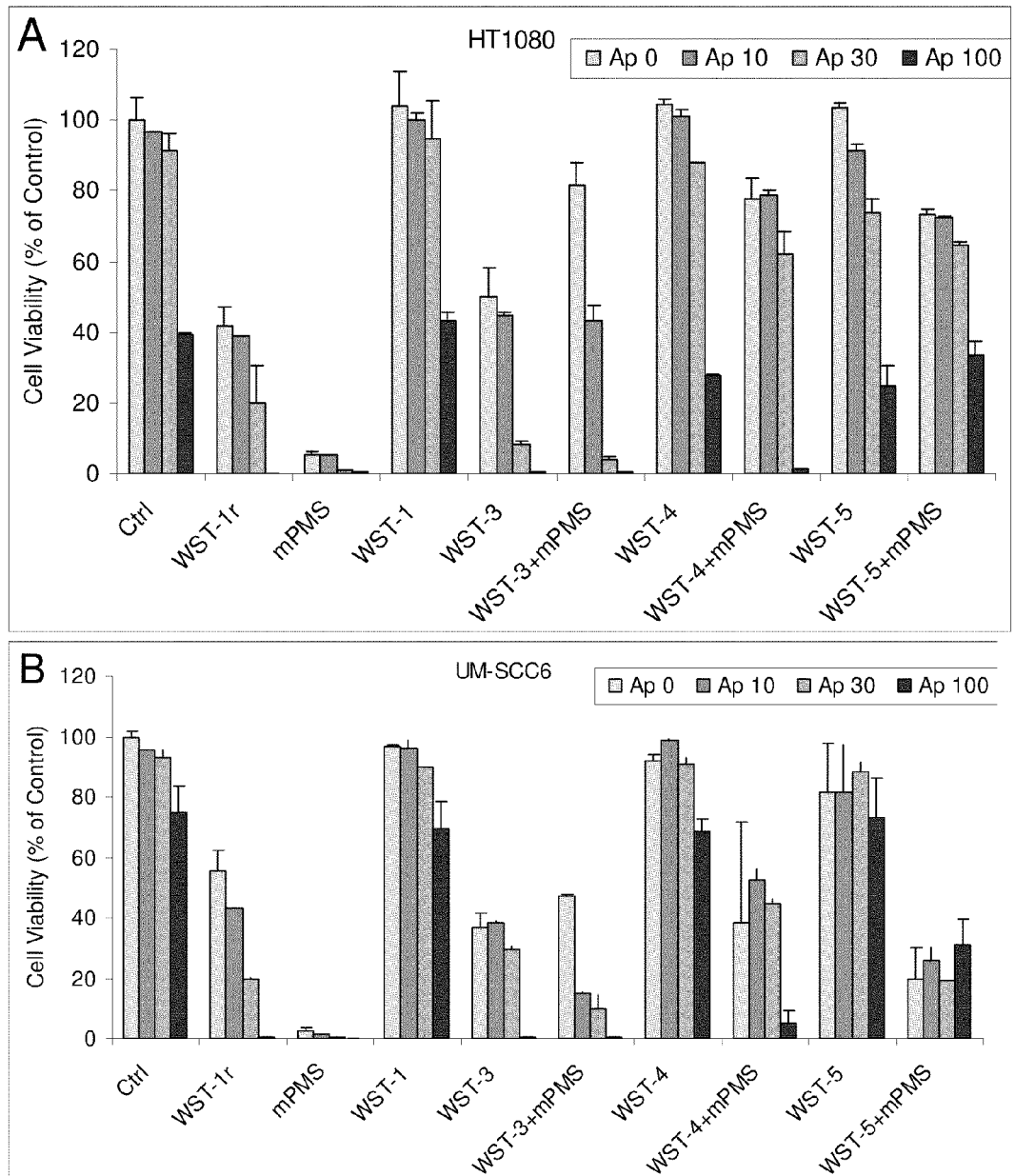
Fig 15. Combination Treatment of Apigenin with WST derivatives, mPMS or Combination of WST and mPMS
Ap=Apigenin

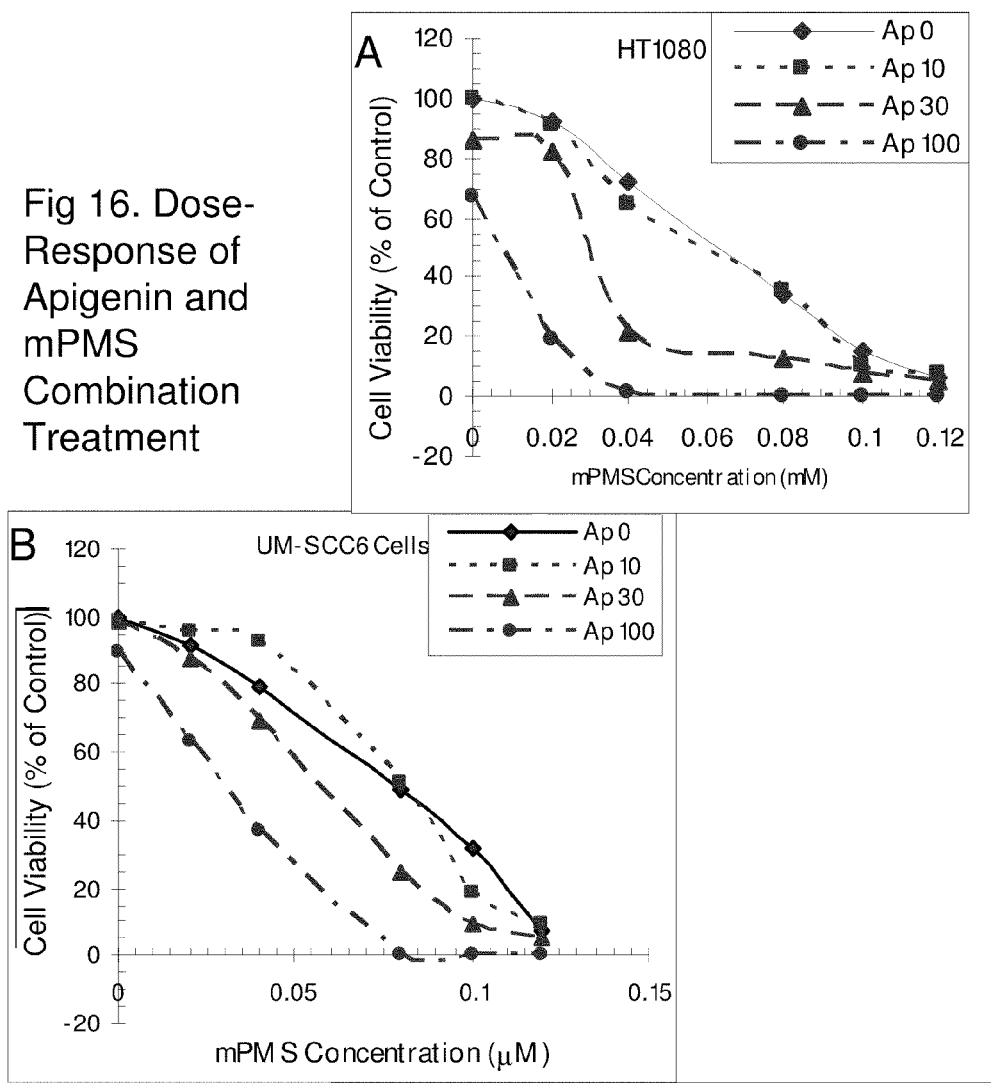
Fig 16. Dose-Response of Apigenin and mPMS Combination Treatment
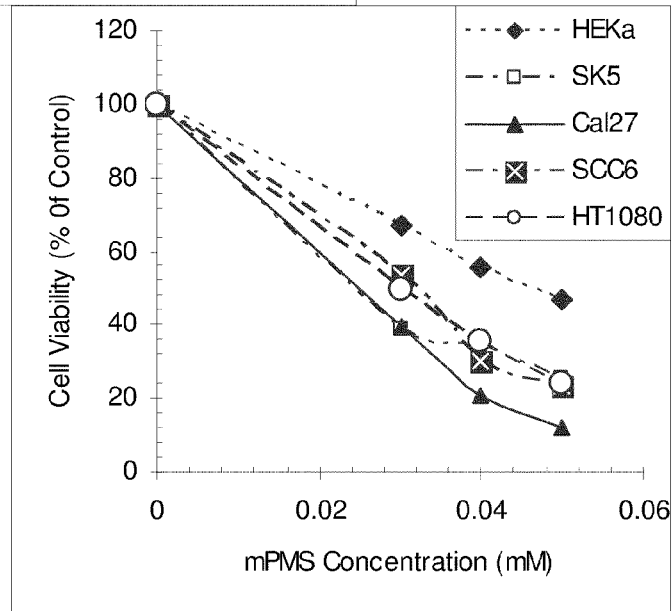
Fig 17 Differential Cellular Responses to mPNS Treatment

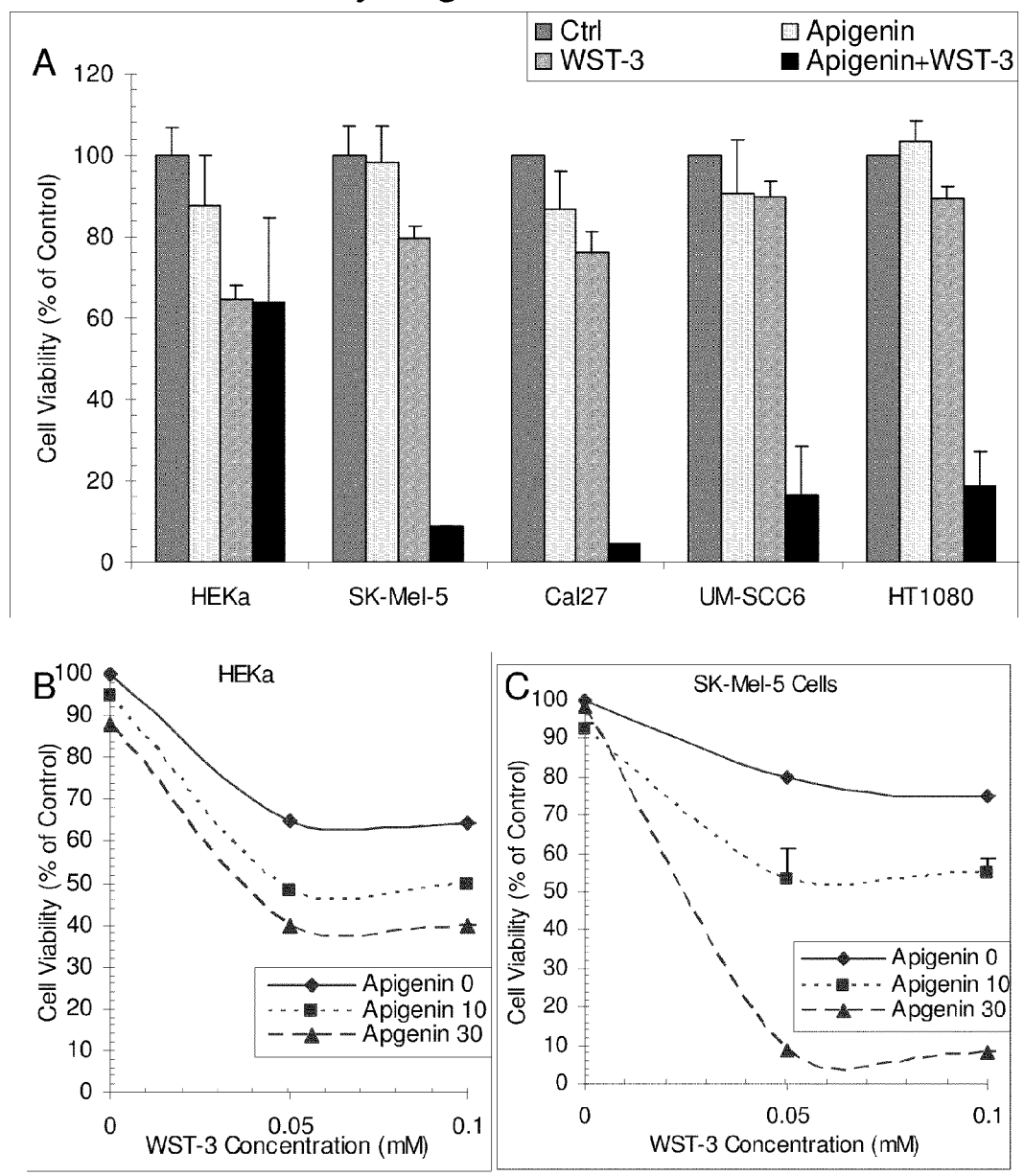

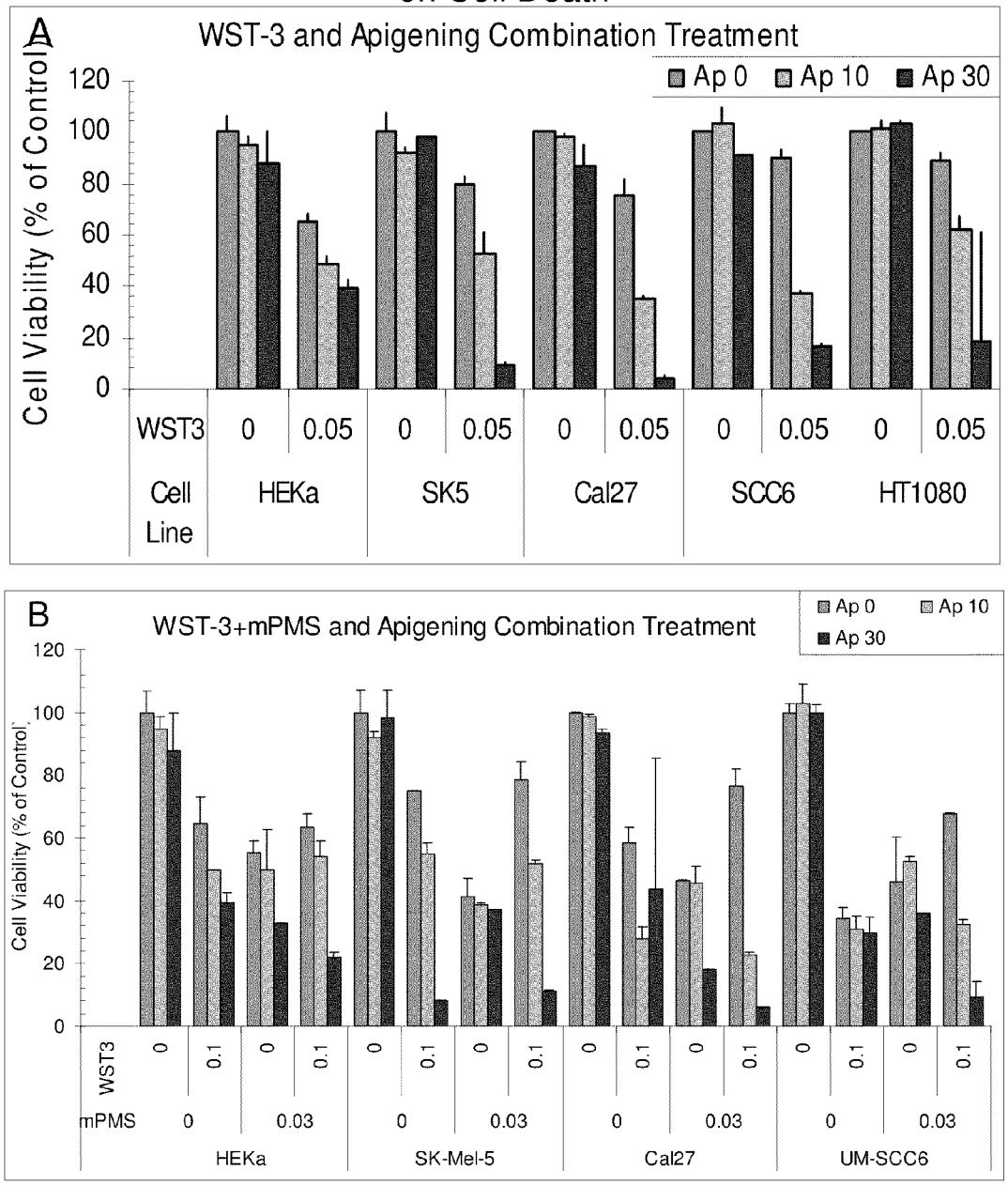
Fig 19. Effect of Combination WST-3-mPMS with Apigenin On Cell Death
Ap=Apigenin

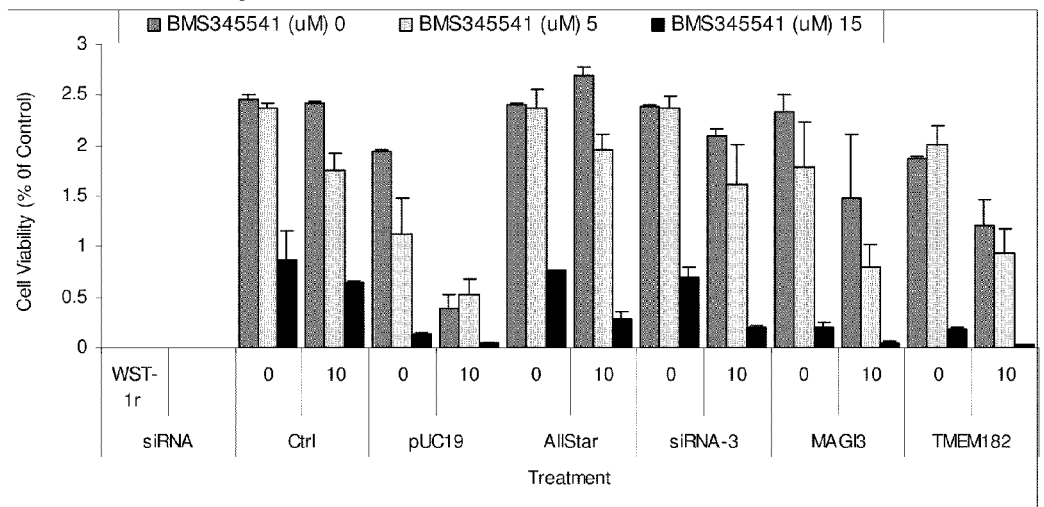
Fig 20. siRNA substitution of pUC19 for Enhancing WST-1r-IKK Inhibitor Combination Treatment Effect
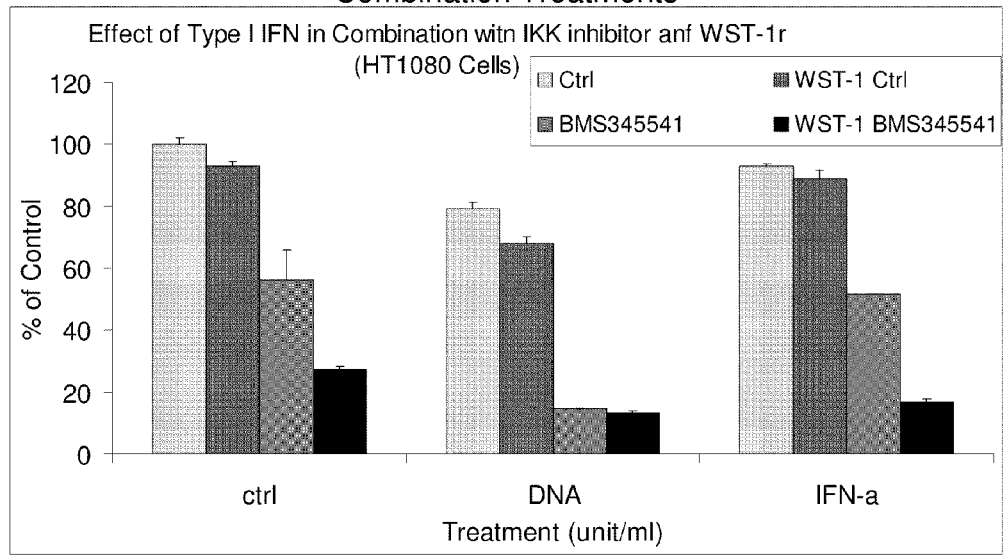
Fig 21 Effect of Type I IFN Substitute pUC19 Transfection in Combination Treatments

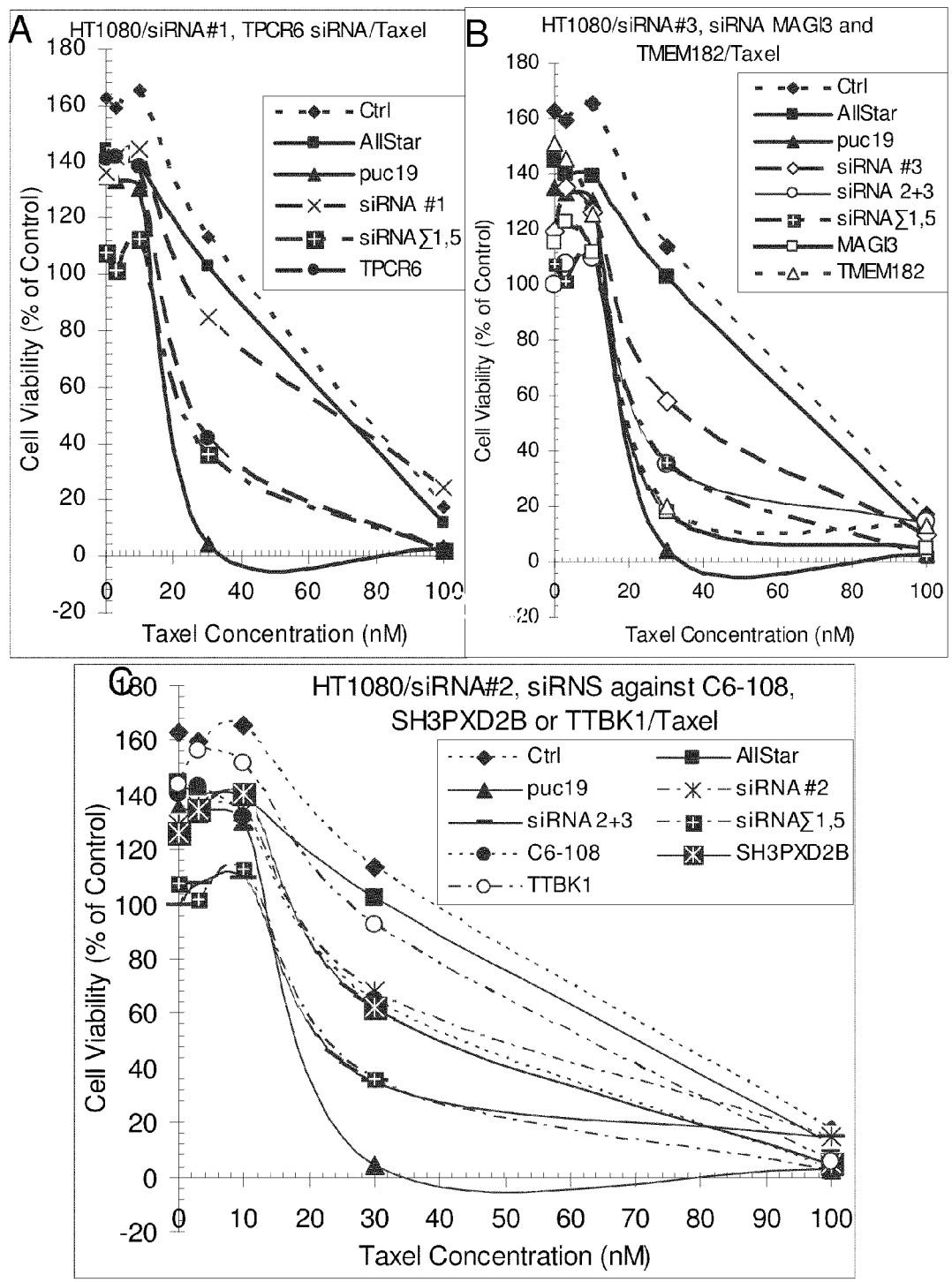
Fig 22. Enhancement of Taxel Efficacy Effects by Combination of Puc19 DNA sequence derived siRNA with Taxel

Fig 23 WST-1 Induces ROS Generation

A HT1080 Cell Treated with WSTGT-1r for 4 hours, then, labeled with CM-H2-DCFDA

| Label | PUC19 | CM-H2-DCFDA | WST-1 | Untreated | I-3 30μM | I-3 10μM | Untreated Control |
|---|---|---|---|---|---|---|---|
| 1A |  | + | + |  |  |  |  |
| 1B | + | + | + |  |  |  |  |
| 2A |  | + |  |  |  |  |  |
| 2B | + | + |  |  |  |  |  |

B HT1080 Cell labeled with CM-H2-DCFDA, then, Treated with WST-1r

| Label | PUC19 | CM-H2-DCFDA | WST-1 | Untreated | I-3 30μM | I-3 10μM | Untreated Control |
|---|---|---|---|---|---|---|---|
| 1A |  | + | + |  |  |  |  |
| 1B | + | + | + |  |  |  |  |
| 2A |  | + |  |  |  |  |  |
| 2B | + | + |  |  |  |  |  |

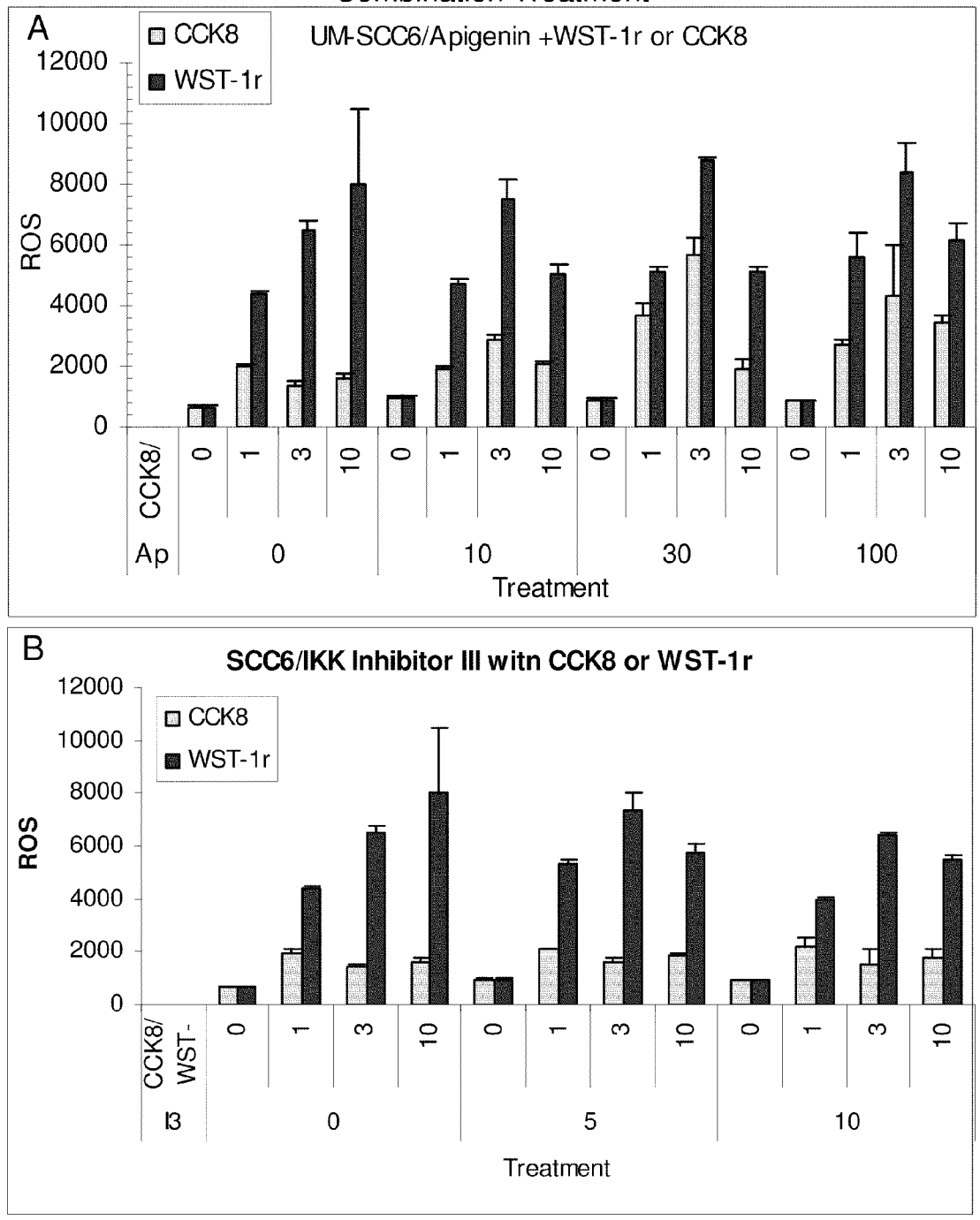
Fig 24. Comparison of ROS Generation by WST-1r and CCK8 in Combination Treatment

COMPOUNDS, COMPOSITION, METHODS, TARGETS FOR CANCER THERAPY

RELATED APPLICATION

This application is a continuation in part claims the benefit of PCT application (PCT/US2008/069106) filed on Jul. 2, 2008 claiming priority date of Jul. 2, 2007 and claims the benefit of U.S. Provisional Application No. 61/156,507, filed Mar. 1, 2009, which are herein incorporated by reference in their entirety.

GOVERNMENT INTERESTS

The research carried out in the present application was supported in part by NIH. The government may have certain rights in the invention of the present application.

SEQUENCE LISTING

Attached .txt file entitled: PCT/US2008/069106-SequenceListing
The sequence Listing contains the following sequences:
Nucleotide sequence of pUC19 and pCDNA3;
Nucleotide sequences: Transcripts of TRPC6 (NM_004621), SH3PXD2B (NM_001017995), MAGI3 (NM_152900), TMEM182 (NM_144632), C6orf108 (NM_199184);
Peptide sequences: TRPC6 (NP_004612), SH3PXD2B (NP_001017995), MAGI-3 (NP_690864), TMEM182 (NP_653233), C6orf108 (NP_954653);
Double strand RNA sequences: siRNA1, siRNA 2, and siRNA3.

DESCRIPTION OF THE INVENTION

1. Technical Field of the Invention

This invention relates to the fields of oncology and chemotherapy. Specifically, the invention provides novel compounds, methods, pharmaceutical composition and targets for more efficient and less or non cytotoxic treatments of cancer.

2. Background Art of the Invention

Up to date, chemotherapy and radiation therapy are still the mainstream for cancer treatment. These treatments were based on targeting proliferating cells rather than cancer cells only, which is also the cause fundamental basis of lethal side effects from these treatments. Targeted therapy, a new generation of cancer treatment, is aimed to target cancer specific changes of molecules and signaling pathways to induce cancer cell death, but limit such effects on normal cells. Enormous efforts have been made in finding the targets and the ways of targeting the targets inside the cells as a treatment. However, up to date, the success rate of this new generation is limited. One major challenge comes from the complexity of cellular regulation mechanisms and overlapping pathways inside the cells.

Aberrant Nuclear factor-kappa B (NF-κB) activation has been associated with a variety of tumors and cancer cells for oncogenesis, regulation of cell proliferation, inhibition of apoptosis, promoting angiogenesis, tumor invasion and metastasis as well as cancer cell resistance to chemotherapy and radiation therapy treatments (Kim H J, Hawke N, and Baldwin A S, NF-κB and IKK as therapeutic targets in cancer, *Cell Death ad Differentiation*, (2006) 13:738-47; Karin M, Nuclear factor-κB in cancer development and progression, (2006) *Natur* 441:431-6). Inhibition NF-κB activity could facilitate cancer cell death and sensitize cancer cells to chemotherapy drugs and radiation therapy (Kim H J, Hawke N, and Baldwin A S, NF-κB and IKK as therapeutic targets in cancer, *Cell Death and Differentiation*, (2006) 13:738-47; Karin M, Nuclear factor-kB in cancer development and progression, (2006) *Natur* 441:431-6; Chikashi Nakanishi and Masakazu Toi, Nuclear Factor-κB Inhibitors As Sensitizers To Anticancer Drugs, *NATURE REVIEWS CANCER* (2005) 5:297-309).

There are two similar, but different IκB Kinases (IKK1 and IKK2) that are up stream regulator of NF-κB activity. In addition, alternative NF-κB activation pathways, such as protein kinase CK2 (CK2), also exist. In most cancer cells, NF-κB is constitutively activated. In addition to the IKK classic pathway, these alternative NF-κB activation pathways may also contribute to the aberrant NF-κB activity in cancer cells (Ming Yu, Jason Yeh, and Carter Van Waes Protein Kinase CK2 Mediates Inhibitor-Kappa B Kinase and Aberrant Nuclear Factor-κB Activation by Serum Factor(s) in Head and Neck Squamous Carcinoma *Cells Cancer Research*, 2006 Jul. 1; 66(13): 6722-6731. and other for NFKB activation). Dozens of IKK inhibitors have been produced and are in trials for treating anti-inflammatory diseases. However, for treating cancer with these IKK inhibitors, these efforts have yielded results far from spectacular (Chikashi Nakanishi and Masakazu Toi, Nuclear Factor-κB Inhibitors As Sensitizers To Anticancer Drugs, *NATURE REVIEWS CANCER* (2005) 5:297-309).

More recent studies pointed to the balance between NF-κB activity and C-Jun-N-Terminal-kinase (JNK) activity, which regulates cell death or proliferation (reviews). In this theory, NF-κB and JNK cross talk through reactive oxygen species (ROS). Both JNK and NF-κB activity leads to Cell proliferation. However, ROS induces prolonged JNK activation that will induce programmed cell death. Conversely, activated NF-κB suppresses ROS and, hence, suppress ROS induced prolonged JNK activation. Therefore, inhibiting NF-κB while activating JNK would switch the balance to programmed cell death. However, up to date, no such treatment method has been reported. Most importantly, although this specific theory has been proposed, none has prior succeeded in demonstrating this effect.

ROS are potentially harmful by-products of normal cellular metabolism that directly affect cellular functions. ROS are also acts messenger and indispensable for signal transduction pathways that regulate cell growth and reduction-oxidation (redox) status. However, overproduction of these highly reactive oxygen metabolites can initiate lethal chain reactions, which involve oxidation and damage to structures that are crucial for cellular integrity and survival. In fact, many anti-tumor agents, such as vinblastine, cisplatin, mitomycin C, doxorubicin, camptothecin, inostamycin, neocarzinostatin and many others exhibit antitumor activity via ROS-dependent activation of apoptotic cell death, suggesting potential use of ROS as a fundamental antitumor principle. The "oxidation therapy" a unique anticancer strategy by inducing the generation of ROS directly to solid tumors as cytotoxic oxystress for cancer treatment has been developed. However no successful and practical results were obtained probably because of the lack of tumor selective ROS delivery and hence resulting in subsequent induction of severe side effects (Fang, J., Nakamura, H., and Iyer, A. K. Tumor-targeted induction of oxystress for cancer therapy. *J Drug Target*, 15: 475-486, 2007).

One of the unique features of cancer cells is their dependency on aerobic glycolysis, the "Warburg effect" that most cancer cells predominantly produce energy by glycolysis followed by lactic acid fermentation in the cytosol, rather than oxidation of pyruvate in mitochondria by most normal cells (Warburg O., *Science* 123:309, 1956). Along with this Aerobic glycolysis is that cancer cells consume oxygen through trans-plasma membrane electron transport (tPMET) at cell surface that oxidizes the NADH$^+$ that generated from the glycolysis processes in cytosol and to generate ATP (Heart, P M, Curr Mol Med, 2006, 6:895). The tPMET is mediated by NADH Oxidases (NOX) located on cell plasma membrane. This process oxidizes intracellular NADH and recycles it to maintain the intracellular NADH/NAD+ ratio to support glycolytic ATP. As ATP production contributes substantially to fulfilling the energy requirements of rapidly dividing cells, such as cancer cells, and that tPMET is the major source for cancer cell energy production that is different from normal cells, which perform energy metabolism and consume oxygen in mitochondrial. Therefore, targeting tPMET could be a strategy for cancer specific treatment. This concept was initially proposed by Herst P M, and Berridge M V based on the facts that the compounds that affect tPMET also affect cancer cell survival (Herst P M, Berridge M V, *Curr Mol Med* 6:895, 2006). It was further hypothesed that blocking the electron transport through interfering with membrane ubiquitou recycling, destabilizing the redox status of the cell membrane that may stimulate acid sphingo-myelinase activity, result in the conversion of sphigomyelin to ceramide that will lead to formation of ceramide-enriched membrane islands, which lead to apoptosis (Dumitru, C. A. et al, 2006, Oncogene 25:5612-25). Based on this hypothesis, Berridge et al proposed to make drugs specifically located to the plasma membrane without entering the cell as a novel anticancer drug development strategy. However, up to the date of filing this application, no such development had been reported.

Hypoxia inducing factor (HIF) and pyruvate kinase 2(PK-M2) are known to be responsible to the switch to aerobic glycolysis by cancer cells, but targeting PK-M2 resulted intolerable side effects. High HIF expression levels and activities have been associated with all cancer cells that make cancer cells resistant to low oxygen levels. Furthermore, cancer cells are actively undergoing catabolism, which result high demands for reducing sources that oxidize the NADH+ generated from the glycolysis process, which further makes cancer cells can survival in close to zero oxygen levels. Single inhibition of HIF seems not sufficient to kill cancer cells. More effective inhibition of cancer cell specific respiration is still lacking and has been sought hardly.

Apigenin is a naturally occurring plant flavone (4',5,7,-trihydroxyflavone) abundantly present in common fruits and vegetables including apple, parsley, onions, oranges, tea, chamomile, wheat sprouts and some seasonings. Apigenin is a multi function signal conduction agent and has been shown to possess remarkable anti-inflammatory, antioxidant and anti-carcinogenic properties and is currently under active study. Studies on the biological effects of apigenin at cellular and molecular levels have found that apigenin interferes with a wide range of critical molecules and signaling and regulatory processes in the cells, including depleting the HER2 protein and suppressing the Her2/Her3-phosphatidylinositide 3-kinase/AKT pathway (Way, T. D. and Lin, J. K. Role of HER2/HER3 co-receptor in breast carcinogenesis. *Future Oncol*, 1: 841-849, 2005), inhibit HIF, PKC, CDK, VEGF NF-κB, CK2, AKT, MAPK, AR and ER pathways, activate wild type p53, modulate the deregulated cell cycle checkpoint and induce apoptosis (*Induction of caspase-dependent, p53-mediated apoptosis by apigenin in human neuroblastoma*—Torkin et al. 4 (1): 1—. 2007; *Apigenin Inhibits Expression of Vascular Endothelial Growth Factor and Angiogenesis in Human Lung Cancer Cells: Implication of.* 2007; *Apigenin inhibits VEGF and HIF*-1 *expression via PI3K/AKT/p70S6K1 and HDM2/p53 pathways*—Fang et al. 19 (3): 342—*The FASEB*. 2007; Balasubramanian, S. and Eckert, R. L. Keratinocyte proliferation, differentiation, and apoptosis—differential mechanisms of regulation by curcumin, EGCG and apigenin. *Toxicol Appl Pharmacol*, 224: 214-219, 2007; Birt, D. F., Walker, B., Tibbels, M. G., and Bresnick, E. Anti-mutagenesis and anti-promotion by apigenin, robinetin and indole-3-carbinol. *Carcinogenesis*, 7: 959-963, 1986; Patel, D., Shukla, S., and Gupta, S. Apigenin and cancer chemoprevention: progress, potential and promise (review). *Int J Oncol*, 30: 233-245, 2007; Sato, F., Matsukawa, Y., Matsumoto, K, Nishino, H., and Sakai, T Apigenin induces morphological differentiation and G2-M arrest in rat neuronal cells. *Biochem Biophys Res Commun* 1994 Oct. 28; 204: 578-584, 1994). In addition, apigenin has also been reported to generate ROS, which disrupt mitochondrial membranes. Current research trials indicate that it may reduce DNA oxidative damage; inhibit the growth of human leukemia cells and induced these cells to differentiate; inhibit cancer cell signal transduction and induce apoptosis; act as an anti-inflammatory; and as an anti-spasmodic or spasmolytic. More than 100 patent applications related to apigenin have been filed. Among those, apigenin was claimed to be used as a drug for treating inflammatory and autoimmune diseases. In addition, apigenin was also claimed for the use as a cancer chemoprevention drug and as adjunct use for enhancing the effects of chemotherapy drugs for cancer treatment at 10 μM concentration (US Patent Application 20060189680). However, as a chemo sensitizer, the efficacy effect of apigenin is limited. To be a cytotoxic drug for treating cancer, apigenin has to be combined with other treatments. Other isoforms of apigenin, other flavonoids, isoflavonoids including, naturaly existed, modified or synthetic including phenoxodiol a synthetic isoflevene, have also been found with similar function of apigenin. All of those need to be combined with chemotherapy drugs for cancer treatment.

SUMMARY OF THE INVENTION

A more efficient and cancer specific anticancer treatment can be achieved by combining inhibition of cancer cell surface respiration with inhibiting its hypoxia response.

The present invention provides pharmaceutical composition and combinational composition and methods for the treatments of cancer and genes as drug targets to enable the treatment of cancer in a mammal to synergize cancer specific cell death with less or no cytotoxic side effects including:

A pharmaceutical composition and a method for treating cancer by targeting the tPMET of cancer cells to block the tarns plasma membrane electron transfer and/or uncoupling the oxidative phosphorylation across the cell plasma membrane without affecting the same function at the mitochondria membrane in combination inhibition of cellular responses to hypoxia to reach a synergistic therapeutic effect of inducing cancer specific cell death for cancer treatment;

A compound and its required chemical structure for targeting tPMET for cancer treatment;

A use of WST-3 and any of the valid substitutes that are capable of blocking the tPMET by uncoupling the oxidative phposphorylation on cell plasma membrane for the said combination treatment;

A pharmaceutical composition and a method for treating cancer by combining WST-3 or its valid substitutes with apiginin or its valid substitutes as an cancer specific and less toxic anticancer treatment;

A use of a reagent WST-1r comprising water soluble tetrozolium salts and intermediate electron acceptors as a drug to interfere tPMET for the said combination treatment;

A pharmaceutical composition of WST-1r and any of the valid substitutes of WST-1r for the said combination treatment that are capable of conducting trans-plasma membrane electron transport and induces ROS. The WST-1r and any of the valid substitutes of WST-1 is a mixture of tetrazolium salt and an electron coupling reagent (IEA), or at least one of the tetrazolium salt or at least one of the IEA in optimized concentration. The compounds may be administered in a pharmaceutically acceptable carrier medium.

A pharmaceutical composition and a method for treating cancer by combining WST-1r or its valid substitutes with apiginin or its valid substitutes as an cancer specific and less toxic anticancer treatment;

Selected genes, molecules, and polynucleotide sequences and polypeptide sequences are provided as target for designing drugs for the treatment of a cancer in a patient in need. These targets are the human transcripts, and their corresponding protein/peptide molecules and/or the genomic DNA sequences that are selected from the blast analysis of the DNA sequence of pUC19 DNA vector against human genome and treanscripts, the DNA sequences of which mapped to the human transcripts and/or genomic sequences in short pieces. The transcripts and their corresponding coding molecules are targets for enhancing the efficacy of the treatments of cancer. Other sequences that, thus, mapped to human genomic sequences may be used as targets as well as being used for targeting these corresponding genes. The potential drugs that can be designed to targeting these targets include, but not limited to, siRNA, small molecule inhibitors, peptides inhibitors, anti-sense RNA, anti-sense Oligo, antibodies, antibody fragments, proteins, dominant negative DNA vectors and Interferon (IFN). In a particular embodiment of this invention, these targets are, but not limited to, polynucleotide sequences of TRPC6 (SEQ ID NO: 2), MAGI-3(SEQ ID NO: 4), TMEM182 (SEQ ID NO: 5), SH3PXD2B(SEQ ID NO: 3), or c60rf108 (SEQ ID NO: 14), and the polypeptide sequences of TRPC6 (SEQ ID NO: 6), MAGI-3(SEQ ID NO: 8), TMEM182 (SEQ ID NO: 9), SH3PXD2B(SEQ ID NO: 7), or c60rf108 (SEQ ID NO: 15). The sequence to target human genomic sequence and or transcripts are, but not limited to, puc19 DNA vector (SEQ ID NO: 1), pc DNA3 vector (SEQ ID NO: 13), siRNA2 (SEQ ID NO: 10-12). Synthetic siRNA that against these target genes (SEQ ID NO: 2-5 and SEQ ID NO: 14) were selected for demonstrating the potential use of these genes as a target for the combination treatment for cancer;

A method for treating a cancer in a patient in need thereof comprising administering to the patient, concurrently or sequentially, a therapeutically effective amount of (1) at least one of the transfection of puc19 DNA vector or administering at least one of the substitutes of puc19 DNA transfection and (2) at least one IKK inhibitor and (3) an additional third agent, WST-1r or at least one of the valid substitutes of WST-1r, in a pharmaceutically acceptable carrier medium. Wherein said combination enhances the induction of cancer cell death while otherwise any of these agents separately are demonstrated not to be toxic.

The valid substitutes for Puc19 DNA transfection are selected from the group consisting of (1) type I IFN, (2) Synthetic small interfering RNAs (siRNA) the nucleotide sequence SEQ ID NO 10-12 of which mapped to both the DNA sequence of the pUC19 DNA vector and human transcripts and genome DNA sequences, (3) the biological compounds selected from the group consisting of biological and non-biological organic or non-organic compounds. The said method of screening compounds, wherein said biological chemicals are further selected from the group of polypeptides, proteins, peptides, antibodies, antibody fragments, nucleic acids, and polynucleotide the products of which interact and interfere said selected targets of the polynucleotide sequences of TRPC6 (SEQ ID NO: 2), MAGI-3(SEQ ID NO: 4), TMEM182 (SEQ ID NO: 5), SH3PXD2B(SEQ ID NO: 3), or c60rf108 (SEQ ID NO: 14), and the polypeptide sequences of TRPC6 (SEQ ID NO: 6), MAGI-3(SEQ ID NO: 8), TMEM182 (SEQ ID NO: 9), SH3PXD2B(SEQ ID NO: 7), or c60rf108 (SEQ ID NO: 15). Synthetic siRNA that against these target genes (SEQ ID NO: 2 to 5 and SEQ ID NO: 14) were selected for demonstrating the potential use of these genes as a target for the combination treatment for cancer;

A method of inducing programmed cell death of cancer cells in a malignant cell population, and treating a patient with cancer comprising the use of a combination therapy. The combination therapy of the present invention comprises administering an effective dose of WST-1r or any valid substitutes, that is capable of conducting trans-plasma membrane electron transfer and induces ROS in a cell and apigenin, a multi-function inhibitor that inhibits HIF, CK2, NF-κB activity and other molecules and/or signaling pathways, or at least one of the IKK inhibitor. The said combination treatment enhances apigenin anti-neoplasm effect and synergizes the induced cancer cell death;

A method is provided for treating a cancer in a patient in need thereof by administering to the patient, concurrently or sequentially, a therapeutically effective amount of at least one GSK3β inhibitor and protein kinase CK2 (CK2) inhibitor and addition of a third agent, WST-1r. In a particular embodiment of the invention, the preferred at least one GSK3β inhibitor is LiCl and the preferred protein kinase CK2 (CK2) inhibitor is Apigenin. The compounds may be administered in a pharmaceutically acceptable carrier medium. Wherein said combination enhances the induction of cancer cell death otherwise any of these agents separately are demonstrated not to be toxic;

A method is provided for treating cancer in a patient in need comprising administering, concurrently or sequentially, a therapeutically effective amount of a combination of a selective Puc19 DNA trasnfection or at least one of any of the valid substitutes of puc19 transfection as listed above in combination with at least one of a selected approved chemotherapeutic agents. Wherein said Puc19 DNA trasnfection or administering at least one of the valid substitutes of puc19 transfection being capable of substantially enhancing anti-neoplastic effects of said proved chemotherapeutic agents, substantially reducing toxic side effects of said chemotherapeutic agents, or a combination thereof, wherein said Puc19 DNA trasnfection or at least one of the valid substitutes has a substantial effect on activity of said chemotherapeutic agents;

A method is provided for synergistically inhibiting NF-κBNF-KAPPAB activity in cancer cells and in a patient in need thereof by administering to the cells or patient, concurrently or sequentially, a therapeutically effective amount of at least one Dominant negative kinase dead IKK1 DNA vector (IKK1-KA) and at least one Dominant negative kinase dead IKK2 DNA vector (IKK2-KA). The at least one Dominant negative kinase dead IKK1-KA or IKK2-KA may be substituted by IKK inhibitors selected from the group consisting of (IKK inhibitor list). The compounds may be administered in a pharmaceutically acceptable carrier medium. This combinational inhibition effect may be further enhanced by adding a third agent, WST-1r or the valid substitutes of WST-1r, for further induction of cancer cell death;

A method of inducing cancer cell death, and treating a patient comprising the use of a combination therapy. The combination therapy of the present invention comprises administering an effective dose of at least a compound that inhibits NF-κB activity and at least one compound that inhibits STAT3 in a preferred embodiment, the compound that inhibits NF-κB activity is apigenin or an IKK inhibitor or a CK2 inhibitor and the compound that inhibits STAT is stattic. The compounds may be administered in a pharmaceutically acceptable carrier.

A use of the combination therapy to treat cancers comprising administering IKK inhibitor or apigenin and a STAT3 inhibitor, stattic. In one preferred embodiment, the cancers are selected from the group consisting of a subtype of head and neck squamous carcinoma.

BRIEF DESCRIPTION OF THE FIGURES

FIG. 1. Chemical Structure of DNP and WST-3

FIG. 2. Chart of endogenous NF-κB down stream gene expression levels.

FIG. 3. Chart of cell survival from IKK-KA transfection in combination with or without WST-1 treatment.

FIG. 4 Chart of WST-1 promotes HT1080 Human Sarcoma cell death by triple combination Treatment FIG. 5 Chart of combination of LiCl and Apigenin and WST-1r treatment.

FIG. 6 Chart of pUC19 DNA transfection synergize chemotherapeutic drug effect

FIG. 7 Chart of Time Course of ROS generation after combination treatment of WST-1r, CCK8 with apigenin and IKK inhibitor III FIG. 8 Chart of combination treatment with apigenin and WST-1r synergizes induced cancer cell death.

FIG. 9. Chart for Differential Responses to WST-1r and Apigenin Combination Treatment from Human Non-Cancer Cells and Human Head and Neck Cancer Cells.

FIG. 10 Chart of Time course and Dose Response of WST-1r and Dose-Response of apigenin involved in the combination treatment of WST-1r with apigenin.

FIG. 11 Chart showing Effect of Combination treatment with IKK Inhibitor and WST-1r on melanoma cell lines FIG. 12 Chart of effects of treatment order of WST-1r and BMS345541 on induced cell death FIG. 13 Chart showing WST-1r and Apigenin combination treatment induced JNK Phosphrylation FIG. 14 Chart of Effects of CCK8 and XTTas substitute of WST-1r in combination treatment with apigenin for inducing cancer cell death FIG. 15 Chart of Combination Treatment of Apigenin with WST derivatives, mPMS or Combination of WST and mPMS FIG. 16 Chart of Dose-Response of Apigenin and mPMS Combination Treatment FIG. 17 Chart of Differential cellular responses to mPMS treatment FIG. 18 Chart of Effect of Combination WST-3 with Apigenin 0n Cell Death FIG. 19 Chart of Effect of WST-3, and WST-3+mPMS in Combination with Apigenin 0n Inducing Cancer Cell Death FIG. 20 Chart of siRNA substitution of pUC19 for enhancing WST-1r-IKK inhibitor combination Treatment Effect FIG. 21. Chart for Effect of Type I INF Substitute pUC19 for combination Cancer treatment FIG. 22. Chart of enhancement of Taxel Efficacy Effects by Combination of Puc19 DNA sequence derived siRNA with Taxel FIG. 23. Image of Induction od ROS Generation by WST-1r and the combination treatment.

FIG. 24 Chart of Dose Response of ROS generation after combination treatment of WST-1r, CCK8 with apigenin and IKK inhibitor III

DETAILED DESCRIPTION OF THE INVENTION

I. General Description

The efficacy of anticancer therapy can be enhanced by combination of proper selected compounds, biological molecules and drugs that block the tPMET and cell surface respiration in combination with inhibiting cellular hypoxia responses to induce synergistic and cancer cell specific cell death. Several combinational pharmaceutical compositions and methods for anticancer treatment are described. The development of these pharmaceutical compositions were based on the following discoveries:

The discovery the use of WST-3, WST-1r and their valid substitutes as drugs for combination therapies by combining with apigenin, IKK inhibitors or Puc19 DNA or any of its valid substitutes that induced synergetic and cancer specific cell death, The discovery the structure and function features of WST-3 representing a class chemicals of a cell surface oxidative-phosphorylation uncpupler and the corresponding principle to design a chemical compound for targeting tPMET and blocking cell surface oxidative-phosphorylaition, tPMET and cell respiration for the said combination anticancer treatment.

(3) The use of puc19 DNA sequences and the corresponding siRNAs as anti cancer drugs as well as the discovery of the corresponding genes as target for developing anticancer therapy.

(4) The discovery of the method and combinational composition of WST-3 and apigenin or their valid substitutes as anticancer treatment.

(5) The discovery of the method and combinational composition of WST-1r and apigenin or their valid substitutes as anticancer treatment.

The first and the second discoveries led to the identification of classes of chemicals and corresponding pharmaceutical compositions of using these chemical compounds as drugs for the combination treatment for cancer. The third finding further led to the discovery of several genes as targets for developing anticancer drugs. These are rarely studied genes and some of them are still in hypothetical gene status. Together, these findings led to establishing several combinational treatment methods for cancer therapy.

In one embodiment, the pharmaceutical composition of WST-3 was described as a cell surface oxidative-phosphorylation uncouple for the use as drugs for combinational treatment of cancer.

In one embodiment, the pharmaceutical composition of WST-1r was described an agent that interferes tPMET for the use as drugs for combinational treatment of cancer.

Yet in another embodiment, the classes of chemical compounds of WST-3 and their special chemical structures for designing drugs to direct target the tPMET and as an uncoupler to block the cell surface energy metabolism and cell surface respiration are descried for the use of the combination treatment for cancer.

Yet in another embodiment, the classes of chemical compounds and the combination of these compounds that can form the formula of WST-1r and the valid substitutes of WST-1r are descried for the use of the combination treatment for cancer.

In one of the embodiments, Puc19 DNA vector was found to have biological effect on mammalian and human cancer cells and was used as a drug for combination treatment with WST-1r reagents and with or without IKK inhibitors.

In another embodiment, Puc19 DNA vector was used as a drug in combination with chemotherapeutic drug for enhancing the therapeutic effect of these chemotherapeutic drugs for the treatment of cancer.

According to the above embodiments, small interfering RNAs (SEQ-ID No:10-12), the sequence of which were derived from the nucleotide sequence of Puc19 DNA vector, were described for the use of combination treatments for cancer.

Yet also according to the above embodiments, human genes (TRPC6 (SEQ ID NO: 2), MAGI-3(SEQ ID NO: 4), TMEM182 (SEQ ID NO: 5), SH3PXD2B(SEQ ID NO: 3), or c60rf108 (SEQ ID NO: 14), and the polypeptide sequences of TRPC6 (SEQ ID NO: 6), MAGI-3(SEQ ID NO: 8), TMEM182 (SEQ ID NO: 9), SH3PXD2B(SEQ ID NO: 7), or c60rf108 (SEQ ID NO: 15)) that were selected based on Puc19 DNA sequence analysis and the biological function of the corresponding siRNAs to be used as target for drug development for the treatment of cancer are described.

Yet another embodiment, wherein said the valid substitutes of Puc19 DNA that were selected from biological and non-biological compounds and their effects in combination with WST-1r or the valid substitutes of WST-1r and with or without IKK inhibitor is described. Wherein said the biological compound for the valid substitutes of Puc19 DNA include different members of Interferon and all the siRNAs mentioned above.

Yet another embodiment, wherein said the valid substitutes of Puc19 DNA that were selected from biological and non-biological compounds and their effects in combination with chemotherapeutic drugs is described. Wherein said the biological compound for the valid substitutes of Puc19 DNA include different members of Interferon and all the siRNAs mentioned above.

In another embodiment, a medical use of combination treatment for cancer comprising apigenin, the flavonoids or at least one IKK inhibitor and WST-1r is described.

Yet in another embodiment, a medical use of combination treatment for cancer comprising at least one Protein kinase II (CK2) inhibitor, apigenin, at least one GSK3β inhibitor, Lithium chloride, and WST-1r for enhancing treatment effect is described.

II. Definitions

The term "pUC19 DNA" is a DNA cloning vector (SEQ ID #1) that amplifies in prokaryotic cells. DNA sequence of this vector was originally submitted to NCBI gene bank by J. Messing, Waksman Institute, N.J. on 3-MAR-1986 and revised by F. Pfeiffer on 16-DEC-1986. In the present description, pUC19 has been used as a drug for anticancer therapy by transfected into human cancer cells.

The data suggests that the DNA sequence that composes this DNA vector has biological effects in cultured human cancer cells that lead to synergistic cell death when combined with other treatments to these cells as described in this description. Blast analysis of the DNA sequence of pUC19 against human genome and transcripts for short matches showed multiple short sequences aligned to varies locations of flanking sequences of human genome and transcripts (Blast result is attached to this application). In the present description, pUC19 represents the combination of short DNA sequences, usually 15-100 bases that mapped to human transcripts and/or flanking regions of genes of human genome DNA sequences. Accordingly, the corresponding gene products are the targets of the pUC19. The polynucleotide sequences and amino acid sequences that include but not limited to siRNA, miRNA, shRNA, peptide that are directly derived from the pUC19 DNA sequence as well as derived from the corresponding genes and small molecules and antibodies that can interact and/or inhibit the function and activity of these corresponding molecules as direct gene products of their DNA sequences, the DNA sequences of their corresponding gene contain these short matched DNA sequences from the DNA sequence of pUC19. The matched DNA sequences don't have to be exact matches. The matched DNA sequences can vary slightly, 10%, 20%, and even up to 30-40%.

The term "pcDNA3m DNA" is a mammalian expression vector version 3.1 with modifications [SEQ ID #13]. DNA sequence of this vector was originally derived from the pUC19 with further modifications and obtained from Invitrogen, which has discontinued the production and selling of this vector. pcDNA3 has been transfected into human cancer cells by chemical or liposome based DNA transfection reagents. Similar to pUC19, the DNA sequence that composes this DNA vector have biological effects in cultured human cancer cells that lead to synergistic cell death when combined with other treatments to these cells as described. In the present description, pcDNA3 represents the short DNA sequences, usually 15-100 bases that mapped to human transcripts and/or human genome DNA sequences, and their corresponding gene products that include but not limited to siRNA, miRNA, shRNA, peptide that are directly derived from the DNA sequence of this vector and small molecules that can interact and/or inhibit the function and activity of these corresponding molecules as direct gene products of their gene sequences, the DNA sequences of their corresponding gene contain these short matched DNA sequences from the DNA sequence of pcDNA3. The matched DNA sequences don't have to be exact matches. The matched DNA sequences can vary up to 30-40% changes.

The term "siRNA1" [SEQ ID #10] is a siRNA designed based on and derived from the DNA sequence of pUC19 [SEQ ID #1]. This siRNA sequence matches to the human transcript of *Homo sapiens* transient receptor potential cation channel, subfamily C, member 6(TRPC6, GeneID: 7225), mRNA (gi|19923256|NM_004621.3) synonyms: TRP6, FSGS2, FLJ11098. In the present description, siRNA1 was used as a drug for targeting TRPC6 for the treatment of cancer. As in general the siRNA sequence can vary slightly, 10%, 20% and even 30-40% of the exact sequence of the transcript.

The term "siRNA3" [SEQ ID #12]. is a siRNA designed based on and derived from the pUC19DNA sequence [SEQ ID #1]. This siRNA sequence matches to the human transcript of *Homo sapiens* membrane associated guanylate kinase, WW and PDZ domain containing 3 (MAGI3, GeneID: 260425), transcript variant 2, mRNA (NM_152900.1) synonyms: MAGI-3, MGC163281 and the *Homo sapiens* transmembrane protein 182 (TMEM182, GeneID: 130827), mRNA (NM_144632.2). In the present description, siRNA3 was used as drug for targeting MAGI3 and/or TMEM182 for the treatment of cancer. As in general the siRNA sequence can vary slightly, 10%, 20% and even 30-40% of the exact sequence of the transcript.

The term "siRNA2" [SEQ ID #11] is a siRNA designed based on and derived from the DNA sequence of pUC19 [SEQ ID#1]. The ⅔ of this siRNA sequence matches to the human transcript of *Homo sapiens* SH3 and PX domains 2B (SH3PXD2B), mRNA. (SH3PXD2B, GeneID: 285590), mRNA (NM_001017995) synonyms: HOFI; FLJ20831; KIAA1295. In addition, this sequence also mapped to more than 45 sites within flankin sequences of human genome. In the present description, siRNA2 was used for targeting SH3PXD2B and all the other potential DNA sequences in the human genome for the treatment of cancer. As in general the siRNA sequence can vary 30-40% of the exact sequence of the transcript.

The term "TRPC6" [Nucleotide SEQ ID #2, Peptide SEQ ID #6] represents human transcript of *Homo sapiens* transient receptor potential cation channel, subfamily C, member 6(TRPC6, GeneID: 7225), mRNA (NM_004621.3) synonyms: TRPC6, FSGS2, FLJ11098. In the present description, TRPC6 is a target for developing anticancer treatment. TRPC6 can be targeted by any means that alter its expression levels and activities at functioning levels including but not limited to poly nucleotides, such as siRNA, shRNA, anti-sense RNA, anti-sense DNA oligo, and dominant negative DNA vectors, peptide and amino acid sequences, such as peptide, and antibodies, and small molecule inhibitors. The TRPC6 has been previous reported as a potential target for cancer treatment, but no report regarding the use of TRPC6 as a target for a combinational cancer treatment with IKK inhibitors, WST1r or chemotherapy drugs to reach the synergistic effect of promoting cancer cell death. The siRNA1 sequence described above is the preferred sequence, but this does not limit from other siRNA sequences and other means as described in this paragraph. As in general the siRNA sequence can vary slightly, 10%, 20% and even 30-40% from the exact sequence of the transcript.

The term "MAGI3" [Nucleotide SEQ ID #4, Peptide SEQ ID #8] represents human transcript of *Homo sapiens* membrane associated guanylate kinase, WW and PDZ domain containing 3 (MAGI3, GeneID: 260425), transcript variant 2, mRNA (NM_152900.1). Synonyms: MAGI-3, MGC163281. MAGI-3 is localized with ZO-1 and cingulin at tight junctions in epithelial cells, whereas MAGI-3 was found in E-cadherin-based cell-cell contacts and in focal adhesion sites in primary cultured astrocytes (Adamsky K, Arnold K, Sabanay H, Peles E., Junctional protein MAGIKK interacts with receptor tyrosine phosphatase beta (RPTP beta) and tyrosine-phosphorylated proteins. (*J Cell Sci.* 2003,116(Pt 7): 1279-89). MAGI-3 interacts directly with LPA(2) and regulates the ability of LPA(2) to activate Erk and RhoA MAGIKK regulates LPA-induced activation of Erk and RhoA (Zhang H, Wang D, Sun H, Hall R A, Yun C C, *Cell Signal.* 2007 February; 19(2):261-8. *Epub* 2006 Aug. 9). The function of MAGI3 has been previous linked to cancer, but no report regarding the use of MAGI3 as a target for a combinational cancer treatment with WST-1r, IKK inhibitors or chemotherapy drugs to reach the synergistic inhibition of cancer cell growth and to promote cancer cell death. In the present description, MAGI3 is a target for developing anticancer treatment. MAGI-3 can be targeted by any means that alter its expression levels and activities at functioning levels including but not limited to poly nucleotides, such as siRNA, shRNA, anti-sense RNA, anti-sense DNA oligo, and dominant negative DNA vectors, peptide and amino acid sequences, such as peptide, and antibodies, and small molecule inhibitors. The siRNA3 sequence described above is the preferred sequence, but this does not limit from other siRNA sequences and other means as described in this paragraph. As in general the siRNA sequence can vary slightly, 10%, 20% and even 30-40% from the exact sequence of the transcript.

The term "TMEM182" [Nucleotide SEQ ID #5, Peptide SEQ ID #9] represents *Homo sapiens* trans-membrane protein 182 (TMEM182, GeneID: 130827), mRNA (NM_144632.2). In the present description, SH3PXD2B is a target for developing anticancer treatment. TMEM182 can be targeted by any means that alter its expression levels and activities at functioning levels including but not limited to poly nucleotides, such as siRNA, shRNA, anti-sense RNA, anti-sense DNA oligo, and dominant negative DNA vectors, peptide and amino acid sequences, such as peptide, and antibodies, and small molecule inhibitors. The siRNA3 sequence described above is the preferred sequence, but this does not limit from other siRNA sequences and other means as described in this paragraph. As in general the siRNA sequence can vary 10%, 20% and even 30-40% from the exact sequence of the transcript. TMEM182 has not been previously studied and not been linked to cancer.

The term "SH3PXD2B" [Nucleotide SEQ ID #3, Peptide SEQ ID #7] represents SH3 and PX domains 2B adaptor protein HOFI (GeneID: 285590) that contains SH3 and PX domains. SH3 domains, Src homology 3 domains, bind to prolinerich ligands with moderate affinity and selectivity, preferentially to PxxP motifs; they play a role in the regulation of enzymes by intramolecular interactions, changing the subcellular localization of PX; PhoX homologous domain, present in p47phox and p40phox. Eukaryotic domain of unknown function presents in phox proteins, PLD isoforms, and a PI3K isoform. SHPXD2B has not been previously studied and not been linked to cancer. In the present description, SH3PXD2B is a target for developing anticancer treatment. SH3PXD2B can be targeted by any means that alter its expression levels and activities at functioning levels including but not limited to poly nucleotides, such as siRNA, shRNA, anti-sense RNA, anti-sense DNA oligo, and dominant negative DNA vectors, peptide and amino acid sequences, such as peptide, and antibodies, and small molecule inhibitors. The siRNA2 sequence described above is the preferred sequence, but this does not limit from other siRNA sequences and other means as described in this paragraph. As in general the siRNA sequence can vary 10%, 20% and even 30-40% from the exact sequence of the transcript.

The term "C6orf108" [Nucleotide SEQ ID #14, Peptide SEQ ID #15] represents human C6orf108 chromosome 6 open reading frame 108 [*Homo sapiens*] GeneID: 10591. Official Symbol C6orf108. This gene was identified on the basis of its stimulation by c-Myc protein. The exact function of this gene is not known but studies in rat suggest a role in cellular proliferation and c-Myc-mediated transformation. In the present description, C6orf108 is a target for developing anticancer treatment. C6orf108 can be targeted by any means that alter its expression levels and activities at functioning levels including but not limited to poly nucleotides, such as siRNA, shRNA, anti-sense RNA, anti-sense DNA oligo, and dominant negative DNA vectors, peptide and amino acid sequences, such as peptide, and antibodies, and small molecule inhibitors.

The term "Interferon" (IFN) is a group of cytokines produced by leucocytes and fibroblasts. The IFN that are described herein includes all type I and type II IFNs and all the subtypes of IFN including, but not limited to IFNα A, IFNα B, IFNα C, IFNα D, IFNα F, IFNα G, IFNα H, IFNα I, IFNαJ, IFNα K, IFNα 4b, IFNα WA, IFNβ, IFNγ and IL-6.

The term "WST-1c" representing a water soluble tetrazolium salt WST-1 {4-[3-(4-Iodophenyl)-2-(4-nitrophenyl)-2H-5-tetrazolio]-1,3-benzenedilsulfonate} was first described by ishiyama et al in 1996 (Ishiyam M, et al *Biol Pharm Bull* 1996, 19:1515-20).

The term "WST-1r" represents a reagent mixture comprising WST-1c and mPMS at optimized concentration and the ratio between WST-1c and mPMS for the combination treatment. The optimized concentration and molar ration of the two components may not be the same as that of the commercial "cell proliferation kit"

The term "IEA" is the symbol of "Intermediate Electron Acceptor".

The term "mPMS" (1-methoxy-5-methyl-phenazinium methyl sulfate) is a chemical compound acts as an "electron coupling agent/IEA" when combined with tetrazolium salts.

The term "Q1" (coenzyme Q1, 2,3-Dimethoxy-5-methyl-6-(3-methyl-2-butenyl)-1,4-benzoquinone) is a chemical compound act as an IEA.

The term "WST" represents the collection of a class of compounds of water soluble tetrazolium salts including, but not limited to WST-3, WST-4, WST-5, WST-8, WST-9, WST-10, WST-11, XTT, and MSN. These compounds are also impermeable to cell plasma membrane.

The term "XTT" represents a water soluble tetrazolium salt in the similar class of WST-1 as well as a reagent that composed of XTT and mPMS or coenzyme Q1.

The term "CCK8" represents a cell counting kte, which is composed of WST-8 and mPMS.

The term "valid substitutes of WST-1r" represents any compounds that can substitute the function of WST-1r, WST-1c, or the electron coupling reagent mPMS or any of the remaining components either act alone or in any type of combination among these substitutes or any type of combination with any of the component of the water soluble tetrazolium salt and IEA that comprising WST-1r to function as the WST-1r as described in this specification to reproduce the synergistic induction of cancer cell death. The term "valid substitutes of WST-1r" includes, but not limited to all the up to date available tetrazolium salt based WSTs that include, but not limited to, WST-1, WST-3, WST-4, WST-5, WST-9, WST-10 AND WST-11, MTS and XTT, and an IEA, including mPMS and coenzyme Q1 and the combination of these tetrazolium salts with IEA comprising WST-1+mPMS, WST-3+mPMS, WST-4+mPMS, WST-5+mPMS, WST-9+mPMS, WST-10+mPMS, WST-11+mPMS, XTT+mPMS, MTS+mPMS, WST-3+Q1, WST-4+Q1, WST-5+Q1, WST-9+Q1, WST-10+Q1, WST-11+Q1, XTT+Q1 MTS+Q1.

The term "IKK inhibitor" refers to an agent capable of inhibiting the activity of Inhibitor kappaB kinase (IKK) and thereby inhibiting the kinase activity of IKK and its function of activating NF-kB. Therefore, inhibits NF-κB activity. An IKK inhibitor may be a competitive, noncompetitive, or irreversible IKK inhibitor. "A competitive IKK inhibitor" is a compound or a peptide that reversibly inhibits IKK enzyme activity at the catalytic site; "a noncompetitive IKK Inhibitor" is a compound that reversibly inhibits IKK enzyme activity at a non-catalytic site; and "an irreversible IKK inhibitor" is a compound that irreversibly destroys IKK enzyme activity by forming a covalent bond with the enzyme. The term "IKK inhibitors" include, without limitation, i) compounds previously established to exhibit IKK inhibitory properties including, but not limited to: SPC839 (Signal Pharmaceutical Inc.), Anilino-Pyrimidine Derivative(Signal Pharmaceutical Inc.), PS1145(Millennium Pharmaceutical Inc.), BMS-345541* (Bristol-Myers Squibb Pharmaceutical Research Institute, IKK inhibitor III), SC-514*(Smithkilne Beecham Corp.), Amino-imidazolecarboxamide derivative(Smithkilne Beecham Corp.), Ureudo-thiophenecarboxamide derivatives(AstraZeneca), Diarylpybidine derivative(Bayer), Pyridooxazinone derivative(Bayer), Indolecarboxamide derivative (Aventis Pharma), Benzoimidazole carboxamide derivative (Aventis Pharma), Pyrazolo[4,3-c]quinoline derivative (Pharmacia Corporation), Imidazolylquinoline-carbxaldehyde semicarbazide derivative(Tulark Inc.), Pyridyl Cyanoguanidine derivate(Leo Pharma), IkB Kinase Inhibitor Peptide(CalBiochem), IKK-2 Inhibitor IV [5-(p-Fluorophenyl)-2-ureido]thiophene-3-carboxamide(CalBiochem), IKK Inhibitor II, Wedelolactone(CalBiochem), IKK Inhibitor VII (CalBiochem), IKK-2 Inhibitor V N-(3,5-Bis-trifluoromethylphenyl)-5-chloro-2-hydroxybenzamide IMD-0354(CalBiochem), IKK-2 Inhibitor VI (5-Phenyl-2-ureido)thiophene-3-carboxamide(CalBiochem), IKK-2 Inhibitor VIII ACHP 2-Amino-6-(2-(cyclopropylmethoxy)-6-hydroxyphenyl)-4-(4-piperidinyl)-3-pyridinecarbonitrile (CalBiochem). ii) In a certain embodiment, the group of IKK inhibitors may additionally include compounds discovered to have IKK inhibitory activity, in accordance with the present specification, and previously identified to have anti-tumor activity, including, but not limited to PS1145(Millennium Pharmaceutical Inc.), BMS-345541*(Bristol-Myers Squibb Pharmaceutical Research Institute).

The term "CK2 inhibitor" represents all protein kinase casein kinase2 inhibitors. The preferred CK2 inhibitors is, but not limited to Apigenin.

The term "Apigenin" CAS Registry Number: 520-36-5, Chemical Abstracts Service Name: 4H-1-benzopyran-4-one, 5,7-dihydroxy-2-(4-hydroxy-phenyl)-(9CI). It is also named as Apigenine; Chamomile; Apigenol; Spigenin; and Versulin and is a member of Flavones, a subclass of flavonoids. Apigenin is a multi function signal transductor modulator that reduces DNA oxidative damage; inhibit the growth of human leukemia cells and induced these cells to differentiate; inhibit cancer cell signal transduction and induce apoptosis; act as an anti-inflammatory; and as an anti-spasmodic or spasmolytic. Apigenin inhibits activity of NF-κB, IKK-1 and IKK-2, protein kinase 2 (CK2), mape kinase (MPK), hypoxia inducing factor 1(HIF), vescular epithelium growth factor (VEGF) and some other molecules and regulatory pathways such as cell cycle and angiogenesis, induce p53 activity, maintaining genomic stability by holding cell cycle for mismatch repair or arrest cell cycle and induce apoptosis etc. Apigenin is know to have the effects of anti-UV radiation caused oxidation, and chemoprevention for cancer. The apigenin, herein, is also described as a representative of the subclasses of flavonoids, the flavones including, but not limited to: tricin, luteolin, tangeritin, 6-hydroxyflavone, Baicalein, Scutellarein, Wogonin, Diosmin, Flavoxate, Chrysin, the glycosided forms of these flavones, and other subclasses of the flavonoids with similar biological activities include, but not limited to Isoflavones, Flavonols, Flavanones, 3-Hydroxyflavanones, Flavan-3-ols, Anthocyanidins, 3-deoxyanthocyanidin, Anthocyanins, Acetylated and glycosides, and Tannins, as well as isoflavonoids and neoflavonoids.

The term "Flavonoids" also called bioflavonoids also collectively know as Vitamin P and citrin, are a class of plant secondary metabolites. Herein flavonoids represent all of the three ketone-containing compounds (flavonoid and flavonols) according to IUPAC nomenclature classifications: i) the flavonoids derived from 2-phenylchromen-4-one (2-phenyl-1,4-benzopyrone) structure; ii) isoflavonoids, derived from 3-phenylchromen-4-one (3-phenyl-1,4-benzopyrone) structure; and iii) neoflavonoids, derived from 4-phenylcoumarine (4-phenyl-1,2-benzopyrone) structure; as well as the non-ketone polyhydroxy polyphenol compounds including: flavanoids, flavan-3-ols and catechins. Sample compounds include, but not limited to Isoflavone:Biochanin A, Daidzein, Daidzin, Formononetin, Genistein, Coumestrol, Puerarin; flavan-3-ols: catechins (catechin, epicatechin (EG), epicatechin, gallate (EGC), and epigallocatechin gallate (EGCG)); flavonol: myricetin, quercetin, and Kaempferol; Isoflavenes: phenoxodiol; Anthocyanins: Antirrhinin, Chrysanthenin, Malvin, Myrtillin, Oenin Primulin, Protocyanin, Tulipanin; 3-deoxyanthocyanidin: Apigeninidin, Columnidin, Diosmetinidin, Luteolinidin, Tricetinidin; Anthocyanidins: Aurantinidin, Cyanidin, Delphinidin, Europinidin, Luteolinidin, Malvidin, Pelargonidin, Peonidin, Petunidin, Rosinidin; 3-Hydroxyflavanones: Dihydrokaempferol, Dihydroquercetin; Flavanones: Eriodictyol, Hesperetin, Homoeriodictyol, Naringenin; Flavonols: Fisetin, Isorhamnetin, Kaempferol, Myricetin, Pachypodol, Quercetin, Rhamnazin, Morin; and their glycoside forms.

The term "HIF" hypoxia inducible factor represents a family of transcription factors that response to decrease of available oxygen or hypoxia in the cellular environment. Three family members have been identified. They are HIF-1 (a dimmer composed of HIF-1α and HIF-1β), HIF-2 (a dimmer composed of HIF-2α and HIF-2β), HIF-3 (a dimmer composed of HIF-3α and HIF-3β).

The term "HIF inhibitors" are the biological and non-biological compounds that inhibit HIFs and/or cellular responses to hypoxia, including, but not limited to: 2,2-dimethybenzopyran compounds, chetomin, 2-methoxyestradiol (2ME2), PX-478, 17-N-allylamino-17-demethoxygeldanamycin (17-AAG), EZN-2968, camptothecins, NSC 644221, 3-(5'-hydroxymethyl-2'-furyl)-1-benzylindazole (YC-1), rapamycin, and decoy oligonucleotides against HIF-1 RX-0047.

The term "tNOX' represents a tumor specific cell surface NADH oxidase. It is also called ECTO2.

The term "tNOX inhibitors" represents the compounds that are capable of inhibiting the tNOX activity. The tNOX inhibits, herein, includes, but not limited, catechins: catechin, epicatechin (EG), epicatechin gallate (EGC), and epigallocatechin gallate (EGCG); and a isoflavenes analogue derivative, the phenoxodiol.

The term "Oxidative Phosphorylation" is a process that coupling the oxidation of the protons with the synthesis of ATP, which transfer and store the energy derived from glucose metabolism to the ATP as cellular energy source.

The term "Uncoupler" means to uncouple the cellular oxidative phosphrylation process that blocks the ATP synthesis, the energy metabolism in the cell. The known unucouplers including, but not limited to: dinitrophenol (DNP), Carbonyl cyanide m-chlorophenyl hydrazone (CCCP), Carbonyl cyanide-p-trifluoromethoxyphenylhydrazone (FCCP), Hindered pheniil (SF6847), Salicylanilide S-13, PCP, TTFB, and alpha-(phenylhydrazono)phenylacetonitrile derivatives.

The term "LiCl" is an inorganic salt, lithedium Chloride, and is used as an inhibitor of GSK3β. LiCl, herein, represents the class of inhibitors that inhibit GSK3β.

The term "IKK" represents Inhibitory kappaB Kinase, which phosphorylate IκB that leads to NF-KAPPAB activation. Two IKK isoforms have been identified. They are IKK1 (IKKα) and IKK2 (IKKβ). The term "NF-kappaB" Nuclear factor kappaB is a family of rel proteins that act as transcription factors regulating gene expression. Normally NF-KAPPAB proteins forms a dimmer which also complex with an inhibitory kappa B (IκB) molecule stay in inactive form in the cytoplasm. Upon signal activation, the IκB is phosphorylated by IKK and dissociate from the NF-kappaB dimmer, which release the NF-KAPPAB to entering the nuclear for activating transcription of a special set of genes that are regulated by NF-KAPPAB. The dissociated IκB will be degraded by protesomes. Activation of NF-kappaB favors cell proliferation and survival. NF-kappaB activity has been found to associate with and contribute to carcinogenesis process, tumor progression and resistance of cancer cells to chemo and radiation therapies.

The term "C-Jun N-terminal kinases" (JNKs), originally identified as kinases that bind and phosphorylate c-Jun on Ser63 and Ser73 within its transcriptional activation domain, are mitogen-activated protein kinases which are responsive to stress stimuli, such as cytokines, ultraviolet irradiation, heat shock, and osmotic shock, and are involved in T cell differentiation and apoptosis.

The term "Reactive Oxygen Species" (ROS) includes oxygen ions, free radicals and peroxides both inorganic and organic. They are generally very small molecules and are highly reactive due to the presence of unpaired valence shell electrons. ROSs form as a natural byproduct of the normal metabolism of oxygen and have important roles in cell signaling. The effects of ROS on cell metabolism have been well documented in a variety of species. These include not only roles in programmed cell death and apoptosis, but also positive effects such as the induction of host defence genes and mobilisation of ion transport systems. This is implicating them more frequently with roles in redox signaling or oxidative signaling.

The term "Cancer Cells" represents the cells in culture that were derived from human cancer or tumors, which have malignant features, such as lost of contact inhibition.

The term "Cancer" describes a diseased state in which a carcinogenic agent or agents causes the transformation of a normal cell into an abnormal cell, the invasion of adjacent tissues by these abnormal cells, and lymphatic or blood-borne spread of malignant cells to regional lymph nodes and to distant sites, i.e., metastasis.

The term "Effective dose" As used herein, the term "effective dose" means that amount of a drug or pharmaceutical agent that will elicit the biological or medical response of a cell, tissue, system, animal or human that is being sought, for instance, by a researcher or clinician.

The term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The term "Treatment of cancer" describes the drug or reagents administrated to the cells or to a mammal, the duration of the treatment, the method used to administrate these drugs, or reagents and the order and intervals of between these treatments.

The term "Synergistic effect/Synergize" refers to a combination of two or more treatments, which is more effective to produce advantageous results than the additive effects of these agents.

The term "Chemotherapy Drugs (Agent)" refers to any drugs that have cytrotoxic effect on cancer cells and are currently used as a drug for treating cancer. The drugs that were tested in this specification are listed as the following. Chemotherapy Drugs that we are mentioned in this specification were not limit to this list.

The term "5-fluorouracil",5-fluoro-2,4-(1H,3H) pyrimidinedione(5-FU), is commercially available as fluorouracil.

The term "Cis-Platinum" cis-diamminedichloroplatinum, is commercially available as PLATINOL® as an injectable solution.

The term "Paclitaxel" is a potent anti-neoplastic drug; binds to the N-terminal region of β-tubulin and promotes the formation of highly stable microtubules that resist depolymerization, thus preventing normal cell division and arresting the cell cycle at the $G_2$/M phase.

The term "Doxorubicin", (8S,10S)-10-[(3-amino-2,3,6-trideoxy-.alpha.-L-lyxo-hexopyranosyl)oxy]-8-glycoloyl,7,8,9,10-tetrahydro-6,8,11-trihydroxy-1-methoxy-5,12 naphthacenedione hydrochloride, is commercially available as an injectable form as RUBEX® or ADRIAMYCIN RDF®.

The term a "therapeutically effective amount" of a compound or a pharmaceutical composition refers to an amount sufficient to modulate cancer cell proliferation in culture, tumor growth or metastasis in an animal, especially a human, including without limitation decreasing tumor growth or size or preventing formation of tumor growth in an animal. This term may also mean the effective amount(s) needed to cause cancer cell death or selective cancer cell death while not causing side effects in normal cells.

The term "Pharmaceutically acceptable" indicates approval by a regulatory agency of the Federal or a state government or listed in the U.S. Pharmacopeia or other generally recognized pharmacopoeia for use in animals, and more particularly in humans.

The term a "carrier" refers to, for example, a diluent, adjuvant, excipient, auxilliary agent or vehicle with which an active agent of the present specification is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin. It also include the transfection reagents as used for deliver of DNA and/or RNA into cells either in vitro or in vivo.

The term "Concurrently" means (1) simultaneously in time, or (2) at different times during the course of a common treatment schedule.

The term "Sequentially" refers to the administration of one active agent used in the method followed by administration of another active agent. After administration of one active agent, the next active agent can be administered substantially immediately after the first, or the next active agent can be administered after an effective time period after the first active agent; the effective time period is the amount of time given for realization of maximum benefit from the administration of the first active agent.

III Targets and Targeting the Therapeutic Targets for the Treatment of Cancer

This description provides nucleotide sequences for genes that implicate and/or can be utilized as therapeutic targets for the treatment of cancer, and polypeptides encoded by such sequences and antibodies and compounds reactive with such polypeptides in methods of treating a cancer, and for agents effective in reducing the activity of cancer-linked genes and thereby treating a cancerous condition which were not previously established for anti-tumor effect(s).

The disclosed nucleotide sequences are related to and derived from a DNA cloning vector, pUC19 (SEQ ID #1), which was discovered to synergize IKK inhibition, inhibit cancer cell growth proliferation and promote cancer cell death when transfection of this vector to cancer cells was combined with or without IKK inhibitor treatment and followed by WST-1r or any of its valid substitutes treatment or in combination with chemotherapeutic drugs. This function of pUC19 has not been previously reported. Other potential DNA sequence may also include a pcDNA3 version 3.1, (SEQ ID 13) and the attached blast result entitled: "NCBI Blast_pcDNA3 Nucleotide sequence (5448 letters)".

Accordingly, the discovery that the anti-cancer effect of pUC19 vector (SEQ ID #1) was primarily resides in its DNA sequences that are mapped to transcripts and/or short sequences (from 15 bp up to 100 bp) that flanking the genes in human genome. The human transcripts that pUC19 DNA sequences mapped to are, but not limited to, (1) Homo sapiens transient receptor potential cation channel, subfamily C, member 6 (TRPC6, GeneID: 7225, mRNA: NM_004621.3, SEQ ID #2, #6), (2) Homo sapiens SH3 and PX domains 2B (SH3PXD2B, GeneID: 285590, mRNA:NM_001017995, SeQ ID #3, #7), (3) Homo sapiens membrane associated guanylate kinase, WW and PDZ domain containing 3 (MAG-IKK, GeneID: 260425, transcript variant 2, mRNA:NM_152900, SeQ ID #4, #8), (4) the Homo sapiens trans-membrane protein 182 (TMEM182, GeneID: 130827, mRNA: NM_144632, SeQ ID #5, #9) and (5) Homo sapiens chromosome 6 open reading frame 108 C6orf108, GeneID: 10591 SeQID #14, #15). The human genome sequences that pUC19 DNA sequences mapped to are listed in the attached file "NCBI Blast-pUC19-Human-Transcripts and genome(2686 letters)", "NCBI Blast_siRNA2 Nucleotide sequence (24 letters)" and "NCBI Blast_pcDNA3 Nucleotide sequence (5448 letters)".

The polynucleotide disclosed herein incorporate various polynucleotide transcripts (SEQ ID NO: 2, 3, 4, 5 and 14) and, thus, derived amino acid sequence (SEQ ID NO: 6, 7, 8, 9 and 15) from said transcripts are available as targets for treatment of cancer, especially anti-cancer agents, including, with no limitation, peptide and proteins, such as antibodies specific against said polypeptides, peptide inhibitors, small molecule inhibitor, polynucleotides, such as siRNAs, shRNA, anti-sense RNA, anti-sense oligo and dominant negative DNA vectors. In a particular embodiment the wherein said double strand siRNAs are, but not limited to, siRNA1 (SEQ ID #10), siRNA2 (SEQ ID #11), siRNA3 (SEQ ID #12).

The polynucleotides and polypeptides, as gene products, used in the processes may comprise a recombinant polynucleotide or polypeptide, a natural polynucleotide or polypeptide, or a synthetic polynucleotide or polypeptide, or a chemically modified polynucleotide or polypeptide.

The nucleotides and polypeptides of the pUC19 vector, that are mapped to the human genome, flanking genes in the human genome used in the processes of the present description may comprise a recombinant polynucleotide or polypeptide, a natural polynucleotide or polypeptide, or a synthetic polynucleotide or polypeptide.

Fragments of such polynucleotide and polypeptides as are disclosed herein may also be useful in practicing the processes of the present specification. For example, a fragment, derivative or analog of the polynucleotide (SEQ ID# 2, 3, 4, 5 and 14) may be substituted by (i) any part of these sequences and/or with mismatches for up to 40% of the total sequences been used for, (ii) fused into a DNA vector or any type of carriers, (iii) nucleotide sequences with modified nucleotides.

Fragments of such polynucleotides and polypeptides as are disclosed herein may also be useful in practicing the processes of the present specification. For example, a fragment, derivative or analog of the polypeptide (SEQ ID NO: 6, 7, 8, 9 and 15) may be (i) one in which one or more of the amino acid residues are substituted with a conserved or non-conserved amino acid residue (more preferably a conserved amino acid residue) and such substituted amino acid residue may or may not be one encoded by the genetic code, or (ii) one in which one or more of the amino acid residues includes a substitute group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretor sequence or a sequence which is employed for purification of the mature polypeptide (such as a histidine hexapeptide) or a proprotein sequence. Such fragments, derivatives and analogs are deemed to be within the scope of those skilled in the art from the teachings herein.

Substituting these siRNAs (SEQ ID 10, 11, 12) as disclosed herein above may also be useful in practicing the processes of the present specification. Examples may include, but not limited to, (i) a siRNA that mapped to another part of the sequence of the coding sequence of the gene, (ii) variations of the siRNA sequences that still capable to target the same gene and reduce it expression level, (iii) any type of modifications of the siRNA either at the nucleotides or the whole siRNA, (iv) put the siRNA sequence into any type of carriers, such as a vector or a chemical for the delivery of the sequence.

The nucleotide sequence of the complete mRNA and open reading frame of the transcripts and amino acid sequences, as discussed above, can be found in the NCBI GenBank database with the Gene ID or accession numbers listed above.

The pharmaceutical compositions and the medical use as described are based, at least in part, on the discovery of inhibitory effect of pUC19 vector in cancer cell growth and proliferation and inducing cancer cell death when combined with IKK inhibitor WST-1r treatment as well as in combination with chemotherapeutic drugs to treat cancer cells. This inhibitory effect of pUC19 DNA transfection may be substituted by siRNA, compounds or small molecule inhibitor, peptide inhibitor, antibody, shRNA, anti-sense RNA, anti-sense oligo, and antibody and dominant negative DNA vectors targeting the gene to alter its expression level, the corresponding transcripts and/or protein as described above in this section and at least in partial by IFN.

Cancers that may be treated using the present discovery include, but are not limited to: cancers of the prostate, colorectum, pancreas, cervix, stomach, endometrium, brain, liver, bladder, ovary, testis, head, neck, skin (including melanoma and basal carcinoma), mesothelial lining, esophagus, breast, lung (including small-cell lung carcinoma and non-small-cell carcinoma), adrenal gland, thyroid, kidney, glioblastoma, mesothelioma, renal cell carcinoma, gastric carcinoma, choriocarcinoma, cutaneous basocellular carcinoma, and testicular seminoma, sarcoma of muscle, connective tissue or bone and leukemia.

IV. Pharmaceutical Compositions and Methods for Cancer Therapy

1. Inhibition of tPMET and Cell Surface Respiration in Combination with Inhibition of HIF as a Strategy for Synergizing Cancer Cell Death as a Cancer Treatment A living cell relies on energy. Unlike normal cells that consume oxygen and generate ATP in mitochondrial, cancer cells consume oxygen on cell surface through tPMET. This cellular geographic difference between cancer cells and normal cells makes the PMET a unique site for cancer specific targeting. In addition, cancer cells are resistant to hypoxia due to increased levels and activities of hypoxia inducible factor (HIF). Therefore, blocking the PMET while inhibiting the HIF will induce synergistic and cancer specific cell death for treating cancer in a cancer patient.

One embodiment of the present invention provides pharmaceutical compositions comprising (1) a compound that is impermeable to cell plasma membrane and is capable of interfering, and/or blocking tMPET and/or cell surface respiration, such as WST-1r, WST-3 or their valid substitute, in combination with (2) the second compound that is capable of suppressing cellular survival signaling, such as NF-κB activities, and/or cellular responses to hypoxia, such as apigenin or its valid substitute, HIF inhibitors, IKK inhibitors, flavonoids and pUC19 and its valid substitutes. Such a pharmaceutical composition may be administered, in a therapeutically effective amount, in optimized concentrations in pharmaceutical acceptable medium, to a patient in need for the treatment of cancer.

The first compound that, is composed of two functional chemical groups: A) an functional group that is capable of binding to and/or interfering and/or blocking the electron transport process of the tPMET systems, blocking the coupling of oxidative phosphorylation, and/or inhibiting the tNOX, therefore, to block cell surface respiration and oxygen consumption; and B) another chemical group or a combination of chemical groups that make(s) the entire compound impermeable to cell plasma membrane and capable of blocking the said compound penetrating the cell plasma membrane and entering the cell. By integrating these functional groups into single molecule, the said compound is capable of interfering, inhibiting and/or blocking the tPMET, or the oxidative phosphorylation process or the coupling of the oxidative phosphorylation and cell surface respiration specifically on cell surface, but not affecting the mitochondrial respiration in normal cells.

WST-3 represents such a class of the first compound. It contains a dinitrophenol functional group and a chemical group that is impermeable to cell plasma membrane.

FIG. 1 diagrams the chemical structure of WST-3 (Japanese patent JP,2592436,B, 1995), which is composed with a 2,4-Dinitrophenol (DNP), chemical structure as the said functional chemical group and a [1,3-benzenedilsulfonate] and a [4-Iodophenyl] to enhance its hydrophilic feature.

The DNP is an oxidative phosphorylation uncoupler by dissolving in the inner membrane of mitochondria and forms a protonophore, which caused the protons across the mitochondrial membrane, leading to a rapid consumption of energy without generating ATP. By integrating the said DNP with the said second group, the cell plasma impermeable group, it keeps the DNP from entering the cell, but can only act on the cell plasma membrane. As cancer cells respiration mainly rely on cell surface, the WST-3 will only blocks the cell surface respiration of cancer cells, but, will not affect the oxidative phosphorylation in mitochondrial from normal cells, hence, the treatment will be cancer specific.

The DNP as the said first functional chemical group represents an uncoupler of oxidative phosphorylatoin and may also implicate other ways of blocking tPMET and cell surface respiration. Accordingly, the said DNP can be substituted by 1) the compounds of oxidative-phsphorylation decoupling agents comprising: carbonyl cyanide m-chloro phenyl hydrazone (CCCP) and Carbonyl cyanide p-[rifluoromethoxyl]-phenyl-hydrozone (FCCP), SF 6847, salicylanilide S-13, and alpha-(phenylhydrazono)phenylacetonitrile derivatives; and 2) intermediate electron acceptor that direct interact with tPMET, including with no limitation: mPMS and coenzyme Q1; 3) tPMET substrates, such as NADH; 4) the cyanic group (C≡N), such as ferricyanide, and respiration inhibitors.

The chemical structure of the said second chemical group or combination of groups that keeps the compound impermeable to cell plasma membrane can be designed and/or produced by a skilled person in the field. Examples include, but not limited to the chemical groups that were used for modifying the tetrazolium to form the WSTs, such as the chemical structures of the WST-1, WST-3, WST-4, WST-5, WST-8, WST-9, WST-10, WXST-11, XTT, MSN that keep the compound impermeable to the cell plasma membrane.

Accordingly, the said the first compound is selected from the available groups comprising 1) cell plasma membrane impermeable uncoupler WST-3, 2) tPMET and/or tNOX inhibitors, including, but not limited to capsaicin, capsicin pepper vanilloid, green tea catechin, epigallocatechin-3-gallate; 3) the reagents that interfere tPMET activities including WST-1r and its valid substitutes including but not limited to WST-3+mPM, WST-4+mPMS, WST-5+mPMS, WST-9+mPMS, WST-10+mPMS, WST-11+mPMS, XTT+mPMS, MSN+mPMS, WST-3+Coenzyme Q1, WST-4+Coenzyme Q1, WST-5+Coenzyme Q1, WST-9+Coenzyme Q1, WST-10+Coenzyme Q1, WST-11+Coenzyme Q1, XTT+Coenzyme Q1, and MSN+Coenzyme Q1; 4) the compounds that include at least one of the functional groups as described above and are impermeable to cell plasma membrane that can be designed and produced by a skilled person in the field.

The said second compound is the one that inhibits cell hepoxia responses, which when combined with the first compound, results in synergistic cell death, such as apigenin. The said second compound is selected from the groups comprising 1)HIF inhibitors, 2) the flavonoids and its subclasses such as flavorones, 3inhibitors that inhibit NF-κB activities, such including, but no limited to IKK inhibitors, 4) plasmid DNA pUC19 [SEQ ID No:1] and its valid substitutes including, but not limited to at least one of the siRNAs derived from [SEQ ID No: 10, 11, 12], means to targeting the genes [SEQ ID No: 2, 3, 4, 5, 14]and their corresponding gene products [SEQ ID No: 6, 7, 8, 9, 15] to alter their expression levels and functional activities including, but not limited to nucleotide sequences including dominant negative DNA that block the function of the corresponding gene products, siRNA, antisnese RNA, antisense oligo, peptides, peptide inhibitors, antibodies, small molecule inhibitors.

The said apigenin is a flavone, a subclass of flavonoids, and is a multi-function signal transduction modulator and/or inhibitor to cells. Its function includes, but not limited to induction of p53 activation, suspend cell cycle progression for maintaining genomic stability, inhibiting expression and/or activities of hypoxia induced factor-1 (HIF-1), casein kinase II, NF-κB, IKK and induction of generation of reactive oxygen species (ROS) and more.

The second compound and the valid substitutes of apigenin is selected from the groups comprising (1) At least one flavones, include, but not limited to nature existed flavones, such as: tricin, Luteolin, Tangeritin, Chrysin, 6-hydroxyflavone, Baicalein, Scutellarein, Wogonin and synthetic flavones, such as: Diosmin, Flavoxate, additional subgroups of flavones: flavonols, flavannones, flacanonols, catechins, isoflavones; or (2) at least one from other subgroups of Flavonoid (Bioflavonoids) and their isoforms including naturally existed, artificial modified ketone isoforms and synthetic compounds including, but not limited to flavonoids, derived from 2-phenylchromen-4-one (2-phenyl-1,4-benzopyrone) structure (examples: quercetin, rutin); isoflavonoids, derived from 3-phenylchromen-4-one (3-phenyl-1,4-benzopyrone) structure; neoflavonoids, derived from 4-phenylcoumarine (4-phenyl-1,2-benzopyrone) structure, and flavanoids as a non-ketonepolyhydroxy polyphenol compounds, including: flavanoids, flavan-3-ols and catechins. Sample compounds include, but not limited to Isoflavone:Biochanin A, Daidzein, Daidzin, Formononetin, Genistein, Coumestrol, Puerarin; flavan-3-ols: catechins (catechin, epicatechin (EG), epicatechin, gallate (EGC), and epigallocatechin gallate (EGCG)); flavonol: myricetin, quercetin, and Kaempferol; Isoflavenes: phenoxodiol; Anthocyanins: Antirrhinin, Chrysanthenin, Malvin, Myrtillin, Oenin Primulin, Protocyanin, Tulipanin; 3-deoxyanthocyanidin: Apigeninidin, Columnidin, Diosmetinidin, Luteolinidin, Tricetinidin; Anthocyanidins: Aurantinidin, Cyanidin, Delphinidin, Europinidin, Luteolinidin, Malvidin, Pelargonidin, Peonidin, Petunidin, Rosinidin; 3-Hydroxyflavanones: Dihydrokaempferol, Dihydroquercetin; Flavanones: Eriodictyol, Hesperetin, Homoeriodictyol, Naringenin; Flavonols: Fisetin, Isorhamnetin, Kaempferol, Myricetin, Pachypodol, Quercetin, Rhamnazin, Morin; and their glycoside forms; or (3) At least one HIF inhibitors and/or inhibition of cellular responses to hypoxia including, but not limited to: 2,2-dimethybenzopyran compounds, chetomin, 2-methoxyestradiol (2ME2), PX-478, 17-N-allylamino-17-demethoxygeldanamycin (17-AAG), EZN-2968, camptothecins, NSC 644221, 3-(5'-hydroxymethyl-2'-furyl)-1-benzylindazole (YC-1), rapamycin, and decoy oligonucleotides against HIF-1 RX-0047; or (4) IKK inhibitors are as listed above and following embodiments include compounds which exhibits IKK inhibitory activity in pharmaceutically acceptable medium. The at least one IKK inhibitor may be selected from compounds of the group consisting of, without limitation, i) compounds previously established to exhibit IKK inhibitory properties including, but not limited to: SPC839 (Signal Pharmaceutical Inc.), Anilino-Pyrimidine Derivative(Signal Pharmaceutical Inc.), PS1145(Millennium Pharmaceutical Inc.), BMS-345541*(IKK inhibitor III, Bristol-Myers Squibb Pharmaceutical Research Institute), SC-514*(Smithkilne Beecham Corp.), Amino-imidazolecarboxamide derivative(Smithkilne Beecham Corp.), Ureudo-thiophenecarboxamide derivatives (AstraZeneca), Diarylpybidine derivative(Bayer), Pyridooxazinone derivative(Bayer), Indolecarboxamide derivative (Aventis Pharma), Benzoimidazole carboxamide derivative (Aventis Pharma), Pyrazolo[4,3-c]quinoline derivative (Pharmacia Corporation), Imidazolylquinoline-carbxaldehyde semicarbazide derivative(Tulark Inc.), Pyridyl Cyanoguanidine derivate(Leo Pharma), IκB Kinase Inhibitor Peptide(CalBiochem), IKK-2 Inhibitor IV [5-(p-Fluorophenyl)-2-ureido]thiophene-3-carboxamide(CalBiochem), IKK Inhibitor II (Wedelolactone(CalBiochem), IKK Inhibitor VII (CalBiochem), IKK-2 Inhibitor V (N-(3,5-Bistrifluoromethylphenyl)-5-chloro-2-hydroxybenzamide IMD-0354, CalBiochem), IKK-2 Inhibitor VI (5-Phenyl-2-ureido)thiophene-3-carboxamide, CalBiochem), IKK-2 Inhibitor VIII (ACHP 2-Amino-6-(2-(cyclopropylmethoxy)-6-hydroxyphenyl)-4-(4-piperidinyl)-3-pyridinecarbonitrile, CalBiochem). ii) In a certain embodiment, the group of IKK inhibitors may additionally include compounds discovered to have IKK inhibitory activity, in accordance, and previously identified as anti-tumor agents, including, but not limited to PS1145(Millennium Pharmaceutical Inc.), BMS-345541* (IKK inhibitor III, Bristol-Myers Squibb Pharmaceutical Research Institute); or (5) at least one nucleotide sequences [SEQ ID NO:1, 10, 11, 12, 13], and means for targeting the genes of polynucleotide sequences [SEQ ID No: 2, 3, 4, 5, 14] and peptide sequences [SEQ ID No: 6, 7, 8, 9, 15] to inhibit the expression levels and functional activities of the corresponding genes by siRNA, antisense RNA, antisense oligo, dominant negative DNA, peptide, peptide inhibitors, antibodies, small molecule inhibitors.

2. Pharmaceutical Composition and Method of WST-3 and Apigenin Combination Treatment for Cancer Therapy One of the best mode embodiment of the present invention provides pharmaceutical compositions comprising (1) at least one Water-soluble tetrazolium salts 3 (WST-3,2-(4-Iodophenyl)-3-(2,4-dinitrophenyl)-5-(2,4-disulfophenyl)-2H-tetrazolium, sodium salt, FIG. 1A) or its valid substitutes in combination with (2) at least one apigenin or its valid substitutes. Such a pharmaceutical composition may be administered, in a therapeutically effective amount, in optimized concentration in pharmaceutical acceptable medium, to a patient in need for the treatment of cancer.

WST-3 is a water soluble tetrazoliums (WST) that were developed by Dojindo Inc., whose WSTs have sulfate groups added directly or indirectly to the phenyl ring to improve water-solubility that also makes the compound impermeable to cell plasma membrane. Different from all other WSTs, WST-3 contains a 2,4-dinitrophenol (DNP) group directly linked to the tetrazolium ring (FIG. 1).

DNP, a cellular metabolic poison, represents a class of six manufactured chemical compounds that can dissolve in the mitochondria membrane, acts as a proton ionophore, an agent that can shuttle protons (hydrogen ions) across biological membranes, where it uncouples oxidative phosphorylation by carrying protons across the mitochondrial membrane, leading to a rapid consumption of energy without generating ATP. DNP defeats the proton gradient across mitochondria and chloroplast membranes, collapsing the proton motive force that the cell uses to produce most of its ATP chemical energy. Instead of producing ATP, the energy of the proton gradient is lost as heat. Cells counteract the lowered yields of ATP by oxidizing more stored reserves such as carbohydrates and fat. DNP has been used as weight loss treatment for burning extra fats. However, it is toxic to the cells by exoughsting cell energy sources.

General structure feature of uncouplers are weak acids comprising the chemical groups: Weakly Acidic Phenols, benzimidazoles, N-phenylanthranilates, salicylanilides, phenylhydrazones, salicylic acids, acyldi-thiocarbazates, cumarines, and aromatic amines.

The chemical structures of representative weakly acidic uncouplers that are capable of substituting the DNP are selected from the groups comprising: 5-chloro-3-tert-butyl-2'-chloro-4'-nitrosalicylanilide (S-13), sodium 2,3,4,5,6-pentachlorophenolate (PCP), 4,5,6,7-tetrachloro-2-(trifluoromethyl)-1H-benzimidazole (TTFB), Flufenamic acid (2-[3-(trifluoromethyl)anilino]benzoic acid), 3,5-di-tert-butyl-4-hydroxy-benzylidenemalononitrile (SF6847), carbonyl cyanide m-chloro phenyl hydrazone (CCCP) and Carbonyl cyanide p-[trifluoromethoxy]-phenyl-hydrazone (FCCP), and alpha-(phenylhydrazono)phenylacetonitrile derivatives.

The incorporating DNP into the water soluble tetrozolium salts that keeps the WST-3 impermeable to cell plasma membrane, hence, makes WST3 capable of mimicking the DNP effect to act on cell plasma membrane for uncoupling oxidative phosphorylation that interrupts tPMET, but does not affect mitochondria in normal cells (FIG. 1).

Thus, WST-3 represents classes of compounds that comprises of (1) an active group that is capable of blocking tPMET and/or oxidative phosphorylation and/or the coupling process between these two processes and (2) the chemical structure that keeps the compound impermeable to cell plasma membrane. In this way such a compound shall be able to specifically block the tPMET electron transfer and/or oxidative phosphorylation of ADP on cell surface, hence, specifically inhibit tPMET and ATP production in cancer cells.

The valid substitutes of WST-3 include, but not limited to the compounds that contains the combination of the two said features including (1) the active group as described above that can block the tPMET and/or oxidative phosphorylation and/or the coupling of the tPMET and the oxidative phosphorylation process (2) the chemical structure that makes the resulting compound impermeable to cell plasma membrane as described above for the first compound as described.

The said Apigenin is a flavonoid and is a multi-function inhibitor to cells. Its function includes, but not limited to induction of p53 activation, suspend cell cycle progression to maintain genomic stability, inhibiting expression and/or activities of hypoxia induced factor-1 (HIF-1), casein kinase II, NF-κB, induction of generation of ROS and more.

The valid substitutes of apigeninare are selected from the groups comprising: at least one flavones, include, but not limited to nature existed flavones, such as: Tricin, Luteolin, Tangeritin, Chrysin, 6-hydroxyflavone, Baicalein, Scutellarein, Wogonin and synthetic flavones, such as: Diosmin, Flavoxate, additional subgroups of flavones: flavonols, flavannones, flacanonols, catechins, isoflavones; at least one from other subgroups of Flavonoid or Bioflavonoids and their isoforms including naturally existed, artificial modified isoforms and synthetic compounds including, but not limited to flavonoids, derived from 2-phenylchromen-4-one (2-phenyl-1,4-benzopyrone) structure (examples: quercetin, rutin); isoflavonoids, derived from 3-phenylchromen-4-one (3-phenyl-1,4-benzopyrone) structure; neoflavonoids, derived from 4-phenylcoumarine (4-phenyl-1,2-benzopyrone) structure, and flavanoids as a non-ketonepolyhydroxy polyphenol compounds as described at least one HIF inhibitors and/or inhibition of cellular responses to hypoxia including, but not limited to: 2,2-dimethybenzopyran compounds, chetomin, 2-methoxyestradiol (2ME2), PX-478, 17-N-allylamino-17-demethoxygeldanamycin (17-AAG), EZN-2968, camptothecins, NSC 644221, 3-(5'-hydroxymethyl-2'-furyl)-1-benzylindazole (YC-1), rapamycin, and decoy oligonucleotides against HIF-1 RX-0047.

IKK inhibitors are as listed above and following embodiments include compounds which exhibits IKK inhibitory activity in pharmaceutically acceptable medium. The at least one IKK inhibitor may be selected from compounds of the group consisting of, without limitation, i) compounds previously established to exhibit IKK inhibitory properties including, but not limited to: SPC839 (Signal Pharmaceutical Inc.), Anilino-Pyrimidine Derivative(Signal Pharmaceutical Inc.), PS1145(Millennium Pharmaceutical Inc.), BMS-345541* (IKK inhibitor III, Bristol-Myers Squibb Pharmaceutical Research Institute), SC-514*(Smithkline Beecham Corp.), Amino-imidazolecarboxamide derivative(Smithkline Beecham Corp.), Ureudo-thiophenecarboxamide derivatives(AstraZeneca), Diarylpybidine derivative(Bayer), Pyridooxazinone derivative(Bayer), Indolecarboxamide derivative (Aventis Pharma), Benzoimidazole carboxamide derivative (Aventis Pharma), Pyrazolo[4,3-c]quinoline derivative (Pharmacia Corporation), Imidazolylquinolinecarbxaldehyde semicarbazide derivative(Tulark Inc.), Pyridyl Cyanoguanidine derivate(Leo Pharma), IκB Kinase Inhibitor Peptide(CalBiochem), IKK-2 Inhibitor IV [5-(p-Fluorophenyl)-2-ureido]thiophene-3-carboxamide(CalBiochem), IKK Inhibitor II (Wedelolactone(CalBiochem), IKK Inhibitor VII (CalBiochem), IKK-2 Inhibitor V (N-(3,5-Bis-trifluoromethylphenyl)-5-chloro-2-hydroxybenzamide IMD-0354, CalBiochem), IKK-2 Inhibitor VI (5-Phenyl-2-ureido)thiophene-3-carboxamide, CalBiochem), IKK-2 Inhibitor VIII (ACHP 2-Amino-6-(2-(cyclopropylmethoxy)-6-hydroxyphenyl)-4-(4-piperidinyl)-3-pyridinecarbonitrile, CalBiochem). ii) In a certain embodiment, the group of IKK inhibitors may additionally include compounds discovered to have IKK inhibitory activity, in accordance, and previously identified as anti-tumor agents, including, but not limited to PS1145(Millennium Pharmaceutical Inc.), BMS-345541* (IKK inhibitor III, Bristol-Myers Squibb Pharmaceutical Research Institute).

(5) at least one nucleotide sequences [SEQ ID NO:1, 10, 11, 12, 13], and means for targeting the genes of polynucleotide sequences [SEQ ID No: 2, 3, 4, 5, 14] and peptide sequences [SEQ ID No: 6, 7, 8, 9, 15] to inhibit the expression levels and functional activities of the corresponding genes by siRNA, antisense RNA, antisense oligo, dominant negative DNA, peptide, peptide inhibitors, antibodies, small molecule inhibitors.

One embodiment provides methods and a treatment protocol for inducing cancer cell death and tumor suppression to treat cancer in a patient. In accordance with this method, it has been discovered that the combination of WST-3 and/or its valid substitutes with an apigenin and/or its valid substitutes for synergistic induction of cancer cell death and suppression of tumor growth.

Accordingly, cancer cells are treated with effective dose(s) of WST-3 and/or at least one of its valid substitutes in combination with apigenin and/or at least one of its valid substitutes in pharmaceutical acceptable medium for effective time period.

The valid substitutes of WST-3 include, but not limited to the compounds that contains the combination of the two said features including (1) the active group as described above that can block the tPMET and/or oxidative phosphorylation and/or the coupling of the tPMET and the oxidative phosphoryalation process (2) the chemical structure that makes the resulting compound impermeable to cell plasma membrane as described above for the first compound as listed.

The suitable active groups that can block the tPMET and oxidative phosphorylation include, but not limited to the DNP group and the cyano group.

Suitable as least one valid substitute for apigenin, as listed above, include, but not limited to (1) any other flavonoids and their isoforms including naturally existed, artificial modified isoforms and synthetic compounds, any isoflevens as described; (3) inhibitors to HIF-1 and/or any inhibitors to cellular responses to hypoxi as described; (4) inhibitors to NOXes especially tNOX as described; (5) inhibitors that can mimic one or more of the predetermined apigenin effects.

It is yet another embodiment to treat cancer cells with WST-3 with at least one apigenin or any of its valid substitutes for both WST-3 and apigenin simultaneously and sequentially in any order for each of the above and following embodiments, forming a more preferred embodiment.

It is yet another embodiment to treat cancer cells with WST-3 with at least one IKK inhibitor or all other valid substitutes for both WST-1r and IKK inhibitor simultaneously and sequentially in any order for each of the above and following embodiments, forming a more preferred embodiment.

The in vitro effective dose of WST-3 may be 50 μM or lower, but can be higher as well.

The effective dose of apigenin under in vitro cell culture may be at 1-100 μM.

The WST-3 or at least one of its valid substitutes and apigenin or at least one of its valid substitutes may be administered to cancer cells or to cancer patients concurrently, separately and/or sequentially in any order.

Each of the treatment agents may be administrated via oral, intra peritonea injection, intra muscular injection, intra venous injection, intra venous infusion, intra artery infusion, intra artery injection, as well as via dermal penetration.

The treatment time of WST-3 or at least one of its valid substitutes may be between pulsed for 30 minutes to 8 hours of initial treatment or continuesly.

The treatment time of apigenin or at least one of its valid substitutes may be last for 15 min to 24 hours consecutively or longer.

In other words, the WST-3 or at least one of its valid substitutes may be treated first with effective dose for 30 minutes to 4 hours in the absence of apigenin, then, remove the WST-3 and administer the apigenin or at least one of its valid substitutes to the cancer cells for another 4 to 24 hours; or Alternatively, administering the apigenin or at least one of its valid substitutes to the cancer cells for another 4 to 24 hours, and then, remove the administer the apigenin or at least one of its valid substitutes and administering the WST-3 or its valid substitutes to cancer cells for 30 minutes to 4 hours; or Alternatively, administering the apigenin or at least one of its valid substitutes and the WST-3 or its valid substitutes to the cancer cells for 30 minutes to 4 hours, then remove the treatments and administering the apigenin or at least one of its valid substitutes for another 4-24 hours, or Alternatively, administering the apigenin or at least one of its valid substitutes for 24 hours, then, administering the WST-3 or at least one of its valid substitutes to the treatment of cancer cells for 30 minutes to 4 hours, Alternatively, administering of apigenin or at least one of its valid substitutes and the WST-3 or its valid substitutes can be concurrently to the cancer cells for 30 minutes to 4 hours.

Alternatively, administering of apigenin or at least one of its valid substitutes and the WST-3 or its valid substitutes can be concurrently to the cancer cells continuesly.

The actual treatment doses of WST-3 and apigenin and the treatment time of these compounds can be adjusted by a physician or a skilled person.

The preferred embodiment for the treatment is to administer the apigenin or at least one of its valid substitutes and the WST-3 or its valid substitutes to the cancer cells for 4 hours, then remove the treatments and administering the apigenin or at least one of its valid substitutes for another 24 hours. This is because we have the most date for.

Cancers that may be treated using the combinatorial protocol with WST-3 or its valid substitutes in combination with apigenin or its valid substitutes are carcinomas and sarcomas include, but are not limited to those carcinomas and sarcomas that may be treated using the present protocol include, but are not limited to: cancers of the sqoumas cell carcinoma, breast, prostate, colorectum, pancreas, cervix, stomach, endometrium, brain, liver, bladder, ovary, testis, head, neck, skin (including melanoma and basal carcinoma), mesothelial lining, esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma, soft tissue sarcoma, as well as lymphomas and leukemia.

Accordingly, one of the embodiments of this invention provides a method for treating cancer in a patient by combination of (1) means of blocking tPMET and/or uncoupling the oxidative-phosphorylation on the cell plasma membrane with (2) means of inhibiting cellular responses to hypoxia, HIF, NOX, NF-κB activity or mimic one or more of predetermined apigenin effects on cancer cells.

The means to block tPMET and/or uncouple oxidative phosphorylation on the cell plasma membrane include, but not limited to: the cell plasma membrane impermeable tMPET oxidative phosphorylation uncoupler or its valid substitutes are the compounds that can inhibit the trans plasma membrane electron transfer process, or the oxidative phosphorylation process or the coupling of electron transport and the oxidative phosphorylation and impermeable to cell plasma membrane.

The means of inhibiting cellular responses to hypoxia, HIF, NOX, NF-κB activity, or mimic one or more of predetermined apigenin effects on cancer cells including, but not limited to treatment with apigenin, or its valid substitutes.

The order of the treatment to cancer cells or cancer patients of the means of blocking tPMET and/or oxidative phosphorylation on the cell plasma membrane with the means of inhibiting cellular responses to hypoxia, HIF, NOX, NF-κB activity, or mimic one or more of predetermined apigenin effects on cancer cells can be concurrently or sequentially in any order at effective doses and effective time period for the treatment.

The present invention also provides additional methods for inducing cancer cell death and suppressing tumor growth in cancer patients. In accordance with the present invention, it has been discovered that the combination of a flavonoid, apigenin, or its valid substitutes, with the WST-3 or the valid substitutes at effective concentration for synergistic induction of cancer cell death. Accordingly, the present invention provides a pharmaceutical composition and protocol for the treatment of cancer in a patient in need with effective dose comprising of at least one flavonoid, specifically, apigenin, or its valid substitutes, with WST-3 or at least one of the valid substitutes of the WST-3 in a pharmaceutical acceptable medium.

Suitable flavonoids include, but not limited to, apigenin and valid substitutes of apigenin as described above in pharmaceutically acceptable medium.

The valid substitutes of apigenin include the compounds that exhibit inhibitory activity as at least one of the effects of that Apigenin does in pharmaceutically acceptable medium.

The suitable at least one of the valid substitutes for the WST-3, as noted herein above include, but are not limited to the individual components that are comprises the active group as represented by DNP and the valid substitutes for tetrazolium salts that make the compound impermeable to cell plasma membrane at optimized concentrations in pharmaceutically acceptable medium.

The effective concentration of apigenin that were used may vary depending on cell type. The preferred dose is at the range of 1-100 µM in vitro.

For all the above and following embodiments, the effective concentration of WST-3 and the valid substitutes may vary depending on the individual composition and the effective concentration of each of the composition may or may not be the same concentration as that in the WST-3 and may vary from each of the compositions and their valid substitutes and between in vitro and in vivo usage. The preferred in vitro concentration range for in vitro treatment of WST-3 is 50 µM or lower in a pharmaceutical acceptable medium.

In a specific embodiment of the present invention, the administration of the WST-3 or at least one valid substitutes of WST-3, the apigenin or at least one of the valid substitutes of apigenin can be in any type of order. Specifically, the WST-3 or at least one valid substitutes of WST-3, and the apigenin or at least one of the valid substitutes of apigenin may be administered to the cells or patient concurrently or sequentially. In other words, the apigenin or at least one of the valid substitutes of apigenin or the WST-3 or the at least one substitute of WST-3 may be administered first, or the WST-3 or at least one valid substitutes of WST-3, and the apigenin or at least one of the valid substitutes of apigenin may be administered at the same time. The preferred order of the treatment in this invention is to administer the WST-3 or the valid substitutes of WST-3 and the apigenin or the valid substitutes of apigenin simultaneously and then, after removal of the WST-3, add apigenin again and keep in contact with cells for another 24 hours.

In a particular embodiment, the treatment of WST-3 is in contact with cells for 15 minutes to 8 hours. The preferred time is between 30 min to 4 hours. The more preferred time is between 2-4 hours. A removal of the WST-3 or its valid substitute's from treatment is required for all the above and following embodiments to induce programmed cell death of the treated cells by this method thereof.

Moreover, the present invention provides a method for the treatment of cancer by administering to a patient, in need thereof, a therapeutically effective dose of at least one of the WST-3 or its valid substitutes and apigenin or at least one of its valid substitutes mentioned above in pharmaceutical acceptable medium.

Cancers that may be treated using the combinatorial protocol with WST-3 or its valid substitutes in combination with apigenin include, but are not limited to Cancers that may be treated using the present protocol include, but are not limited to: colorectum, pancreas, cervix, stomach, endometrium, brain, liver, bladder, ovary, testis, head, neck, skin (including melanoma and basal carcinoma), mesothelial lining, white esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma, leukemia, lymphoma and sarcomas, lymphomas and leukemia.

3. Pharmaceutical Composition and Treatment Method of Combination of WST-1r and Apigenin for the Treatment of Cancer One embodiment of the invention provides pharmaceutical compositions comprising 1) WST-1r or its valid substitutes, which have not previously been established as having an anticancer effect. The WST-1r has been used as a cell proliferation detection agent, the Cell Proliferation—WST-1. When WST-1r combined with 2) apigenin, a flavonoid, or its valid substitutes, or an IKK inhibitor, or trasnfection of Puc19 or its valid substitutes synergize the induction of cancer cell death. Such a pharmaceutical composition may be administered, in a therapeutically effective amount, in optimized concentration in phosphate buffered saline or any of the valid pharmaceutical acceptable medium, to a patient in need for the treatment of cancer.

The afficacy of the said anticancer treatment immediate above was synergized by combination use of WST-1r and its valid substitutes which have not previously been established. The Cell Proliferation WST-1r is composed of a tetrazolium salt, WST-1c (WST-1, Ishiyam M, et al Biol Pharm Bull 1996, 19:1515-20; Berridge M V, et al Biotechnology Annual Review, Vol. II:127-152, 2005), and an IEA, mPMS, (Berridge M V, et al Biotechnology Annual Review, Vol. II:127-152, 2005) diluted in phosphor buffered saline. WST-1r has also been used for measuring tPMET activity. Treatment with WST-1r enhanced cell respiration. When the WST-1r treatment was withdraw following the treatment and in combination of inhibiting HIF by apigenin or any of its valid substitutes resulted in synergized cancer cell death. In the present invention, WST-1r is used as a drug for a combination treatment for cancer therapy.

In accordance, the active gradient of WST-1r for the treatment of cancer can be either the WST-1c or the mPMS or the combination of the two components in optimized concentration and optimized ratio. The WST-1r that as described herein above and there after represents a group of chemical compound or mixture of combinations of a water soluble tetrazolium salt and an IEA that are capable of interacting with and/or interfering to tPMET, and/or capable of inducing reactive oxygen species (ROS) generation.

The valid substitutes of WST-1c include, but not limited to other WST, including, but not limited to WST-3, WST-4, WST-5, WST-9, WST-10, WST-11, MSN and XTT at optimized concentration in a pharmaceutical acceptable medium.

The valid substitutes of mPMS include, other IEAs, examples may be as, but not limited to coenzyme Q1 (Berridge M V, et al Biotechnology Annual Review, Vol. II:127-152, 2005) at optimized concentration in a pharmaceutical acceptable medium.

The WST-1r includes compositions of at least one WST, WST-1c, and at lease one IEA, mPMS in optimized concentration and ratio in a pharmaceutical acceptable medium.

The valid substitute of WST-1r includes, but not limited to (1) the combination of at least one WST with at least one IEA. Examples as, but not limited to: WST-1+mPMS, WST-3+mPMS, WST-4+mPMS WST-5+mPMS, WST-9+mPMS, WST-10+mPMS, WST-11+mPMS, MSN+mPMS XTT+mMS, WST-1+coenzyme Q1, WST-3+coenzyme Q1, WST-4+coenzyme Q1 WST-5+coenzyme Q1, WST-9+coenzyme Q1, WST-10+coenzyme Q1, WST-11+coenzyme Q1, MSN+coenzyme Q1 XTT+coenzyme Q1; (2) at least one of the WST, such as, with no limitation, WST-3; (3) at least one IEA, such as, with no limitation, mPMS and coenzyme Q1 at optimized concentration in a pharmaceutically acceptable medium.

The Apigenin herein represents the second molecule of this combination composition. The valid substitutes of apigenin are selected from the groups comprising: 1) at least one flavone as listed above 2) at least one flavonoids or isoflavonoids as listed above; 3) at least one HIF inhibitors as described above, 3) at least one IKK inhibitors as described above, 4) at least one nucleotide sequences [SEQ ID NO:1, 10, 11, 12, 13], and means for targeting the genes of polynucleotide sequences [SEQ ID No: 2, 3, 4, 5, 14] and peptide sequences [SEQ ID No: 6, 7, 8, 9, 15] as listed above.

It is yet another embodiment to treat cancer cells with WST-1r and apigenin, a flavonoids or all other valid substitutes for both WST-1r and apigenin simultaneously and sequentially in any order for each of the above and following embodiments, forming a more preferred embodiment.

It is yet another embodiment to treat cancer cells with WST-1r with at least one IKK inhibitor or all other valid substitutes for both WST-1r and IKK inhibitor simultaneously and sequentially in any order for each of the above and following embodiments, forming a more preferred embodiment.

It is yet another embodiment to treat cancer cells with (1) the DNA transfection, or IFN, or siRNA transfection or all other valid substitutes and, then, (2) one of the IKK, or CK2 or GSK3β inhibitors and, treat with WST-1r simultaneously or sequentially in any order for each of the above and following embodiments, forming a more preferred embodiment.

It is yet another embodiment to treat with (1) the DNA transfection, or IFN, or siRNA transfection or all other valid substitutes and, then, (2) one of the IKK, or CK2 or GSK3β inhibitors and, treat with electron coupling reagent of the WST-1r simultaneously or sequentially in any order for each of the above and following embodiments, forming a more preferred embodiment It is yet another embodiment to treat with (1) the DNA transfection, or IFN, or siRNA transfection or all other valid substitutes and, then, (2) one of the IKK, or CK2 or GSK3β inhibitors and, simultaneously or sequentially in any order treat with all the remaining subcomponent of the WST-1r for each of the above and following embodiments, forming a more preferred embodiment It is yet another embodiment to treat with (1) the DNA transfection, or IFN, or siRNA transfection or all other valid substitutes and, then, (2) one of the IKK, or CK2 or GSK3β inhibitors and, simultaneously or sequentially in any order treat with any valid substitution for WST-1r for each of the above and following embodiments, forming a more preferred embodiment It is yet another embodiment to treat with (1) the DNA transfection, or IFN, or siRNA transfection or all other valid substitutes and, then, (2) one of the IKK, or CK2 or GSK3β inhibitors and, simultaneously or sequentially in any order treat with any valid substitution for WST-1c for each of the above and following embodiments, forming a more preferred embodiment It is yet another embodiment to treat with (1) the DNA transfection, or IFN, or siRNA transfection or all other valid substitutes and, then, (2) one of the IKK, or CK2 or GSK3β inhibitors and, simultaneously or sequentially in any order treat with any valid substitution for electron coupling reagent of the WST-1r, such as mPMS, for each of the above and following embodiments, forming a more preferred embodiment.

It is yet another embodiment to treat with (1) the DNA transfection, or IFN, or siRNA transfection or all other valid substitutes and, then, (2) one of the IKK, or CK2 or GSK3β inhibitors and, simultaneously or sequentially in any order treat with any valid substitution for the remaining subcomponent of the WST-1r for each of the above and following embodiments, forming a more preferred embodiment.

It is yet another embodiment to treat with (1) the DNA transfection, or IFN, or siRNA transfection or all other valid substitutes and, then, (2) one of the IKK, or CK2 or GSK3β inhibitors and, treat with WST-1r simultaneously or sequentially in any order treat with any valid substitution as any type of combination of the valid substitutes and the subcomponent of the WST-1r for each of the above and following embodiments, forming a more preferred embodiment.

Moreover, the present descriptions provide pharmaceutical compositions and methods for the treatment of cancer by administering to a patient, in need thereof, a therapeutically effective amount of at least one of the WST-1r component or its valid substitutes mentioned immediately above.

The optimized concentration may or may not be the same concentration as that of the Cell Proliferation WST-1 reagent and may vary from each of the compositions and their valid substitutes and between in vitro and in vivo usage. The preferred optimized in vitro WST-1r, WST-3+mPMS, WST-4+mPMS and WST-3 are the most preferred embodiment because they were the component for which we have the most valid data.

Moreover, the present description provides a method for the treatment of cancer by administering to a patient, in need thereof, a therapeutically effective amount of at least one of the WST-1r component or its valid substitutes mentioned immediately above.

In a particular embodiment, the preferred treatment of WST-1r is in contact with cells for at lease 15 minutes or longer. The more preferred treatment time for WST-1r is between 30 min to 4 hours. The even more preferred treatment time for WST-1r is between 2-4 hours.

Each of the treatment agents may be administrated via oral, intra peritonea injection, intra muscular injection, intra venous injection, intra venous infusion, intra artery infusion, intra artery injection, as well as via dermal penetration.

Cancers that may be treated using the present protocol include, but are not limited to: carcinoma derived from prostate, colorectum, pancreas, cervix, stomach, endometrium, brain, liver, bladder, ovary, testis, head, neck, skin (including melanoma and basal carcinoma), mesothelial lining, white esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, and testicular seminoma, leukemia, lymphoma and sarcomas.

4. Combinatorial Therapies with Inhibitors and WST-1r for the Treatment of Cancer The present description provides additional methods for inducing cancer cell death for the treatment of cancer for a patient in need. In accordance, it has been discovered that the combination of pUC19 DNA transfection and/or its valid substitutes with an IKK inhibitor plus WST-1r or its valid substitutes for synergistic inducing cancer cell death. Accordingly, the present description provides a pharmaceutical composition and protocol for the treatment of cancer in a patient comprising at lease pUC19 DNA transfection or its valid substitutes in combination with at least one IKK inhibitor and WST-1r or at least one of the valid substitutes of the WST-1r. Also provided is a method for treating cancer in a patient by IFN in combination with administering an effective amount of at least one IKK inhibitor and WST-1r or at least one of the valid substitutes of the WST-1r. Also provided is a method for treating cancer in a patient by transfection of the cells with siRNA in combination with administering an effective amount of at least one IKK inhibitor and WST-1r or at least one of the valid substitutes of the WST-1r.

The DNA transfection may be substituted by (i) administering a suitable dose of at least one IFN, or (ii) transfection of at least one specific siRNA targeting at least one of the target transcripts as described previously in this description, or (iii) chemical compounds or small molecule inhibitors that targets at least one of the target genes and/or its gene products as described previously in this description, or (iv) antibodies targeting at least one of the target genes products as described previously in this description, (v) anti-sense RNAs targeting at least one of the target transcripts as described previously in this description, (vi) shRNAs targeting at least one of the target transcripts as described previously in this description, (vii) anti-sense oligos targeting at least one of the target transcripts as described previously in this description, (viii) A dominant negative DNA vector targeting at least one of the target genes as described previously in this description, (ix) peptides targeting at least one of the target genes products as described previously in this description.

The target genes are, but not limited to, (1) *Homo sapiens* transient receptor potential cation channel, subfamily C, member 6(TRPC6, GeneID: 7225,), mRNA (NM_004621.3) synonyms: TRP6, FSGS2, FLJ11098 (SEQ ID #2, #6), (2) *Homo sapiens* SH3 and PX domains 2B (SH3PXD2B), mRNA (. (SH3PXD2B, GeneID: 285590), mRNA (NM_001017995) synonyms: HOFI; FLJ20831; KIAA1295 (SEQ ID #3, #7), (3) *Homo sapiens* membrane associated guanylate kinase, WW and PDZ domain containing 3 (MAGIKK, GeneID: 260425), transcript variant 2, mRNA (NM_152900.1) synonyms: MAGI-3, MGC163281 (SEQ ID #4, #8), and (4) the *Homo sapiens* transmembrane protein 182 (TMEM182, GeneID: 130827), mRNA (NM_144632.2) (SEQ ID #5, #9).

The gene products include, but not limited to, the transcripts from these genes and proteins above.

The siRNA sequences and the targets of the siRNA sequences may also include the human genomic sequences that flanking the genes as listed in the attached file entitled: "NCBI Blast-pUC19-Human-Transcripts and genome(2686 letters)", "NCBI Blast_siRNA2 Nucleotide sequence (24 letters)" and "NCBI Blast_pcDNA3 Nucleotide sequence (5448 letters)". NCBI Blast-pUC19-Human-Transcripts and genome.

The at least one IFN may be selected from the subfamily of type I IFN including, but not limited to: IFNα A, IFNα B, IFNα C, IFNα D, IFNα F, IFNα G, IFNα H, IFNα I, IFNα J, IFNα K, IFNα 4b, IFNα WA, and IFNα.

The effective concentration of IFN that were used for treating cancer cells was 10 unit/ml or lower for each IFN used.

Suitable IKK inhibitors include any compound which exhibits IKK inhibitory activity.

The at least one IKK inhibitor may be selected from compounds of the group consisting of, without limitation, i) compounds previously established to exhibit IKK inhibitory properties including, but not limited to: SPC839 (Signal Pharmaceutical Inc.), Anilino-Pyrimidine Derivative(Signal Pharmaceutical Inc.), PS1145(Millennium Pharmaceutical Inc.), BMS-345541*(IKK inhibitor III, Bristol-Myers Squibb Pharmaceutical Research Institute), SC-514*(Smithkilne Beecham Corp.), Amino-imidazolecarboxamide derivative (Smithkilne Beecham Corp.), Ureudo-thiophenecarboxamide derivatives(AstraZeneca), Diarylpybidine derivative (Bayer), Pyridooxazinone derivative(Bayer), Indolecarboxamide derivative(Aventis Pharma), Benzoimidazole carboxamide derivative(Aventis Pharma), Pyrazolo[4,3-c]quinoline derivative(Pharmacia Corporation), Imidazolylquinoline-carbxaldehyde semicarbazide derivative (Tulark Inc.), Pyridyl Cyanoguanidine derivate(Leo Pharma), IκB Kinase Inhibitor Peptide(CalBiochem), IKK-2 Inhibitor IV [5-(p-Fluorophenyl)-2-ureido]thiophene-3-carboxamide(CalBiochem), IKK Inhibitor II (Wedelolactone (CalBiochem), IKK Inhibitor VII (CalBiochem), IKK-2 Inhibitor V (N-(3,5-Bis-trifluoromethylphenyl)-5-chloro-2-hydroxybenzamide IMD-0354, CalBiochem), IKK-2 Inhibitor VI (5-Phenyl-2-ureido)thiophene-3-carboxamide, CalBiochem), IKK-2 Inhibitor VIII (ACHP 2-Amino-6-(2-(cyclopropylmethoxy)-6-hydroxyphenyl)-4-(4-piperidinyl)-3-pyridinecarbonitrile, CalBiochem). ii) In a certain embodiment, the group of IKK inhibitors may additionally include compounds discovered to have IKK inhibitory activity, in accordance, and previously identified as anti-tumor agents, including, but not limited to PS1145(Millennium Pharmaceutical Inc.), BMS-345541*(IKK inhibitor III, Bristol-Myers Squibb Pharmaceutical Research Institute).

Suitable WST-1r and the at least one of the valid substitutes of the WST-1r, as noted herein above, include, but are not limited to to (1) the combination of at least one WST with at least one IEA. Examples as, but not limited to: WST-1+mPMS, WST-3+mPMS, WST-4+mPMS WST-5+mPMS, WST-9+mPMS, WST-10+mPMS, WST-11+mPMS, MSN+mPMS XTT+mMS, WST-1+coenzyme Q1, WST-3+coenzyme Q1, WST-4+coenzyme Q1 WST-5+coenzyme Q1, WST-9+coenzyme Q1, WST-10+coenzyme Q1, WST-11+coenzyme Q1, MSN+coenzyme Q1 XTT+coenzyme Q1; (2) at least one of the WST, such as, with no limitation, WST-3;

(3) at least one IEA, such as, with no limitation, mPMS and coenzyme Q1 at optimized concentration in a pharmaceutically acceptable medium.

In a specific embodiment, the preferred order of treatment is to administer the pUC19 DNA transfection or its valid substitutes, at least one IKK inhibitor and WST-1r or at least one of the valid substitutes of WST-1r concurrently and/or sequentially in any type of order. However, the pUC19 DNA transfection or IFN treatment, or siRNA transfection or its other valid substitutes, at least one IKK inhibitor and the WST-1r or the at least one valid substitutes of WST-1r may be administered to the cells or patient concurrently or sequentially. In other words, the pUC19 DNA transfection may be treated first, the at least one IKK inhibitor may be administered first, the WST-1r or the at least one substitute of WST-1r may be administered first, or the pUC19 DNA transfection, the at least one IKK inhibitor and the at least one substitute of WST-1r may be administered at the same time. Additionally, when the pUC19 DNA transfection is replaced by siRNA transfection, IFN administration, or small molecule targeting the target genes as described in this description above, in combination with at least one IKK inhibitor and WST-1r or at least one valid substitute of WST-1r is used, the compounds may be administered in any order.

Cancers that may be treated using the present combinatorial protocol are carcinomas and sarcomas, lymphomars and leukemia include, but are not limited to those cancers described herein above.

However, the suitable cancer cells and tumors that may be more susceptible to this treatment are those with aberrant NF-κB activities.

The present description also provides additional methods for inducing cancer cell death and suppressing tumor in cancer patients. In accordance, it has been discovered that the combination of a flavonoid, apigenin, or its valid substitutes, or an IKK inhibitor at effective concentration with the WST-1r or the valid substitutes at effective concentration for synergistic induction of cancer cell death. Accordingly, the present description provides a pharmaceutical composition and protocol for the treatment of cancer in a patient in need with effective dose comprising of at least one flavonoid, preferably, apigenin, or its valid substitutes, or an IKK inhibitor with WST-1r or at least one of the valid substitutes of the WST-1r in a pharmaceutical acceptable medium.

A removal of the treatment is required for all the above and following embodiments to induce programmed cell death of the treated cells by this method.

Suitable flavonoids include, but not limited to, apigenin, the flavonoids, and valid substitutes of apigenin as described above in pharmaceutically acceptable medium.

The valid substitutes of apigenin are selected from the groups comprising The second compound and the valid substitutes of apigenin is selected from the groups comprising (1) At least one flavones, include, but not limited to nature existed flavones, such as: Luteolin, Tangeritin, Chrysin, 6-hydroxyflavone, Baicalein, Scutellarein, Wogonin and synthetic flavones, such as: Diosmin, Flavoxate, additional subgroups of flavones:flavonols, flavannones, flacanonols, catechins, isoflavones; or(2) at least one from other subgroups of Flavonoid or Bioflavonoids and their isoforms including naturally existed, artificial modified isoforms and synthetic compounds including, but not limited to flavonoids, derived from 2-phenylchromen-4-one (2-phenyl-1,4-benzopyrone) structure (examples: quercetin, rutin); isoflavonoids, derived from 3-phenylchromen-4-one (3-phenyl-1,4-benzopyrone) structure; neoflavonoids, derived from 4-phenylcoumarine (4-phenyl-1,2-benzopyrone) structure, and flavanoids as a non-ketonepolyhydroxy polyphenol compounds as described above; or (3) At least one HIF inhibitors and/or inhibition of cellular responses to hypoxia including, but not limited to: 2,2-dimethybenzopyran compounds, chetomin, 2-methoxyestradiol (2ME2), PX-478,17-N-allylamino-17-demethoxygeldanamycin (17-AAG), EZN-2968, camptothecins, NSC 644221, 3-(5'-hydroxymethyl-2'-furyl)-1-benzylindazole (YC-1), rapamycin, and decoy oligonucleotides against HIF-1 RX-0047; as as described above in effective doses and in pharmaceutically acceptable medium.

Suitable IKK inhibitors are as listed above and following embodiments include any compound which exhibits IKK inhibitory activity in pharmaceutically acceptable medium. The at least one IKK inhibitor may be selected from compounds of the group consisting of, without limitation, i) compounds previously established to exhibit IKK inhibitory properties including, but not limited to: SPC839 (Signal Pharmaceutical Inc.), Anilino-Pyrimidine Derivative(Signal Pharmaceutical Inc.), PS1145(Millennium Pharmaceutical Inc.), BMS-345541*(IKK inhibitor III, Bristol-Myers Squibb Pharmaceutical Research Institute), SC-514*(Smithkline Beecham Corp.), Amino-imidazolecarboxamide derivative (Smithkilne Beecham Corp.), Ureudo-thiophenecarboxamide derivatives(AstraZeneca), Diarylpybidine derivative (Bayer), Pyridooxazinone derivative(Bayer), Indolecarboxamide derivative(Aventis Pharma), Benzoimidazole carboxamide derivative(Aventis Pharma), Pyrazolo[4,3-c]quinoline derivative(Pharmacia Corporation), Imidazolylquinoline-carbxaldehyde semicarbazide derivative (Tulark Inc.), Pyridyl Cyanoguanidine derivate(Leo Pharma), IκB Kinase Inhibitor Peptide(CalBiochem), IKK-2 Inhibitor IV [5-(p-Fluorophenyl)-2-ureido]thiophene-3-carboxamide(CalBiochem), IKK Inhibitor II (Wedelolactone (CalBiochem), IKK Inhibitor VII (CalBiochem), IKK-2 Inhibitor V (N-(3,5-Bis-trifluoromethylphenyl)-5-chloro-2-hydroxybenzamide IMD-0354, CalBiochem), IKK-2 Inhibitor VI (5-Phenyl-2-ureido)thiophene-3-carboxamide, CalBiochem), IKK-2 Inhibitor VIII (ACHP 2-Amino-6-(2-(cyclopropylmethoxy)-6-hydroxyphenyl)-4-(4-piperidinyl)-3-pyridinecarbonitrile, CalBiochem). ii) In a certain embodiment, the group of IKK inhibitors may additionally include compounds discovered to have IKK inhibitory activity, in accordance, and previously identified as anti-tumor agents, including, but not limited to PS1145(Millennium Pharmaceutical Inc.), BMS-345541*(IKK inhibitor III, Bristol-Myers Squibb Pharmaceutical Research Institute).

Suitable WST-1r and the at least one of the valid substitutes of the WST-1r, as noted herein above, include, but are not limited to WST-1r and each of the individual components, the WST-1c anf mPMS, that are comprises the WST-1r, the valid substitutes for WST and that for IEA of the WST-1r and all possible combination among these valid substitutes of WST-1 and mPMS or the combination of these valid substitutes and the individual component of the WST-1r, the WST and IEA as described above at optimized concentrations in pharmaceutically acceptable medium.

The effective concentration of apigenin that were used may vary depending on cell type. For all the above and following embodiments, the effective concentration of WST-1r and the valid substitutes may vary depending on the individual composition and the effective concentration of each of the composition may or may not be the same concentration as that in the Cell Proliferation WST-1 reagent and may vary from each of the compositions and their valid substitutes and between in vitro and in vivo usage.

In a specific embodiment, the administration of the WST-1r or at least one valid substitutes of WST-1r, the apigenin, the flavonoid or at least one of the valid substitutes of apigenin or the at least one IKK inhibitor can be in any type of order. Specifically, the WST-1r or at least one valid substitutes of WST-1r, and the apigenin or at least one of the valid substitutes of apigenin or the at least one IKK inhibitor may be administered to the cells or patient concurrently or sequentially. In other words, the apigenin or at least one of the valid substitutes of apigenin or the at least one IKK inhibitor may be administered first, the WST-1r or the at least one substitute of WST-1r may be administered first, or the WST-1r or at least one valid substitutes of WST-1r, and the apigenin or at least one of the valid substitutes of apigenin or the at least one IKK inhibitor may be administered at the same time. The preferred order of the treatment is to administer the WST-1r or the valid substitutes of WST-1r and the apigenin or the valid substitutes of apigenin or at least one IKK inhibitor simultaneously and then, after removal of the WST-1r, add apigenin or IKK inhibitor again and keep in contact with cells for another 24 hours.

In a particular embodiment, the in vitro treatment of WST-1r is in contact with cells for at least 15 minutes or longer The preferred time is between 30 min to 4 hours. The more preferred time is between 2-4 hours. A removal of the WST-1r or its valid substitute's from treatment is required for all the above and following embodiments to induce programmed cell death of the treated cells by this method thereof.

Moreover, the present description provides a method for the treatment of cancer by administering to a patient, in need thereof, a therapeutically effective dose of at least one of the WST-1r or its valid substitutes and apigenin or at least one of its valid substitutes as described above in pharmaceutical acceptable medium.

Also, the present description provides a method for the treatment of cancer by administering to a patient, in need thereof, a therapeutically effective dose of at least one of the WST-1r or its valid substitutes and at least one IKK inhibitor mentioned above in pharmaceutical acceptable medium.

Cancers that may be treated using the combinatorial protocol with WST-1r or its valid substitutes in combination with apigenin include, but are not limited to those carcinomas and sarcomas that may be treated using the present protocol include, but are not limited to: cancers of the prostate, colorectum, pancreas, cervix, stomach, endometrium, brain, liver, bladder, ovary, testis, head, neck, skin (including melanoma and basal carcinoma), mesothelial lining, esophagus, breast, muscle, connective tissue, lung (including small-cell lung carcinoma and non-small-cell carcinoma), adrenal gland, thyroid, kidney, or bone; glioblastoma, mesothelioma, renal cell carcinoma, gastric carcinoma, sarcoma, choriocarcinoma, cutaneous basocellular carcinoma, lymphoma, leukemia and testicular seminoma, soft tissue sacoma.

5. Other Compositions and Methods for Enhance and Synergize the Treatment of Cancer The present description provides additional methods for synergistic inhibition of NF-κB activity in cancer cells. In accordance, it has also been discovered that the pUC19 DNA transfection may also synergize the inhibition of NF-κB activity in cancer cells when both IKK1-KA and IKK2-KA kinase dead dominant negative vector were used simultaneously. This inhibitory effect can be further enhanced by the combination of additional treatment of WST-1r or at least one of the valid substitutes for WST-1r.

Accordingly, pUC19 DNA trasnfection may be substituted by treating the cells or a mammal with (i) administering a suitable dose of at least one IFN, or (ii) transfection of at least one specific siRNA or shRNA targeting at least one of the target transcripts as described previously in this specification, or (iii) small molecule inhibitors that targets at least one of the target genes products as described previously in this specification, or (iv) antibodies and peptide inhibitors targeting at least one of the target genes products as described previously in this specification, (v) anti-sense RNA targeting at least one of the target transcripts as described previously in this specification, (vi) anti-sense oligo targeting at least one of the target gene's transcripts as described previously in this specification in combination with the treatment of at least one IKK inhibitors that can inhibit both IKK1 and IKK2 kinase activities.

The at least one IFN may be selected from the subfamily of IFN including, but not limited to: IFNα A, IFNα B, IFNα C, IFNα D, IFNα F, IFNα G, IFNα H, IFNα I, IFNα J, IFNα K, IFNα 4b, IFNα WA, IFNβ, IFNγ or IL-6.

The transcripts, and proteins as the targets of the siRNA, shRNA, small molecule inhibitor, peptide inhibitor, antibody, anti-sense RNA, anti-sense oligo, and antibody are, but not limited to, (1) *Homo sapiens* transient receptor potential cation channel, subfamily C, member 6(TRPC6, SEQ ID 2, 6), (2) *Homo sapiens* SH3 and PX domains 2B (SH3PXD2B, SeQ ID #3, #7), (3) *Homo sapiens* membrane associated guanylate kinase, WW and PDZ domain containing 3 (MAG-IKK, SeQ ID #4, #8), (4) the *Homo sapiens* transmembrane protein 182 (TMEM182, SeQ ID #5, #9) and (5) the C6orf108 (Seq ID #14, #15).

Suitable WST-1r and the at least one of the valid substitutes of the WST-1r, as noted herein above, include, but are not limited to WST-1r and each of the individual tetrazolium components that are comprises the WST-1r, the valid substitutes of each component of the WST-1r and any type of combination among these valid substitutes or the combination among these valid substitutes and the individual component of the WST-1 and mPMS.

The at least one IKK inhibitor may be selected from compounds of the group consisting of: i) compounds previously established to exhibit IKK inhibitory properties including, but not limited to: SPC839 (Signal Pharmaceutical Inc.), Anilino-Pyrimidine Derivative(Signal Pharmaceutical Inc.), PS1145(Millennium Pharmaceutical Inc.), BMS-345541* (Bristol-Myers Squibb Pharmaceutical Research Institute), SC-514*(Smithkilne Beecham Corp.), Amino-imidazolecarboxamide derivative(Smithkilne Beecham Corp.), Ureudo-thiophenecarboxamide derivatives(AstraZeneca), Diarylpy-bidine derivative(Bayer), Pyridooxazinone derivative (Bayer), Indolecarboxamide derivative(Aventis Pharma), Benzoimidazole carboxamide derivative(Aventis Pharma), Pyrazolo[4,3-c]quinoline derivative(Pharmacia Corporation), Imidazolylquinoline-carbxaldehyde semicarbazide derivative(Tulark Inc.), Pyridyl Cyanoguanidine derivate (Leo Pharma), IkB Kinase Inhibitor Peptide(CalBiochem), IKK-2 Inhibitor IV [5-(p-Fluorophenyl)-2-ureido]thiophene-3-carboxamide(CalBiochem), IKK Inhibitor II, Wedelolactone(CalBiochem), IKK Inhibitor VII K Inhibitor VII(CalBiochem), IKK-2 Inhibitor V N-(3,5-Bis-trifluoromethylphenyl)-5-chloro-2-hydroxybenzamide IMD-0354(CalBiochem), IKK-2 Inhibitor VI (5-Phenyl-2-ureido)thiophene-3-carboxamide(CalBiochem), IKK-2 Inhibitor VIII ACHP 2-Amino-6-(2-(cyclopropylmethoxy)-6-hydroxyphenyl)-4-(4-piperidinyl)-3-pyridinecarbonitrile (CalBiochem). In a certain embodiment, the group of IKK inhibitors may additionally include compounds discovered to have IKK inhibitory activity, in accordance, and previously identified as anti-tumor agents, including, but not limited to PS1145 (Millennium Pharmaceutical Inc.), BMS-345541* (Bristol-Myers Squibb Pharmaceutical Research Institute).

The preferred IKK inhibitors are the IKK inhibitors that can inhibit both IKK1 and IKK2 kinase activities.

The present description provides additional medical use for inducing cancer cell death and tumor suppression. In accordance, it has been discovered that the combination of a GSK3β inhibitor with a CK2 inhibitor in combination with WST-1r or at least one of the valid substitutes for WST-1r act synergistically to suppress tumor growth. Accordingly, the present description provides a pharmaceutical composition for the treatment of cancer in a subset of cancer cells and/or in a patient comprising at least one GSK3β inhibitor, at least one CK2 inhibitor and WST-1r or the at least one of the valid substitutes for WST-1 in a pharmaceutically acceptable carrier. Also provided is a method for treating cancer in a patient by administering an effective amount of at least one GSK3β inhibitor in combination with at least one CK2 inhibitor. Suitable GSK3β inhibitors include any compound which exhibits GSK3β inhibitory activity, for example, LiCl. Suitable CK2 inhibitors, include, but are not limited to: Apigenin The at least one CK2 inhibitor may be selected from compounds of the group comprising, but not limited to: TBB, TBBz, emodin, CK2 inhibitor III (sigma).

Suitable WST-1r and the at least one of the valid substitutes of the WST-1r, as noted herein above, include, but are not limited to WST-1r and each of the individual components that comprises the WST-1r, the valid substitutes of each component of the WST-1r and any type of combination among these valid substitutes or the combination among these valid substitutes and the individual component of the WST-1r.

In a specific embodiment, the at least one GSK3β inhibitor and at least one CK2 inhibitor may be administered to the cancer cells or patient concurrently or sequentially. In other words, the at least one GSK3β inhibitor may be administered first, the at least one CK2 inhibitor may be administered first, or the at least one GSK3β inhibitor and the at least one CK2 inhibitor may be administered at the same time. Additionally, when more than one GSK3β inhibitor and/or CK2 inhibitor are used, the compounds may be administered in any order.

Cancer cells that may be treated using the present combinatorial protocol include, but are not limited to UM-SCC-6 cells. Cancers that may be treated using the present combinational protocol include, but are not limited to, those cancers described herein.

The present description provides additional medical use for enhancing or synergizing the efficacy effects of chemotherapy drugs for the treatment of cancer. In accordance, it has also been discovered that the Puc19 DNA transfection also synergizes suppression of tumor growth and promotes cancer cell death. Accordingly, the present description provides a pharmaceutical composition for the treatment of cancer in a patient comprising puc19 DNA transfection or at least one of its valid substitutes and at least one chemotherapeutic agent. This induction of cancer cell death effect may be further enhanced by additional combination with WST-1r or at least one of the valid substitutes of WST-1r in a pharmaceutically acceptable carrier. Also provided is a method for treating cancer cells or cancer in a patient by administering an effective dose of at least one DNA transfection or at least one of the valid substitutes for DNA transfection in combination with at least one chemotherapeutic agent. In a preferred embodiment, the preferred DNA for transfection is pUC19 DNA cloning vector as described previous in this application (Sequence #1).

The at least one valid substitute for the pUC19 DNA transfection may include, but not limited to, (i) administering a suitable dose of at least one IFN, or (ii) transfection of at least one specific siRNA targeting at least one of the target transcripts as described previously in this specification, or (iii) at least one chemical compounds or small molecule inhibitors that targets at least one of the target genes and/or its gene products as described previously in this specification, or (iv) at lease one antibody targeting at least one of the target genes products as described previously in this specification, or (v) anti-sense RNA targeting at least one of the target transcripts as described previously in this specification, (vi) shRNA targeting at least one of the target transcripts as described previously in this specification, (vii) anti-sense oligo targeting at least one of the target transcripts as described previously in this specification, (viii) A dominant negative DNA vector targeting at least one of the target genes as described previously in this specification, (ix) peptides targeting at least one of the target genes products as described previously in this specification.

Suitable IFN may be selected from any IFN subfamily members, which include, but not limited to, IFNα A, IFNα B, IFNα C, IFNα D, IFNα F, IFNα G, IFNα H, IFNα I, IFNα J, IFNα K, IFNα 4b, WA, IFNβ, IFNγ and Interlukine-6 (IL-6). In a preferred embodiment, the preferred IFN are subfamily members of IFNα, IFNβ. The effective concentration of IFN is 10 unit/ml or lower for each IFN.

The target genes to be targeted by the at least one chemical compounds or small molecule inhibitors, at least one specific siRNA, shRNA, anti-sense RNA, anti-sense oligo, dominant negative DNA vector, at least one peptide, at lease one antibody, at least one inhibitor are, but not limited to, (1) TRPC6, (SEQ ID #2, #6), (2) SH3PXD2B, (SEQ ID #3, #7), (3) MAGIKK, (SEQ ID #4, #8), (4) TMEM182, (SEQ ID #5, #9), and (5) C6orf108 (Seq ID #14, #15).

The gene products include, but are not limited to, the nucleotide sequence of the transcripts from the gene and amino acid sequence of the protein that derived from these genes.

The siRNA and or shRNA sequences and the targets of the siRNA sequences may also include the nucleotide sequence that mapped to the human genomic sequences that flanking the genes as listed in the attached file "NCBI Blast-pUC19-Human-Transcripts and genome(2686 letters)" and "NCBI Blast_siRNA2 Nucleotide sequence (24 letters)".

Accordingly, Suitable siRNAs include siRNA1 (SEQ ID #10), siRNA 2(SEQ ID #11), and siRNA 3(SEQ ID #12) as described previous in this specification and all the potential siRNAs that may be derived from pUC19 DNA sequence that mapped to human genome and/or transcripts in short pieces (10-100 by and more). These nucleotide sequences and their corresponding genes are listed in the attached file "NCBI Blast-pUC19-Human-Transcripts and genome(2686 letters)" and "NCBI Blast_siRNA2 Nucleotide sequence (24 letters)". As in general, these siRNA sequences can be vary up to 40% from the exact sequences of the gene. Additionally, the function of these siRNAs can be substituted by any of the siRNA and/or shRNA that mapped to other part sequences of the corresponding target gene, small molecule inhibitors, peptide inhibitors, antibodies, anti-sense RNAs, anti-sense oligos and dominant negative DNA vectors that can effectively target the gene products as targets, which are the target of the siRNAs as described above in this paragraph and are include, but not limited to, (1) TRPC6, (SEQ ID #2, #6), (2) SH3PXD2B, (SEQ ID #3, #7), (3) MAGIKK, (SEQ ID #4, #8), (4) TMEM182, (SEQ ID #5, #9), and (5) C6orf108 (Seq ID #14, #15).

The WST-1r or at least one of the valid substitutes of WST-1r, as noted herein above, include, but are not limited to WST-1r and each of the individual components that are comprises the WST-1r, the valid substitutes of each component of the WST-1r and any type of combination among these valid substitutes or the combination among these valid substitutes and the individual component of the WST-1r.

Suitable chemotherapeutic agents include, but are not limited to: paclitaxel (Taxol®), cisplatin, docetaxol, carboplatin, vincristine, vinblastine, methotrexate, cyclophosphamide, CPT-11, 5-fluorouracil (5-FU), gemcitabine, estramustine, carmustine, adriamycin (doxorubicin), etoposide, arsenic trioxide, irinotecan, and epothilone derivatives. The preferred chemotherapeutic agents are paclitaxel (Taxol®), cisplatin, 5-fluorouracil (5-FU), and In a specific embodiment, the preferred order is to transfect the pUC19 DNA or at least one of its valid substitutes first and, then, administering the chemotherapy drugs after the transfection of pUC19DNA. However, the pUC19 DNA transfection or at least one of its valid substitutes and administering the chemotherapy drugs may be administered to the cancer cells or patient concurrently or sequentially. In other words, the pUC19 DNA transfection may be administered first; the chemotherapy drugs may be administered first.

Cancers that may be treated using the present combinatorial protocol include, but are not limited to those carcinomas and sarcomas set forth herein above.

Combined Treatment of Apigenin and Stattic Synergistic Inhibition of Cal27 Cell Survival And Induced Cell Death.

In addition to NF-κB, Signal transducer and activator of transcription (Stat) is another family of transcription factors. They mediate extra cellular signals stimulated by cytokines and growth factors, translocation to the cell nucleus where they act as transcription activators. These proteins mediate the expression of a variety of genes in response to cell stimuli, and thus play a key role in many cellular processes such as cell growth and apoptosis. Stat, such as STAT3, play an important role in cancer cells survival and proliferation. However, Stat Inhibitors or IKK inhibitors alone showed little inhibiting effect on cancer cell survival. Evidence showed that these two transcription factors interact with each other and to functionally cooperate with each other. In addition, NF-κB and STAT binding sites linked together to form promoter modules. Combination of Stattic, a Stat inhibitor with either IKK inhibitor or apigenin results in synergetic induction of cell death. This combination provides a method of treating cancer.

The present invention provides additional methods for inducing cancer cell death and tumor suppression. In accordance with the present invention, it has been discovered that the combination of a IKK inhibitor or a CK2 inhibitor in combination with Stat inhibitor, stattic, or at least one of the valid substitutes for stattic act synergistically to induce cancer cell death and to suppress tumor growth. Accordingly, the present invention provides a pharmaceutical composition for the treatment of cancer in a subset of cancer cells and/or in a patient comprising at least one IKK inhibitor or at least one CK2 inhibitor and stattic or the at least one of the valid substitutes for stattic in a pharmaceutically acceptable carrier. Also provided is a method for treating cancer in a patient by administering an effective amount of at least one IKK inhibitor or at least one CK2 inhibitor in combination with stattic or valid substitutes. Suitable IKK inhibitors are as listed above. Suitable CK2 inhibitors, include, but are not limited to: Apigenin. Suitable Stat inhibitors are the inhibitors that inhibit stat phosphorylation, activation and nuclear translocation, include, but not limited to, stattic. The administration of the IKK inhibitors or the CK2 inhibitors and the stattic may be administered in any order. The preferred order is to administrate the inhibitors concurrently.

Advantages

From the description above, a number of advantages of the embodiments of this cancer treatment protocol and composition become evident:

This combination treatment targeting the tPMET and the HIF or cell responses to hypoxia is a synergistic combination strategy that block cancer cell respiration through the tPMET at cell surface while inhibit cancer cell capability of tolerating hypoxia. This combination did not inhibit cancer cell growth, but induced synergistic cancer specific cell death. This combination composition and method represent a new concept and principle for a new avenue of cancer treatment strategy for a synergistic cancer specific treatment and anti-cancer drug development.

The chemical structure of WST-3 represents a model of a class of compounds that is capable of interfering the tPMET and restricts its activity on cell surface without affecting the mitochondrial in the normal cells. As cancer cells rely on cell surface ixygen consumption, the WST-3 represents the model of compounds that selectively affect cancer cells only.

The use of WST-1r also represents a novel strategy that incorporate cellular response to the treatemtn into the treatment protocol by inducing cancer cell tPMET followed by withdraw to induce cancer cells death.

This combination treatment is different from conventional chemotherapy that inhibits cancer cell growth, instead, it directly induce cancer cell death, which made it a more efficient cancer treatment by selectively killing cancer cells.

In summary this present invention provides a new concept of combinational treatment strategy for anticancer drug development. This combination treatment will selectively block the cell surface respiration of cancer cell while inhibiting their capability to response to hypoxia therefor, to inhibit cancer cell respiration and hence the energy metabolism from two direction to obtain synergistic inducible cancer cell death. In addition, these treatments utilize non cytotoxic compounds result in synergistic cancer specific cell death, which provides a new avenue for anti-cancer drug development and for cancer treatment.

Although the description above contains much specificity, these should not be construed as limiting the scope of the embodiments but as merely providing illustrations of some of the presently preferred embodiments. For example, the WST-3 and the apigenin each represents classes of chemical compounds with similar function. Also the combination of WST-3 and apigenin represents a new strategy and a new avenue of cancer drug development by targeting tPMET in combination with inhibition of cellular responses to hypoxia and some other related process.

Thus the scope of the embodiments should be determined by the appended claims and their legal equivalents, rather than by the examples given.

V. Administration of Pharmaceutical Compositions and Compounds

The pharmaceutical compositions can be administered by any suitable route, for example, by injection, by intra vaneus infusion, by intra artery infusion, by oral, pulmonary, nasal, transdermal or other methods of administration. In general, pharmaceutical compositions of the present specification comprise, among other things, pharmaceutically acceptable diluents, preservatives, solubilizers, emulsifiers, adjuvants and/or carriers. Such compositions can include diluents of various buffer content (e.g., Tris-HCl, acetate, phosphate), pH and ionic strength; and additives such as detergents and solubilizing agents (e.g., Tween 80, Polysorbate 80), antioxidants (e.g., ascorbic acid, sodium metabisulfite), preservatives (e.g., Thimersol, benzyl alcohol) and bulking substances (e.g., lactose, mannitol). The compositions can be incorporated into particulate preparations of polymeric compounds such as polylactic acid, polyglycolic acid, etc., or into liposomes. Such compositions may influence the physical state, stability, rate of in vivo release, and rate of in vivo clearance of components of a pharmaceutical compositions. See, e.g., Remington's Pharmaceutical Sciences, 18th Ed. (1990, Mack Publishing Co., Easton, Pa. 18042) pages 1435-1712 which are herein incorporated by reference. The pharmaceutical compositions can be prepared, for example, in liquid form, or can be in dried powder form (e.g., lyophilized). Particular methods of administering pharmaceutical compositions are described hereinabove.

In yet another embodiment, the pharmaceutical compositions can be delivered in a controlled release system, such as using an intravenous infusion, an implantable osmotic pump, a transdermal patch, liposomes, or other modes of administration. In a particular embodiment, a pump may be used (see Langer, supra; Sefton, CRC Crit. Ref Biomed. Eng. (1987) 14:201; Buchwald et al., Surgery (1980) 88:507; Saudek et al., N. Engl. J. Med. (1989) 321:574). In another embodiment, polymeric materials may be employed (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989) 71:105). In yet another embodiment, a controlled release system can be placed in proximity of the target tissues of the animal, thus requiring only a fraction of the systemic dose (see, e.g., Goodson, in Medical Applications of Controlled Release, supra, (1984) vol. 2, pp. 115-138). In particular, a controlled release device can be introduced into an animal in proximity of the site of inappropriate immune activation or a tumor. Other controlled release systems are discussed in the review by Langer (Science (1990) 249:1527-1533).

The conclusion that this is programmed cell death is formed by the observation that normal cells had no cytotoxic reaction and further, that a over 90% kill rate is more than substantial evidence of a significant find. Therein, because this specification touches a programmed cancer cell death pathway that was prior untouched, or in the alternative, that this invention may activates a known pathway or a novel unknown pathway in a manner not able to be duplicated by other inventions, the very sequence of events defined in this specification activates programmed cell death in the cancer cells and as such, presents a valid model for further study. In other words, through processes known to those of skill, the very core molecular event leading to the over 90% kill rate, can be explored because we have the working model to induce such events. Therein, the invention is also claimed as an important model for further research, study and pathway illumination/elucidation.

Although above and below I have shown specific experimentation and data, one of skill in the art of cancer preclinical and clinical protocol structure, execution and analysis will recognize upon reading this document, through variation of the dosages of the named components, the order in which they are applied and the time frames between applications, valid substitutions of the named components there are a myriad of variable applications which may result in the same or similar outcome. To the extent that these variables can be applied to any cancer in any mammal, the inventor notes than nothing contained within this document or any subsequent documentation provided by the inventor is intended to be limiting. The inventor also notes that this specification is intended to work alone, and reduce cytotoxic effects of traditional cancer therapy, such as chemotherapy and radiation, however, nothing herein is intended to limit the use of this specification to the extent that chemotherapeutic and radiation combination therapies can be utilized in combination with this specification. Further, that the use of chemotherapy and radiation therapy combinations, in conjunction with this specification, may reduce the cytotoxicity of the chemotherapy or radiation therapy because the dosages of the chemotherapy and radiation therapy can be reduced when used in combination with this specification. And finally, that the named specification may further sensitize cancer cells selectively over normal cells such that subsequent application of chemotherapy and radiation, as well as combination chemo/radiation therapies, will work more efficiently again, allowing for the reduction of chemotherapy and radiation and combination chemo/radiation dosages.

The foregoing description of the present specification provides illustration and description, but is not intended to be exhaustive or to limit the specifications to the precise one disclosed. Modifications and variations consistent with the above teachings may be acquired from practice of the specification. Thus, it is noted that the scope of the invention is defined by the claims and their equivalents.

The present specification will now be illustrated in more detail in the following examples. It is to be understood that these examples serve only to describe the specific embodiments of the present specification, but do not in any way intend to limit the scope of the claims. It is of further note to one of skill that unique sequence data has been provided in this application. To the extent that each of these new sequence data represent novel targets for the development of cancer therapeutics, nothing contained herein is intended to be limiting. Said targets are noted as potential targets for further development under this application using the above methods and other methods known to those of skill. Although not mentioned in this specification elsewhere, use of radiation as a distinct step, or other small molecule drugs, DNA, RNA, siRNA and all other methods for cancer therapy known to those of skill are noted as possible adjuvant to these protocols.

VI. EXAMPLES

Example 1

Synergistic inhibition of NF-KAPPAB activity

Overview: Normally, NF-kappaB activity is measured by reporter assay, electronic gel mobility shift assay and more recently, DNA binding ELISA. However, all of these methods employ exogenous DNA oligo or constructs carrying consensus NF-kappaB response element sequences for measuring specific NF-KAPPAB DNA binding and transcriptional activity. Additionally, the NF-KAPPAB consensus response element is different from the real promoter sequences that also need complex interaction with multiple molecules and may introduce artificial effects.

Method: UM-SCC-6 cells were transfected with effectene (Qiagen) i) 20% dominant negative IKK1-KA (K44A) and 80% pUC19, ii) 20% dominant negative IKK2-KA (K44A) and 80% pUC19, iii) 20% dominant negative IKK1-KA (K44A), 20% dominant negative IKK2-KA (K44A) and 60% pUC19, iv) 20% pcDNA3 and 80% pUC19 as negative control, for 72 hours. At the end of transfection, cells were lysed with lysis solution from GeneSpectra kit (Panomics). The IκBα, p100, CSNK2B mRNA levels were measured with the GeneSpectra kit. The expression levels of each transcript from different transfections were normalized by their 18sRNA level as measured at the same time.

Previously, we observed partial inhibition of NF-KAPPAB reporter activity by ~50% caused by cotransfection of kinase dead K44A-IKK1 or K44A-IKK2 into UM-SCC-6 cells and other head and neck squamars carcinoma cells. By measuring expression levels of endogenous NF-KAPPAB downstream gene, IκBα, p100 and CK2β, as an indicator of NF-KAPPAB activity, we observed little inhibitory effect on NF-KAPPAB activity from K44A-IKK1 transfected cells (~20%) and no inhibitory effect from K44A-IKK2 transfected cells. In contrast, when inhibiting both IKK1 and IKK2 molecules by cotransfecting dominant negative K44A-IKK1 and K44A-IKK2 simultaneously, we observed ~90% inhibition at all three target gene expression levels that we measured (FIGS. 2 A and B). These data showed synergistic inhibitory effect of combination of K44A-IKK1 and K44A-IKK2 on constitutive NF-KAPPAB activity in these cancer cells, suggesting potential interchangeable function between these two IKKs.

Example 2

Simultaneous Inhibition of IKK1 and IKK2 Also Lead to Cancer Cell Death

In addition to the inhibition of NF-KAPPAB activity, cell death associated with cotransfection of K44A-IKK1 and K44A-IKKβ into UM-SCC-6 cells (FIG. 3). 48 hours after tranfection, K44A-IKK1 and K44A-IKK2 co-transfected cells showed 85% reduction in cell number (FIG. 3 WST-1 no) and dramatic cell death (FIG. 3B). The data represents the average of 7 sets of duplicates. This result indicates that inhibition of NF-KAPPAB activity does lead to cancer cell death and that this can be reached only by inhibiting both IKK1 and IKK2 simultaneously. In addition, adding tetrazolium dye WST-1r further enhanced cancer cell death caused by double inhibition of IKKs (FIG. 3 WST-1-yes). Following inhibition of both IKK1 and IKK2 treating cells with WST-1r further enhance cell death (FIG. 3 WST-1-yes). In FIG. 3A about 80% reduction of cell number in K44A-IKK1 and K44A-IKK2 cotransfected cells and over 95% reduction when these cells were treated with WST-1 in addition to cotransfection of K44A-IKK1 and K44A-IKKβ. Data represents an average of 7 sets of duplicates. FIG. 3B shows cell death from double transfected cells, partial cell death from K44A-IKK1 or K44A-IKK2 single transfected cells and further enhanced cell death by adding WST-1r treatment to K44A-IKK1 and K44A-IKK2 double trasfected cells.

Example 3

WST-1 promote HT1080 human sarcoma cell death by combination with DNA Transfection and IKK Inhibitor Treatment Methods: HT1080 cells were cultured in 96 well plates and transfected with one of the pUC19, pcDNA3, IKK1-KA, IKK1-KA+PUC19, or pcDNA3+pUC19 DNA vectors for 24 hours followed with treatment of IKK Inhibitor IIII at 3-30 µM for another 24 hours and, then, treated with 10% WST-1 for 4 hours and cultured overnight before detection. The same treatments of cells were measured at 24, 48 and 96 hours after WST-1 treatment. Cell viability was measured by Cell Count Kit 8 (CCK8).

Data showed (1) significant IKK inhibitor III dose dependent induction of cell death from the cells that were transfected with any of the DNA vectors at 24, 48 and 96 hour after WST-1 treatment comparing to non transfected control cells, but no significant difference between pUC19 vector only from IKK1-KA vector (FIG. 4); (2) further induced cell death and decreased cell survival detected from the cells that were treated with WST-1 at 24, 48 and 96 hours after WST-1 treatment comparing to those with no WST-1 treated cells; (3) at 96 hours after the treatment of WST-1 all the non transfected cells grow back to the same amount as the untreated control, while partial recovery of the cells from no WST-1 treated, but transfected cells; and (4) at 96 hours after all the treatment, only the cells transfected and also treated with WST-1 remained died with no recovery, which indicated the combination of either IKK inhibitor and/or DNA transfection with the WST-1 treatment further synergize these cancer cells to 100% death. The difference in the absorption at 24 hour after WST-1 treatment were caused, in partial, by decreased response from the WST-1 treated cells to the CCK8 detection. This effect reduced in 48 hours after the removal of WST-1 treatment and diminished at 96 hours after the removal of WST-1 treatment. Morphology examination of the cells found that at 24 hours after the WST-1 treatment majority of the 30 µM IIKK inhibitor III treated cells died after the treatment. However, the survival cells that were not treated with WST-1 grow back up again. Conversely, the deaths of all the cells that were transfected with DNA vectors and with the same IKK inhibitor III treatment and treated with WST-1 were 100%. These data demonstrate the effect of WST-1 enhances the IKK inhibitor III induce cancer cell death effect and promote cell death of these cells and that pUC19 vector also contribute to the combined effect of inducing cell death.

Example 4

IFN Substitute Puc19 Transfection to Enhance IKK Inhibitor III and WST-1 Effect

Overview: Our previous data suggest that DNA transfection plays a role in the triple combination treatment for synergistic cancer cell death. Moreover, Interferon (IFN) responses have been reported to be involved in transfection effects. We examined whether IFN can be a substitute for the DNA transfection effect for in vivo treatment.

Methods: HT1080 cells were cultured in 96 well plates and treated with IFN, IKK inhibitor III and WST-1 sequentially. Each set of the cells were treated with one of the IFN members at the concentration ranging from 2-1000 units/ml for 24 hours followed by IKK inhibitor III treatment at concentration of 3-30 µM for another 24 hours and, then, with WST-1 for 4 hours and cultured overnight before detection. Cell viability was measured by CCK8 kit at 24 and 48 hours after WST-1 treatment. Total of 15 IFNs were tested. They arewer IFNαA, IFNαB, IFNαC, IFNαD, IFNαF, IFNαG, IFNαH, IFNαI IFNαJ, IFNαK, IFNα4b, and IFNαWA, IFNβ, IFNγ and IL-6.

Representative data (FIG. 21) showed IFN dose dependent and IKK Inhibitor III dependent decrease of cell growth and enhancement of cell death comparing to that without IFN treatment. Comparing to pUC19 DNA transfection, which synergized the inhibition of cell growth and promotes cell death, IFN reached 80-90% inhibitory effects caused by pUC19 DNA transfection when combined with 30 µM BMS345541 and WST-1 at 48 hours after WST-1 treatment.

Example 5

WST-1 induces ROS Generation

Overview: WST-1 was first described by ishiyama et al in 1996 (Ishiyam M, et al Biol Pharm Bull 1996, 19:1515-20). It is a cell proliferation detection reagent manufactured by Roche. WST-1 is composed of tetrazolium salt WST-1 {4-[3-(4-Iodophenyl)-2-(4-nitrophenyl)-2H-5-tetrazolio]-1,3-benzenedilsulfonate} and an electron coupling reagent diluted in phosphate buffered saline. WST-1 can be cleaved by mitochondrial succinate-tetrazolium-reductase system. This cleavage has been used as the basis of the measurement of live cell. However, WST-1 has been found impermeable to cell membrane and their reduction occurs at the cell surface or at the level of the plasma membrane via trans-plasma membrane electron transport (Berridge, MV et al, Biotechnol Annu Rev, 2005; 11:127052). Alternatively, WST-1 can be reduced by cell surface NAD(P)H-Oxidase (Berridge, M V, et al, Antioxid Redox Signal, 2000, 2:231-42, Scalett, D J, et al, Biofactors, 2004, 20:199-206) In the present invention WST-1 has been found to synergize the inhibitory effect on cell growth and promote cancer cell death when it is used in combination with at least one of the DNA transfection, or IFN, or siRNA transfection and one of the IKK, or combination of CK2 and GSK3β inhibitors. Theoretically, it has been proposed that the balance between JNK activation and NF-KAPPAB activity determines cell faith to death or a live. Prolonged JNK activation induces programmed cell death. Generation of ROS induces JNK activation while NF-KAPPAB activity leads to suppress ROS level (Luo, J L, et al, J. Clin. Invest, (2005) 115:2625-32, Shen, H M, et al, Free Radical Biology & Medicine 2006, 40:928-939). The present invention has found that WST-1 induces ROS production in these cancer cells and promotes cell death.

Methods: HT1080 cells were cultured in cover slices and transfected with pUC19 and treated with IKK inhibitor III in sequential. Following these treatment, the cells, thus, treated, were either labeled with CM-H2-DCFDA, a fluorescence dye that can labeling ROS in cells, and, then, treated with WST-1 for 30 minutes (FIG. 23A) or treated with WST-1 for 2 hours and then labeled with CM-H2-DCFDA (FIG. 23-B). The results were recorded by a digital camera with Spotlight software. Manuel exposure levels were used to maintain the same exposure level for comparison.

In both experiments, significant WST-1 induced ROS generation has been documented (FIGS. 23 A and B). In FIG. 23-A, we also observed IKK inhibitor III dose dependent labeled ROS from the cells that were transfected with pUC19, and treated with IKK, but with no exposure to WST-1. This may suggest that IKK Inhibitor III may also induce ROS generation.

Example 6

LiCl+Apigenin Induced Synergized Cancer Cell Death, WST-1 Enhance Further these Cell Death Overview: LiCl is known to inhibit GSK3β activity and Apigenin is a multi signal transducer that inhibits multiple signaling processes, including protein kinase 2 (CK2). The activity of both GSK3β and CK2 are known to enhance constitutive NF-κB activity. This test was intended to examine whether combination of LiCl and Apigenin can substitute DNA transfection for the synergistic inhibitory effect and induction of cancer cell death.

Methods: UM-SCC-6 cells were cultured in 96 well plates and treated with LiCl (1, 3, 10, 30, 100 mM) and Apigenin (1, 3, 10, 30, and 100 µM) in different combination of their doses for 24 hours followed by WST-1 treatment. Cell viability was measured with CCK8 kit.

Data showed that combination of LiCl and Apigenin dose dependent decrease of cell growth and increased cell death comparing to untreated control cells. 10 µM AP and 100 mM LiCl showed synergistic increase of cell death (FIG. 5A). The subsequent treatment of WST-1 further enhanced this inhibitory effect (FIG. 5B).

Example 7 pUC19 DNA Transfection Synergize Chemotherapeutic Drug Effect in UM-SCC6 Cells

UM-SCC-6 cells were transfected with pUC19 DNA, pcDNA3, pUC19+pcDNA3, IKK1-KA+pUC19, IKK2-KA+pUC19, and IKK1-KA+IKK2-KA+pUC19, IKK1-KA+pcDNA3, IKK2-KA+pcDNA3, or IKK1-KA+IKK2-KA+pcDNA3, for 48 hours and, treated with variable doses of 5-FU (FIG. 6A) or Cis-Platinum (FIG. 6B) for 96 or 72 hours respectively. Cell viabilities were measured in 72 and 96 hours respectively after drug treatment. Data showed that pUC19 transfected cells showed the strongest inhibitory effects on cell growth.

Example 8 pUC19 DNA Transfection Synergize Chemotherapeutic Drug Effect in HT1080 Cells

HT1080 Cells were transfected with pUC19 DNA, pcDNA3, pUC19+pcDNA3, IKK1-KA+pUC19, IKK2-KA+pUC19, and IKK1-KA+IKK2-KA+pUC19, IKK1-KA+pcDNA3, IKK2-KA+pcDNA3, or IKK1-KA+IKK2-KA+pcDNA3, for 48 hours before the treatment of chemotherapy drugs at various doses. Cell viability was measured in 72 and 96 hours after drug treatment.

Drug treatment: Cis-Platinum 30 ng/ml-3 µg/ml (FIG. 6D), Paclitaxel 1 nM-10 µM (FIG. 6C), 5-FU 50 nM-500 µM (data not shown), Doxorubicin 30 nM-3.3 µM (data not shown).

Variable enhancement and synergistic effects were shown by the transfection of these DNA vectors. pUC19 DNA alone transfection showed the strongest synergistic efficacy effect to this chemotherapy drugs comparing to other DNA vectors tested. IC50 of the drugs were lowered approximately 10 fold when combining pUC19 DNA transfected cells to that of untransfected cells of drug treatment (IC50 of Cis-Platinum from HT1080 cells and UM-SCC-6 cells untransfecte control 3 µg/ml, pUC19 transfected cells 0.3 µg/ml and 1 µg/ml respectively; IC50 of 5-FU from untransfected UM-SCC6 cells was more than 1 mM, but 200 µM from pUC19 transfected cells; IC50 of texal from pUC19 transfected HT1080 cells was 20 nM, while untransfected did not show any response upto 100 nM.). Furthermore, at 96 hours after of the cis-Platinum or palitaxel treatment untransfected cells recovered and grown up while the cell death from DNA transfected cells, especially pUC19 vector alone transfected cells were irreversible, meaning they were 100% died. These data suggest that these chemotherapy drugs inhibit cancer cell growth, but may not kill these cells. The combination of transfection of pUC19 DNA promote cell to death.

Example 9

Combination Treatment of Apigenin with WST-1r Synergizes Induced Cancer Cell Death Method: UM-SCC6, MDA-MB-231, Cal27, HT1080, T294, B6-5 and A431 cells were treated with 3% or 10% of WST-1r or 10, 30, or 100 µM apigenin or combination of variable concentrations of WST-1r with apigenin in parallel with untreated control cells and DMSO control for 4 hours, then, the treatments were removed and the cells, thus, treated were changed to normal growth medium and maintained in culture for another 24 hours. DMSO was used as vehicle control. Cell viabilities were measured by CCK8 Kit and normalized to % of untreated control calls.

Result: DMSO treated cells of every tested cell line showed same levels of cell viability as untreated control cells (data not shown).

A: UM-SCC6, MDA-MB-231, Cal27, HT1080, T294, B6-5 and A431 cells were treated with 3% of WST-1r or 100 µM apigenin or combination of 3% WST-1r with 100 µM apigenin in parallel with untreated control cells. Date showed that the combination of WST-1r and apigenin induced 75% to 95% cell death of all seven tested cancer cell lines comparing to untreated controls (FIG. 8A).

B-E: Data showed both WST-1r and apigenin dose dependent cell death and synergized cell death effect when combining 3% WST-1r with 100 µM apigenin or 10% WST-1r with 30 µM apigenin. B & C: WST-1r Dose-Response of MA-MB-231 cells (B) and A431 cells (C). The IC50 of WST-1r in the presence of 100 µM apigenin were 1% for both MDA-MB231 cells and A431 cells, while treatment of apigein alone showed little effect on cell survival. D & E: apigenin Dose-Response of MDA-MB-231 cells and A431 cells. The apigenin IC50 in the presence of 10% WST-1r were 10 µM for both cell lines (FIG. 8 B-E).

Example 10

Comparison of cell responses to modified WST-1r and Apigenin combination treatment between cancer cells and non-cancer cells. UM-SCC6, Cal27 human head and neck cancer cell lines and primary cultured human bronchia keratinocytes (HEKa) as labeled were treated with 10% modified WST-1r (mPMS 20 µM, WST-1c 1 mM) with (WST-1r 10) or without (WST-1r 0) 10% modified WST-1r in combination with 0 (Apigenin 0), 30 (Apigenin 30) or 100 (Apigenin 100) µM Apigenin for 4 hours, then, changed to apigenin in the corresponding concentrations for another 24 hours. Data showed that each of the WST-1r and the Apigenin single agent treatment had little effect on cell viabilities (FIG. 9). Combination of WST-1r with 100 µM Apigenin resulted in synergistic cell death in both UM-SCC6 and Cal27 cancer cell lines, but not in paired non-cancer primary cultured HEKa cells (FIG. 9). These data demonstrated the cancer cell specificity of this combination treatment.

Example 11

Time Course and Dose Response of WST-1r and Dose-Response of Apigenin Involved in the Combination Treatment of WST-1r with Apigenin Methods: Cal27 (A), HT1080 (B) and UM-SCC6 (C) cells were treated with variable concentration (1%, 3% and 10%) of WST-1r as indicated for 0.5, 1, 2, and 4 hours in combination with varible doses of apigenin (3, 10, 30 and 100 µM) as indicated and, then, treated with the same concentration of apigenin for another 24 hours. Cell viabilities were measured by CCK8 Kit and normalized as % of that of untreated control calls.

Results: Data showed WST-1r time and dose dependent and apigenin dose dependent cell death from all three tested cell lines (FIG. 10A-C). Synergetic induction of cell death (over 80%) occurred at 10% WST-1r treatment for 0.5 hour in combination with 100 µM apigeinin treated Cal27 and UM-SCC6 cells (FIG. 10A, C) and at 3% WST-1r treatment for 1 hour in combination with 100 µM apigeinin treated HT1080 cells (FIG. 10B). By increasing WST-1r treatment time, 80-90% cell death can be reached at 30 µM apigenin in combination with 4 hour 10% WST-1r treatment from HT1080 and UM-SCC6 cells (FIGS. 10B&C) and at 30 µM apigenin in combination with 1 hour 10% WST-1r treatment from Cal 27 cells (FIG. 10C). (Ap=apigenin; uM=µM)

Example 12

Effect of Combination Treatment with IKK Inhibitor and WST-1r on Melanoma Cell Lines Method: SK-Mel-5 and T294 human melanoma cells were treated with WST-1r at 1% and 3% final concentration respectively as indicated for 4 hours, then, removed WST-1r by changing to normal growth medium and added IKK inhibitor III for another 24 hours. After 24 hours treatment with 3 µM and 10 µM IKK inhibitor III respectively as indicated, cells were changed to grow in normal growth medium for 48 hours before measuring cell viability by CCK8 Kit.

Result: Both SK-mel-5 cells (FIG. 11A), and T294 cells (FIG. 11B) showed WST-1r and IKK inhibitor BMS345541 dose dependent increase of cell deaths. Combination of 3% WST-1r and 10 µM BMS345541 further synergized the induction of cell (FIGS. 11A&B). Whereas, the non-cancer primary cultured human keratinocytes were resistant to this combination treatment (FIG. 11C).

Example 13

Effects of Treatment Order of WST-1r and IKK Inhibitor III (BMS345541) on Inducing Human Melanoma Cell Death Method: T294 cells were treated with 3% of WST-1r in combination with 3 or 10 µM BMS345541 respectively in different order as indicated. Cell viabilities were measured by CCK8 Kit and normalized as % of that of untreated control calls. Control: Cells were either untreated or treated with BMS345541 only at the indicated doses for 24 hours and, then, changed to normal growth medium for another 24 hours before measuring cell viability. B→W: Cells treated with BMS345541only at the indicated doses for 24 hours and, then, added WST-1r at 3% final concentration for 4 hours, then removing the treatment and changed to normal growth medium for another 24 hours before measuring cell viability. W+B: Cells treated with 3% WST-1r and BMS345541 at the indicated doses for 4 hours and, then, removing the treatment and changed to normal growth medium for another 24 hours before measuring cell viability. W+B→B: Cells treated with 3% WST-1r and BMS345541 at the indicated doses for 4 hours and, then, removing the treatment and added BMS345541 at the indicated doses in normal growth medium for another 24 hours before measuring cell viability. W→B: Cells treated with 3% WST-1r for 4 hours and, then, removing the treatment and added IKK BMS345541 at the indicated doses in normal growth medium for another 24 hours before measuring cell viability.

Result: Data showed that W→B and W+B→B treatment orders synergized induction of cell death (FIG. 12).

Example 14

WST-1r and Apigenin Combination Treatment Induced JNK Phosphrylation

Method: UM-SCC6 cells were treated with WST-1r and apigenin at the indicated doses for 4 hours, and then phosphorylated JNK and total JNK were measured in parallel with FACE Kit (Qiogen). The resulting data were normalized to total cell number measured by crystal violet staining The phosphorylated JNK from each measurement were normalized to the ratio of phosphorylated JNK over total JNK values.

Result: Data showed WST-1r and apigenin dose dependent induction of phosphorylation of JNK in UM-SCC6 cells (FIG. 13). Combination of WST-1r and apigenin further increased JNK phosphorylation. The most significant increase of JNK phosphorylation from UM-SCC6 cells occurred at the treatment of 100 μM apigenin in combination with 3% or 10% WST-1r. This result supports the hypotheses that the combination of WST-1r with apigenin treatment induced JNK activation.

Example 15

Dose Response of ROS Generation after Combination Treatment of WST-1r and Apigenin and IKK Inhibitor III Method: UM-SCC6 cells were labeled with 10 μM CM-H2-DCFDA for 15 minutes and then treated with WST-1r or CCK8 at the indicated amounts in combination with variable doses of apigenin (A) or IKK Inhibitor III (B) for 4 hours. Fluorescence at Ex485/Em535 were measured for detecting ROS generation that labeled by the CM-H2-DCFDA.

Result: Data showed WST-1r dose dependent induction of ROS generation (FIGS. 24A and B). On the other hand, CCK8 induced low and very limited level of ROS generation with no relation to the CCK8 treatment dose at 4 hours after the treatment. Apigenin alone showed no effect on ROS generation. However, combination of apigenin with 1% and 3% WST-1r did show apigenin dose dependent, limited, but, steady increase on ROS generation from thus treated cells when comparing to that of the corresponding doses of WST-1r only treated cells. (FIG. 24-A) Conversely, combination of 10% of WST-1r with apigenin resulted in decrease of ROS levels(FIG. 24-B). In addition, when combined with CCK8, apigenin also increase the ROS generation(FIG. 24-A). This effect is apigenin dose dependent.

Similarly, IKK inhibitor III alone and combination of WST-1r with IKK inhibitor III (FIG. 24-B) showed similar effect as apigenin did, where 5 μM IKK Inhibitor increased ROS levels while 10 μM IKK Inhibitor III decreased it (FIG. 24-B). However, IKK Inhibitor III had no combined effect with CCK8 on ROS levels.

Example 16

Time Course of ROS Generation after Combination Treatment of WST-1e and Apigenin and IKK Inhibitor III Method: UM-SCC6 cells were labeled with 10 μM CM-H2-DCFDA for 15 minutes and then treated with WST-1r (B & D) or CCK8 (A & C) at the indicated amounts in combination with variable doses of apigenin (C & D) or IKK inhibitor III (A & B) for the time period from 15 minute up to 4 hours. At each time points as indicated, fluorescence at Ex485/Em535 were measured for detecting ROS generation that labeled by the CM-H2-DCFDA.

Result: Data showed that WST-1r induced ROS generation continued increase and lasted at least for more than 4 hours (FIG. 7-B & D), whereas, CCK8 only induced low level and transience increase of ROS(FIG. 7-A & C).

Example 17

CCK8-XTT-WST-1 Comparison

Comparison cell death inducing capability of CCK8 and XTT to WST-1r in combination with apigenin treatment Method: HT1080 and UM-SCC6 cells were treated with 10% of WST-1r, CCK8 or XTT in combination with variable doses of apigenin for 4 hours and, then changed to normal growth medium for another 24 hours. Cell viability was measured with CCK8 kit.

Result: Data showed that CCK8 had no effect on cell death when comparing to control cells, while XTT showed intermediate induction of cell death effect comparing to WST-1r on both UM-SCC6 (FIG. 14B) and HT1080 cells (FIG. 14A). Apigenin 1050 of WST-1r and, XTT treated UM-SCC6 cells were 5 and 25 μM while apigenin only and CCK8+apigenin treatments did not reached 1050. Similar result from HT1080 cells as well.

Example 18

Effects of Other Tetrazolium Salts as Substitutives of WST-1r for Combination Treatment Method: HT1080 and UM-SCC6 cells were treated with 1 mM WST-1, 0.4 mM WST-3, 0.5 mM WST-4, 0.5 mM WST-5 or 0.12 mM mPMS alone or each of the WST-3, WST-4, and WST-5 at the same concentration in combination with 0.12 mM mPMS (0.4 mM WST-3+0.12 mM mPMS, 0.5 mM WST-4+0.12 mM mPMS, 0.5 mM WST-5+0.12 mM mPMS) plus 10, 30 or 100 μM apigenin for 4 hours and, then changed to normal growth medium for another 24 hours. Cell viability was measured with CCK8 Kit.

Result: Data showed that WST-3 alone, WST-3+mPMS and WST-4+mPMS in combination with apigenin showed similar synergistic effect on inducing cell death that equivalent to that WST-1r does from both HT1080 cells (FIG. 17A) and UM-SCC6 cells (FIG. 17B). WST-1, WST-4, and WST-5 alone showed no such effect (FIG. 17 A,B). WST-3+mPMS are more potent than WST-1r on cell death induction.

Example 19 mPMS Dose-Response

Method: A & B: HT1080 (FIG. 16A) and UM-SCC6 (FIG. 16B) cells were treated with variable concentrations of mPMS as indicated in combination with 1 mM WST-1c and 10, 30 or 100 μM apigenin for 4 hours and, then, changed to normal growth medium for another 24 hours. Cell viabilities were measured by CCK8 Kit. 1 mM WST-1 only, 0.12 mM mPMS only and 10% WST-1r were used as parallel control. AP 0: Untreated Control, AP 10: 10 μM Apigenin, AP 30: 30 μM Apigenin, AP 100: 100 μM Apigenin.

Result: Data showed mPMS and apigenin dose dependent cell death of both HT1080 and UM-scc6 cells (FIGS. 16A &B). mPMS1050 of combination treatment of apigenin 100 μM and mPMS+WST-1 from HT1080 cells was 5 mM verses 60 mM from untreated control cells. mPMS1050 of combination treatment of apigenin 100 μM and mPMS+WST-1 from UM-SCC6 cells was 30 μM verses 80 μM from untreated control cells.

Example 20

Differential Cellular Responses to mPNS Treatment

Non cancer human keratinocyte (HEKa), SK-Mel-5 human malonoma cell line (SK5), human head and neck cancer cell Cal27 line (Cal27) and UM-SCC6 line (SCC6) cells and human soft tissue sarcoma cell line HT1080 (HT1080) were treated with 30, 40 or 50 μM mPMS for 4 hours and then cultured in normal growth medium for another 24 hours. Cell viabilities were measured with CCK8 kit. Data showed mPMS dose dependent cell death and differential sensitivities to mPMS treatment from each of the cell lines (FIG. 17). Among those, the non cancer primary cultured HEKa cells showed the least sensitivity to mPMS treatment with IC50 50 µM, while the 1050 from Cal27, UM-SCC6 and HT1080 cells were 20, and 30 µM respectively.

Example 21

Effect of Combination Treatment of WST-3 with Apigenin on Induction of Cancer Cell Death Method: UM-SCC6, HT1080, Cal27, SK-Mel-5, and HEKa cells were treated with 50 or 100 µM WST-3 or 10 or 30 µM apigenin alone, or combination of WST-3 and apigenin at different concentrations for 4 hours with untreated cells as control, then, changed to normal growth medium and remained culture in this medium for another 24 hours. After the 24 hours culture, cell viabilities were measured with CCK8 Kit. Data were normalized to % of untreated control cells.

Result: A: Summary of differential cell responses to WST-3, apigenin and combination treatments. Comparing to untreated cells (Ctrl) treatment of 50 mM WST-3 (WST-3) or 30 µM apigenin (Apigenin) alone showed no or limited effect of cell death to all tested cell line. Combination of WST-3 and apigenin (Apigenin+WST-3) resulted in synergistic cell death of SK-Mel-5, Cal27, UM-SCC6 and HT1080 all four tested human cancer cell lines, but limited cell death from non cancer human keratnocytes (FIG. 18A).

B & C: Comparison of Dose-Response of WST-3 and apigenin between non cancer HEKa and human melanoma cell line SK-Mel-5 cells. Data showed both WST-3 and apigenin induced and dose dependent but limited cell death from both HEKa cells (FIG. 18B) and SK-Mel-5 (FIG. 18C) cells. HEKa cells showed limited cell death in response to apigenin or WST-3 alone treatment. WST-3 IC50 of combination of 30 µM apigenin and WST-3 was 40 µM. Further increase WST-3 concentration showed no more cell death from HEKa cells (FIG. 18B). However, the SK-Mel-5 cells showed synergistic cell death response to combination treatment of 50 µM WST-3 and 30 µM apigenin. The WST-3 IC50 from this combination treatment of the SK-Mel-5 cells was 20 µM, one fold less than that from HEKa cells (FIG. 18C). The HEKa cells were much more resistant to this combination treatment. Similar results were also observed from other cancer cells.

Example 22

Effect of Substitution of WST-1r with WST-3+mPMS for Combination Treatment with Apigenin on Induction of Cell Death Method: UM-SCC6, HT1080, Cal127, SK-Mel-5, and HEKa cells were treated with 0.1 mM WST-3 plus 30 µM mPMS, or WST-3 only, or untreated control in combination with 10 or 30 µM apigenin for 4 hours and, then, changed to normal growth medium and remained culture in this medium for another 24 hours. After the 24 hours culture, cell viabilities were measured with CCK8 Kit. Data were normalized to % of untreated control cells.

Result: Data showed that over 90% induced cell death observed from thus treated Cal27, UM-SCC6, and SK-Mel-5 cells that were treated in combination of 0.1 mM WST-3, and 30 µM apigenin (FIG. 19C). Adding 30 µM mPMS to these treatments further synergize the cell death from Cal27 and UM-SCC6 cells (FIG. 19C). On the other hand, under this treatment condition, HEKa, primary cultured human keratinocytes, were relative resistant to this treatment. This difference in sensitivity to this combination treatment may provide a window for differentiating targeting cancer cells and to control toxicity to normal cells.

Example 23

Enhancement of Taxel Efficacy Effects by Combination of Puc19 DNA Sequence Derived siRNA with Taxel Method: HT1080 cells transfected with siRNAs that were derived from Puc19 DNA sequence and the siRNAs that targeting the corresponding genes that are the targets of the Puc19 derived siRNAs for 24 hours, then, treated with Taxel at 3, 10, 30, and 100 nM for 48 hours. After the 48 hours of Taxel treatment, cells in culture were changed to normal growth medium for 24 to 72 hours. Cell viability was monitored by CCK8 Kit every 24 hours. Data are normalized to % of untreated control cells. The siRNAs that used for this study includes siRNA#1, siRNA#2, siRHA#3, siRNA targeting TRPC6, SH3PXD2B, C6orf108, TTBK1, MAGI3, and TMEM182 as well as combination of siRNA#2+#3, and siRNA#1+#2+#3+#4+#5 (siRNAΣ1-5).

Result: Data showed represent the measurements of 72 hours after the treatment. The cell survival data showed Taxel dose dependent cell death and enhanced cell death by Puc19 trasnfection and majority of the siRNA trasfections (FIG. 22). The IC50 of taxel (Contrl IC50: 60 nM) was reduced more than 3 fold by Puc19 DNA trasnfection (IC50: 20 nM) and by the trasnfeciton of siRNAs targeting TRPC6 (IC50: 25 nM FIG. 22A), SH3PXD2B (IC50: 20 nM FIG. 22C), C6orf108 (IC50: 20 nM FIG. 22C), TTBK1 (IC50: 35 nM FIG. 22C), MAGI3 (IC50: 20 nM FIG. 22A), and TMEM182 (IC50: 20 nM FIG. 22B), as well as by the transfection of combination of siRNA#2+#3 (IC50: 25 nM FIG. 22A), B, and siRNA#1+#2+#3+#4+#5 (IC50: 20 nM FIG. 22A-C), Over 2.5 fold IC50 decrease of taxel concentration were observed from siRNA#2 (IC50: 25 nM FIG. 22C), siRHA#3 (IC50: 25 nM FIG. 22B), and siRNA targeting SH3PXD2B (IC50: 25 nM FIG. 22C), C6orf108 (IC50: 20 nM FIG. 22C). These data demonstrated that the DAN sequences of Puc19 DNA vector code for some short functional sequences that can target and interrupt the expression levels of the corresponding genes and the cellular functions. At least the genes (TRPC6, SH3PXD2B, C6orf108, MAGI3, and TMEM182) that have been tested can be used as a target for anti-cancer drug design for enhancing the efficacy effect of chemotherapy drugs. The siRNAs targeting these corresponding genes that were identified may also be used as a tool to reach this goal. In addition, these combined treatments induce cancer cell death rather than simple inhibition of cell growth. 72 hours after treatment, the treated cells did not grow back. This feature adds to lasting effect of the treatment.

Example 24

Substitution of Puc19 with siRNA Against TMEM182 and MAGI3 for Puc19-Ikk Inhibitor-WST-1r Triple Combination Treatment Method: HT1080 cells were transfected with siRNA#3, or the siRNA targeting MAGI3, and TMEM182 that were derived from Puc19 DNA sequence and the siRNAs that targeting the corresponding genes that are the targets of the Puc19 derived siRNAs for 24 hours, then, treated with IKK inhibitor III for 24 hours followed by adding WST-1r for another 4 hour. After the 4 hours WST-1r treatment, cells in culture were changed to normal growth medium for 24 hours. Cell viability were monitored by CCK8 Kit every 24 hours. Data were normalized to % of untreated control cells. AllStar siRNA was used as negative siRNA trasnfection control. Puc19 DNA vector transfection was used as positive control.

Data label: Untreated control: 0 Ctrl, WST-1r only: 10 Ctrl, pUC19 transfected cells: 0 p9, pUC19 transfected and WST-1r treated: 10 p9, AllStar negative contrl siRNA transfected: 0 AllStar, AllStar transfected and WST-1r treated: 10 AllStar, siRNA#3 transfected: 0 siRNA#3, siRNA#3 transfcted and WST-1r treated: 10 siRNA#3, siRNAMAGI3 transfected: 0 MAGI3, siRNA MAGI3 transfcted and WST-1r treated: 10 MAGI3, siRNATMEM182 transfected: 0 TMEM182, siR-NATMEM182 transfcted and WST-1r treated: 10 TMEM182, Result: Data showed IKK inhibitor BMS345541 dose dependent cell death and that siRNA targeting MAGI3 and TMEM182 synergize the cell death (FIG. 20). At 15 µM BMS345541 incombinatoin with 10% WST-1r and either pUC19 or the siRNA trasnfection resulted in synergistic induction of cell death. Again, these data showed that targeting TMEM182 and MAGI3 may enhance effect on cancer treatment.

What is claimed:

1. A pharmaceutical composition to be administered to a mammal for treating cancer, the composition comprising a therapeutically effective amount of WST-3 (2-(4-Iodophenyl)-3-(2,4-dinitrophenyl)-5-(2,4-disufophenyl)-2H-tetrazolium) and apigenin.

* * * * *

SEQUENCE LISTING

<160> NUMBER OF SEQ ID NOS: 13

<210> SEQ ID NO 1
<211> LENGTH: 2686
<212> TYPE: DNA
<213> ORGANISM: Artificial
<220> FEATURE:
<223> OTHER INFORMATION: Cloning vector pUC19c

<400> SEQUENCE: 1

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgagctcggt acccggggat     420
cctctagagt cgacctgcag gcatgcaagc ttggcgtaat catggtcata gctgtttcct     480
gtgtgaaatt gttatccgct cacaattcca cacaacatac gagccggaag cataaagtgt     540
aaagcctggg gtgcctaatg agtgagctaa ctcacattaa ttgcgttgcg ctcactgccc     600
gctttccagt cgggaaacct gtcgtgccag ctgcattaat gaatcggcca acgcgcgggg     660
agaggcggtt tgcgtattgg gcgctcttcc gcttcctcgc tcactgactc gctgcgctcg     720
gtcgttcggc tgcggcgagc ggtatcagct cactcaaagg cggtaatacg gttatccaca     780
gaatcagggg ataacgcagg aaagaacatg tgagcaaaag gccagcaaaa ggccaggaac     840
cgtaaaaagg ccgcgttgct ggcgtttttc cataggctcc gcccccctga cgagcatcac     900
aaaaatcgac gctcaagtca gaggtggcga aacccgacag gactataaag ataccaggcg     960
tttccccctg gaagctccct cgtgcgctct cctgttccga cctgccgct taccggatac     1020 ctgtccgcct ttctcccttc gggaagcgtg gcgctttctc aatgctcacg ctgtaggtat    1080
ctcagttcgg tgtaggtcgt tcgctccaag ctgggctgtg tgcacgaacc ccccgttcag    1140
cccgaccgct gcgccttatc cggtaactat cgtcttgagt ccaacccggt aagacacgac    1200
ttatcgccac tggcagcagc cactggtaac aggattagca gagcgaggta tgtaggcggt    1260
gctacagagt tcttgaagtg gtggcctaac tacggctaca ctagaagaac agtatttggt    1320
atctgcgctc tgctgaagcc agttaccttc ggaaaaagag ttggtagctc ttgatccggc    1380
aaacaaacca ccgctggtag cggtggtttt tttgtttgca agcagcagat tacgcgcaga    1440
aaaaaaggat ctcaagaaga tcctttgatc ttttctacgg ggtctgacgc tcagtggaac    1500
gaaaactcac gttaagggat tttggtcatg agattatcaa aaaggatctt cacctagatc    1560
cttttaaatt aaaaatgaag ttttaaatca atctaaagta tatatgagta aacttggtct    1620
```

-continued

```
gacagttacc aatgcttaat cagtgaggca cctatctcag cgatctgtct atttcgttca   1680
tccatagttg cctgactccc cgtcgtgtag ataactacga tacgggaggg cttaccatct   1740
ggccccagtg ctgcaatgat accgcgagac ccacgctcac cggctccaga tttatcagca   1800
ataaaccagc cagccggaag ggccgagcgc agaagtggtc ctgcaacttt atccgcctcc   1860
atccagtcta ttaattgttg ccgggaagct agagtaagta gttcgccagt taatagtttg   1920
cgcaacgttg ttgccattgc tacaggcatc gtggtgtcac gctcgtcgtt tggtatggct   1980
tcattcagct ccggttccca acgatcaagg cgagttacat gatcccccat gttgtgcaaa   2040
aaagcggtta gctccttcgg tcctccgatc gttgtcagaa gtaagttggc cgcagtgtta   2100
tcactcatgg ttatggcagc actgcataat tctcttactg tcatgccatc cgtaagatgc   2160
ttttctgtga ctggtgagta ctcaaccaag tcattctgag aatagtgtat gcggcgaccg   2220
agttgctctt gcccggcgtc aatacgggat aataccgcgc cacatagcag aactttaaaa   2280
gtgctcatca ttggaaaacg ttcttcgggg cgaaaactct caaggatctt accgctgttg   2340
agatccagtt cgatgtaacc cactcgtgca cccaactgat cttcagcatc ttttactttc   2400
accagcgttt ctgggtgagc aaaaacagga aggcaaaatg ccgcaaaaaa gggaataagg   2460
gcgacacgga aatgttgaat actcatactc ttccttttc aatattattg aagcatttat   2520
cagggttatt gtctcatgag cggatacata tttgaatgta tttagaaaaa taaacaaata   2580
ggggttccgc gcacatttcc ccgaaaagtg ccacctgacg tctaagaaac cattattatc   2640
atgacattaa cctataaaaa taggcgtatc acgaggccct ttcgtc                  2686
```

<210> SEQ ID NO 2
<211> LENGTH: 4564
<212> TYPE: DNA
<213> ORGANISM: Homo sapiens
<220> FEATURE:
<221> NAME/KEY: CDS
<222> LOCATION: (428)..(3223)

<400> SEQUENCE: 2

```
ccgggatctt gacggagagt gcggggatg aaggcgggag ctgagggctg gagagtctct    60
gttgacatag taactcttca gctccgtctc ccttgctctc cgctcttacg cttcgctacc   120
accagcggcc ccgcctgtgc cctctctgcc cgggcgcccc agacgcatcc tcgcggggtc   180
tcctcggcct gacctgctca ggtcaagatc ctctttgcac cccccttaagt ggtgactttt   240 cccccgggcca gtgggcgagc cacttgcggc gggcgtctgc accccctgct tcaccgtcgt   300
cccctgggca ccggtctgcc caggtccagt tcggccgctg acgcgaaccc tccgcaccgg   360
gtccccgctg gaactgccca ctcggctccc ccggagcgg ggcccaggcc agtcgggcgt   420 tcccgcc atg agc cag agc ccg gcg ttc ggg ccc cgg agg ggc agt tct      469
        Met Ser Gln Ser Pro Ala Phe Gly Pro Arg Arg Gly Ser Ser
        1               5                   10 ccc cgg ggc gct gcc gga gcc gct gcg cgg cgc aac gag agc cag gac      517
Pro Arg Gly Ala Ala Gly Ala Ala Ala Arg Arg Asn Glu Ser Gln Asp
15                  20                  25                  30 tat ctg ctc atg gac tcg gag ctg gga gaa gac ggc tgc ccg caa gcc      565
Tyr Leu Leu Met Asp Ser Glu Leu Gly Glu Asp Gly Cys Pro Gln Ala
                35                  40                  45 ccg ctg cct tgc tac ggc tac tac ccc tgc ttc cgg gga tct gac aac      613
Pro Leu Pro Cys Tyr Gly Tyr Tyr Pro Cys Phe Arg Gly Ser Asp Asn
        50                  55                  60 aga ctg gct cac cgg cgg cag aca gtt ctc cgt gag aag ggg aga agg      661
Arg Leu Ala His Arg Arg Gln Thr Val Leu Arg Glu Lys Gly Arg Arg
```

```
                          65                  70                  75
tta gct aat cga gga cca gca tac atg ttt agt gat cgc tcc aca agc        709
Leu Ala Asn Arg Gly Pro Ala Tyr Met Phe Ser Asp Arg Ser Thr Ser
    80                  85                  90 cta tct ata gag gag gaa cgc ttt ttg gat gca gct gaa tat ggt aac        757
Leu Ser Ile Glu Glu Glu Arg Phe Leu Asp Ala Ala Glu Tyr Gly Asn
95                  100                 105                 110 atc cca gtg gtg cgg aag atg tta gaa gaa tgc cac tca ctc aac gtt        805
Ile Pro Val Val Arg Lys Met Leu Glu Glu Cys His Ser Leu Asn Val
                115                 120                 125 aac tgt gtg gat tac atg ggc cag aat gcc cta cag ttg gca gtg gcc        853
Asn Cys Val Asp Tyr Met Gly Gln Asn Ala Leu Gln Leu Ala Val Ala
            130                 135                 140 aat gag cat ctg gaa att aca gaa ctt ctt ctc aag aaa gaa aac ctc        901
Asn Glu His Leu Glu Ile Thr Glu Leu Leu Leu Lys Lys Glu Asn Leu
        145                 150                 155 tct cga gtt ggg gat gct ttg ctt cta gct att agt aaa ggt tat gtt        949
Ser Arg Val Gly Asp Ala Leu Leu Leu Ala Ile Ser Lys Gly Tyr Val
    160                 165                 170 cgg att gtg gaa gca att ctc agt cat ccg gct ttt gct gaa ggc aag        997
Arg Ile Val Glu Ala Ile Leu Ser His Pro Ala Phe Ala Glu Gly Lys
175                 180                 185                 190 agg tta gca acc agc cct agc cag tct gaa ctc cag caa gat gat ttt       1045
Arg Leu Ala Thr Ser Pro Ser Gln Ser Glu Leu Gln Gln Asp Asp Phe
                195                 200                 205 tat gcc tat gat gaa gat ggg aca cgg ttc tcc cat gat gtg act cca       1093
Tyr Ala Tyr Asp Glu Asp Gly Thr Arg Phe Ser His Asp Val Thr Pro
            210                 215                 220 atc att ctg gct gcc cac tgc cag gaa tat gaa att gtg cat acc ctc       1141
Ile Ile Leu Ala Ala His Cys Gln Glu Tyr Glu Ile Val His Thr Leu
        225                 230                 235 ctg cgg aag ggt gct agg att gaa cgg cct cat gat tat ttc tgc aag       1189
Leu Arg Lys Gly Ala Arg Ile Glu Arg Pro His Asp Tyr Phe Cys Lys
    240                 245                 250 tgc aat gac tgc aac cag aaa cag aag cat gac tcg ttt agc cac tcc       1237
Cys Asn Asp Cys Asn Gln Lys Gln Lys His Asp Ser Phe Ser His Ser
255                 260                 265                 270 aga tct agg att aat gcc tat aaa ggc ctg gca agt ccg gct tac ctg       1285
Arg Ser Arg Ile Asn Ala Tyr Lys Gly Leu Ala Ser Pro Ala Tyr Leu
                275                 280                 285 tca ttg tct agt gaa gat cca gtc atg acg gct tta gaa ctt agc aat       1333
Ser Leu Ser Ser Glu Asp Pro Val Met Thr Ala Leu Glu Leu Ser Asn
            290                 295                 300 gaa ctg gca gtt ctg gcc aat att gag aaa gag ttc aag aat gac tac       1381
Glu Leu Ala Val Leu Ala Asn Ile Glu Lys Glu Phe Lys Asn Asp Tyr
        305                 310                 315 aaa aaa ctg tca atg cag tgc aaa gac ttt gtt gtt gga ctc ctt gat       1429
Lys Lys Leu Ser Met Gln Cys Lys Asp Phe Val Val Gly Leu Leu Asp
    320                 325                 330 ctg tgc aga aac act gaa gaa gtc gag gcc att ctg aat ggg gat gtt       1477
Leu Cys Arg Asn Thr Glu Glu Val Glu Ala Ile Leu Asn Gly Asp Val
335                 340                 345                 350 gaa acg ctc cag agt ggt gat cac ggt cgc cca aat ctc agc cgt tta       1525
Glu Thr Leu Gln Ser Gly Asp His Gly Arg Pro Asn Leu Ser Arg Leu
                355                 360                 365 aaa ctt gcc att aaa tat gaa gta aaa aaa ttt gta gct cat cca aac       1573
Lys Leu Ala Ile Lys Tyr Glu Val Lys Lys Phe Val Ala His Pro Asn
            370                 375                 380 tgc caa cag caa ctt ctc tcc att tgg tat gag aat ctt tct ggt tta       1621
Cys Gln Gln Gln Leu Leu Ser Ile Trp Tyr Glu Asn Leu Ser Gly Leu
```

-continued

```
                385                 390                 395
cga cag cag aca atg gcg gtc aag ttc ctt gtg gtc ctt gct gtt gcc    1669
Arg Gln Gln Thr Met Ala Val Lys Phe Leu Val Val Leu Ala Val Ala
    400                 405                 410 att gga ctg ccc ttc ctg gct ctc att tac tgg ttt gct cca tgc agc    1717
Ile Gly Leu Pro Phe Leu Ala Leu Ile Tyr Trp Phe Ala Pro Cys Ser
415                 420                 425                 430 aag atg ggg aag ata atg cgt gga cca ttc atg aag ttt gta gca cac    1765
Lys Met Gly Lys Ile Met Arg Gly Pro Phe Met Lys Phe Val Ala His
                435                 440                 445 gca gcc tcc ttc acc att ttt ctg gga ctg cta gtc atg aat gca gct    1813
Ala Ala Ser Phe Thr Ile Phe Leu Gly Leu Leu Val Met Asn Ala Ala
            450                 455                 460 gac aga ttt gaa ggc aca aaa ctc ctt cct aat gaa acc agc aca gat    1861
Asp Arg Phe Glu Gly Thr Lys Leu Leu Pro Asn Glu Thr Ser Thr Asp
        465                 470                 475 aat gca aaa cag ctg ttc agg atg aaa aca tcc tgc ttc tca tgg atg    1909
Asn Ala Lys Gln Leu Phe Arg Met Lys Thr Ser Cys Phe Ser Trp Met
    480                 485                 490 gag atg ctc att ata tcc tgg gta ata ggc atg ata tgg gct gaa tgt    1957
Glu Met Leu Ile Ile Ser Trp Val Ile Gly Met Ile Trp Ala Glu Cys
495                 500                 505                 510 aaa gaa atc tgg act cag ggc ccc aag gaa tat ttg ttt gag ttg tgg    2005
Lys Glu Ile Trp Thr Gln Gly Pro Lys Glu Tyr Leu Phe Glu Leu Trp
                515                 520                 525 aac atg ctt gat ttt ggt atg tta gca att ttc gca gca tca ttc att    2053
Asn Met Leu Asp Phe Gly Met Leu Ala Ile Phe Ala Ala Ser Phe Ile
            530                 535                 540 gcg aga ttc atg gca ttt tgg cat gct tcc aaa gcc cag agc atc att    2101
Ala Arg Phe Met Ala Phe Trp His Ala Ser Lys Ala Gln Ser Ile Ile
        545                 550                 555 gac gca aat gat act ttg aag gac ttg acg aaa gta aca ttg gga gac    2149
Asp Ala Asn Asp Thr Leu Lys Asp Leu Thr Lys Val Thr Leu Gly Asp
    560                 565                 570 aat gtg aaa tac tac aat ttg gcc agg ata aag tgg gac ccc tct gat    2197
Asn Val Lys Tyr Tyr Asn Leu Ala Arg Ile Lys Trp Asp Pro Ser Asp
575                 580                 585                 590 cct caa ata ata tct gaa ggt ctt tat gca att gct gta gtt tta agt    2245
Pro Gln Ile Ile Ser Glu Gly Leu Tyr Ala Ile Ala Val Val Leu Ser
                595                 600                 605 ttc tct agg ata gct tat att tta cca gca aat gaa agc ttt gga cct    2293
Phe Ser Arg Ile Ala Tyr Ile Leu Pro Ala Asn Glu Ser Phe Gly Pro
            610                 615                 620 ctg cag ata tca ctt gga aga aca gtc aaa gac atc ttc aag ttc atg    2341
Leu Gln Ile Ser Leu Gly Arg Thr Val Lys Asp Ile Phe Lys Phe Met
        625                 630                 635 gtc ata ttc att atg gtg ttt gtg gcc ttt atg att gga atg ttc aat    2389
Val Ile Phe Ile Met Val Phe Val Ala Phe Met Ile Gly Met Phe Asn
    640                 645                 650 ctc tac tcc tac tac att ggt gca aaa caa aat gaa gcc ttc aca aca    2437
Leu Tyr Ser Tyr Tyr Ile Gly Ala Lys Gln Asn Glu Ala Phe Thr Thr
655                 660                 665                 670 gtt gaa gag agt ttt aag aca ctg ttc tgg gct ata ttt gga ctt tct    2485
Val Glu Glu Ser Phe Lys Thr Leu Phe Trp Ala Ile Phe Gly Leu Ser
                675                 680                 685 gaa gtg aaa tca gtg gtc atc aac tat aac cac aaa ttc att gaa aac    2533
Glu Val Lys Ser Val Val Ile Asn Tyr Asn His Lys Phe Ile Glu Asn
            690                 695                 700 att ggt tac gtt ctt tat gga gtc tat aat gtt acg atg gtc att gtt    2581
Ile Gly Tyr Val Leu Tyr Gly Val Tyr Asn Val Thr Met Val Ile Val
```

```
                705                 710                 715
ttg cta aat atg tta att gcc atg atc aac agt tca ttc cag gaa att    2629
Leu Leu Asn Met Leu Ile Ala Met Ile Asn Ser Ser Phe Gln Glu Ile
        720                 725                 730 gag gat gac gct gat gtg gag tgg aaa ttt gca agg gcc aaa ctc tgg    2677
Glu Asp Asp Ala Asp Val Glu Trp Lys Phe Ala Arg Ala Lys Leu Trp
735                 740                 745                 750 ttt tcc tac ttt gag gag ggc aga aca ctt cct gta ccc ttc aat ctg    2725
Phe Ser Tyr Phe Glu Glu Gly Arg Thr Leu Pro Val Pro Phe Asn Leu
                755                 760                 765 gtg ccg agt cca aag tcc ctg ttt tat ctc tta ctg aag ctt aaa aaa    2773
Val Pro Ser Pro Lys Ser Leu Phe Tyr Leu Leu Leu Lys Leu Lys Lys
        770                 775                 780 tgg att tct gag ctg ttc cag ggc cat aaa aaa ggt ttc cag gaa gat    2821
Trp Ile Ser Glu Leu Phe Gln Gly His Lys Lys Gly Phe Gln Glu Asp
                785                 790                 795 gca gag atg aac aag ata aat gaa gaa aag aaa ctt gga att tta gga    2869
Ala Glu Met Asn Lys Ile Asn Glu Glu Lys Lys Leu Gly Ile Leu Gly
800                 805                 810 agt cat gaa gac ctt tca aaa tta tca ctt gac aaa aaa cag gtt ggg    2917
Ser His Glu Asp Leu Ser Lys Leu Ser Leu Asp Lys Lys Gln Val Gly
815                 820                 825                 830 cac aat aaa caa cca agt ata agg agc tca gaa gat ttc cat cta aat    2965
His Asn Lys Gln Pro Ser Ile Arg Ser Ser Glu Asp Phe His Leu Asn
                835                 840                 845 agt ttc aat aat cct cca aga caa tat cag aaa ata atg aaa agg ctc    3013
Ser Phe Asn Asn Pro Pro Arg Gln Tyr Gln Lys Ile Met Lys Arg Leu
        850                 855                 860 att aaa aga tat gta ctg cag gcc cag ata gat aag gag agt gat gaa    3061
Ile Lys Arg Tyr Val Leu Gln Ala Gln Ile Asp Lys Glu Ser Asp Glu
                865                 870                 875 gtg aac gaa ggg gaa ctg aag gaa att aag cag gac atc tca agt ctc    3109
Val Asn Glu Gly Glu Leu Lys Glu Ile Lys Gln Asp Ile Ser Ser Leu
880                 885                 890 cgc tat gaa ctc ctt gaa gaa aaa tct cag aat aca gaa gac cta gca    3157
Arg Tyr Glu Leu Leu Glu Glu Lys Ser Gln Asn Thr Glu Asp Leu Ala
895                 900                 905                 910 gaa ctt att aga gaa ctt gga gag aaa tta tcc atg gaa cca aat caa    3205
Glu Leu Ile Arg Glu Leu Gly Glu Lys Leu Ser Met Glu Pro Asn Gln
                915                 920                 925 gag gaa acc aat aga taa tgcgaagact tccttagaaa ttcatattta            3253
Glu Glu Thr Asn Arg
                930 tttgtccact tgaagccata ttattttctg atttattttc ttaagtgcca atgggcccac   3313 cttttaaaca agaaaacgtt aaataacttg ggccatccta tcatctggag ccctagtatc   3373 taattttttt ggtgattaaa ctccattgtt cagggtaaag gctgtagata atgaggaaaa   3433 ttatgcccag ttgtttggtg cttgttttat aaactgcttt cttggatata actaactctt   3493 gtgatgatgt cattgccatg tagtgtctgc ctgaaaatgg gtcccagcgg acaggggctg   3553 acccacgtta ctccccatgc ggttttcctt ctgaagttta tttcaggttc cttcttgcct   3613 gctctgtgga tcccctgctg gggactccca gctctgaaat ttgggaaaaa gtagcccatg   3673 ggccctttaga atgctttaat cctttcttta gaatgctgtt taaacaccat ttaccctact   3733 tatccctcaa tgcacatgat tgataccgtt catacaaaat ggtcttacat ctatgtaaaa   3793 ttttctgatt catctatttg aaaacattac acttaacaat gaaaaagtt tttcctccac    3853 tgaaccctgg aaacatggtc cagttttgtg tgtgtgcgtg tgtgtaaatg tgtacacaca   3913
```

-continued

```
gacataaagt acttgccta tttagtttgt ggctaatgtg gacacacaaa agctctttat    3973
gttataaatt tttattgtca ctaaaaaatt ttactgtcta aataagtacc ttttattgga    4033
gaaaaatcaa accccaaac aaacactgtg gttgtttggt tccattatag cacaattttg    4093
tgccatttct gggagcattt acagatgaat ccccacactt agccattgaa tgtaaagggg    4153
aaaaataagg tgagaatttg taaatactta tctgttattt tcaatatgtt ctatccttct    4213
acccaaatat ataaaacagg aatttgcatt catgtgcatt taccaagagg ttgttgttgt    4273
tacttactga tcatgtgaag tggtgtctta aacaactaaa agcgatgaag gttcatatgt    4333
ttactcaaag accattggca ttcagaggat gctggacatt aactggaact gctacttcca    4393
attcaataat gggagatttc aaatgcaaat ctttaacttc atcttaaaga tgaaatggtt    4453
gcagaaaatc tgtttagctc caactttggc ttaatttaaa tcaaagaaca tttatgtaac    4513
cagatcagaa aatacagctg aaaatttgga attcgagctc ggtacccggg g            4564
```

<210> SEQ ID NO 3
<211> LENGTH: 931
<212> TYPE: PRT
<213> ORGANISM: Homo sapiens

<400> SEQUENCE: 3

```
Met Ser Gln Ser Pro Ala Phe Gly Pro Arg Arg Gly Ser Ser Pro Arg
1               5                   10                  15

Gly Ala Ala Gly Ala Ala Ala Arg Arg Asn Glu Ser Gln Asp Tyr Leu
            20                  25                  30

Leu Met Asp Ser Glu Leu Gly Asp Gly Cys Pro Gln Ala Pro Leu
        35                  40                  45

Pro Cys Tyr Gly Tyr Tyr Pro Cys Phe Arg Gly Ser Asp Asn Arg Leu
    50                  55                  60

Ala His Arg Arg Gln Thr Val Leu Arg Glu Lys Gly Arg Arg Leu Ala
65                  70                  75                  80

Asn Arg Gly Pro Ala Tyr Met Phe Ser Asp Arg Ser Thr Ser Leu Ser
                85                  90                  95

Ile Glu Glu Arg Phe Leu Asp Ala Ala Glu Tyr Gly Asn Ile Pro
            100                 105                 110

Val Val Arg Lys Met Leu Glu Glu Cys His Ser Leu Asn Val Asn Cys
        115                 120                 125

Val Asp Tyr Met Gly Gln Asn Ala Leu Gln Leu Ala Val Ala Asn Glu
    130                 135                 140

His Leu Glu Ile Thr Glu Leu Leu Leu Lys Lys Glu Asn Leu Ser Arg
145                 150                 155                 160

Val Gly Asp Ala Leu Leu Leu Ala Ile Ser Lys Gly Tyr Val Arg Ile
                165                 170                 175

Val Glu Ala Ile Leu Ser His Pro Ala Phe Ala Glu Gly Lys Arg Leu
            180                 185                 190

Ala Thr Ser Pro Ser Gln Ser Glu Leu Gln Gln Asp Phe Tyr Ala
        195                 200                 205

Tyr Asp Glu Asp Gly Thr Arg Phe Ser His Asp Val Thr Pro Ile Ile
    210                 215                 220

Leu Ala Ala His Cys Gln Glu Tyr Glu Ile Val His Thr Leu Leu Arg
225                 230                 235                 240

Lys Gly Ala Arg Ile Glu Arg Pro His Asp Tyr Phe Cys Lys Cys Asn
                245                 250                 255

Asp Cys Asn Gln Lys Gln Lys His Asp Ser Phe Ser His Ser Arg Ser
            260                 265                 270
```

```
Arg Ile Asn Ala Tyr Lys Gly Leu Ala Ser Pro Ala Tyr Leu Ser Leu
            275                 280                 285

Ser Ser Glu Asp Pro Val Met Thr Ala Leu Glu Leu Ser Asn Glu Leu
        290                 295                 300

Ala Val Leu Ala Asn Ile Glu Lys Glu Phe Lys Asn Asp Tyr Lys Lys
305                 310                 315                 320

Leu Ser Met Gln Cys Lys Asp Phe Val Val Gly Leu Leu Asp Leu Cys
                325                 330                 335

Arg Asn Thr Glu Glu Val Glu Ala Ile Leu Asn Gly Asp Val Glu Thr
            340                 345                 350

Leu Gln Ser Gly Asp His Gly Arg Pro Asn Leu Ser Arg Leu Lys Leu
        355                 360                 365

Ala Ile Lys Tyr Glu Val Lys Lys Phe Val Ala His Pro Asn Cys Gln
370                 375                 380

Gln Gln Leu Leu Ser Ile Trp Tyr Glu Asn Leu Ser Gly Leu Arg Gln
385                 390                 395                 400

Gln Thr Met Ala Val Lys Phe Leu Val Val Leu Ala Val Ala Ile Gly
                405                 410                 415

Leu Pro Phe Leu Ala Leu Ile Tyr Trp Phe Ala Pro Cys Ser Lys Met
            420                 425                 430

Gly Lys Ile Met Arg Gly Pro Phe Met Lys Phe Val Ala His Ala Ala
        435                 440                 445

Ser Phe Thr Ile Phe Leu Gly Leu Leu Val Met Asn Ala Ala Asp Arg
450                 455                 460

Phe Glu Gly Thr Lys Leu Leu Pro Asn Glu Thr Ser Thr Asp Asn Ala
465                 470                 475                 480

Lys Gln Leu Phe Arg Met Lys Thr Ser Cys Phe Ser Trp Met Glu Met
                485                 490                 495

Leu Ile Ile Ser Trp Val Ile Gly Met Ile Trp Ala Glu Cys Lys Glu
            500                 505                 510

Ile Trp Thr Gln Gly Pro Lys Glu Tyr Leu Phe Glu Leu Trp Asn Met
        515                 520                 525

Leu Asp Phe Gly Met Leu Ala Ile Phe Ala Ala Ser Phe Ile Ala Arg
530                 535                 540

Phe Met Ala Phe Trp His Ala Ser Lys Ala Gln Ser Ile Ile Asp Ala
545                 550                 555                 560

Asn Asp Thr Leu Lys Asp Leu Thr Lys Val Thr Leu Gly Asp Asn Val
                565                 570                 575

Lys Tyr Tyr Asn Leu Ala Arg Ile Lys Trp Asp Pro Ser Asp Pro Gln
            580                 585                 590

Ile Ile Ser Glu Gly Leu Tyr Ala Ile Ala Val Val Leu Ser Phe Ser
        595                 600                 605

Arg Ile Ala Tyr Ile Leu Pro Ala Asn Glu Ser Phe Gly Pro Leu Gln
610                 615                 620

Ile Ser Leu Gly Arg Thr Val Lys Asp Ile Phe Lys Phe Met Val Ile
625                 630                 635                 640

Phe Ile Met Val Phe Val Ala Phe Met Ile Gly Met Phe Asn Leu Tyr
                645                 650                 655

Ser Tyr Tyr Ile Gly Ala Lys Gln Asn Glu Ala Phe Thr Thr Val Glu
            660                 665                 670

Glu Ser Phe Lys Thr Leu Phe Trp Ala Ile Phe Gly Leu Ser Glu Val
        675                 680                 685

Lys Ser Val Val Ile Asn Tyr Asn His Lys Phe Ile Glu Asn Ile Gly
```

-continued

```
            690                 695                 700
Tyr Val Leu Tyr Gly Val Tyr Asn Val Thr Met Val Ile Val Leu Leu
705                 710                 715                 720

Asn Met Leu Ile Ala Met Ile Asn Ser Ser Phe Gln Glu Ile Glu Asp
                725                 730                 735

Asp Ala Asp Val Glu Trp Lys Phe Ala Arg Ala Lys Leu Trp Phe Ser
            740                 745                 750

Tyr Phe Glu Glu Gly Arg Thr Leu Pro Val Pro Phe Asn Leu Val Pro
        755                 760                 765

Ser Pro Lys Ser Leu Phe Tyr Leu Leu Leu Lys Leu Lys Lys Trp Ile
770                 775                 780

Ser Glu Leu Phe Gln Gly His Lys Lys Gly Phe Gln Glu Asp Ala Glu
785                 790                 795                 800

Met Asn Lys Ile Asn Glu Glu Lys Lys Leu Gly Ile Leu Gly Ser His
                805                 810                 815

Glu Asp Leu Ser Lys Leu Ser Leu Asp Lys Lys Gln Val Gly His Asn
            820                 825                 830

Lys Gln Pro Ser Ile Arg Ser Ser Glu Asp Phe His Leu Asn Ser Phe
        835                 840                 845

Asn Asn Pro Pro Arg Gln Tyr Gln Lys Ile Met Lys Arg Leu Ile Lys
850                 855                 860

Arg Tyr Val Leu Gln Ala Gln Ile Asp Lys Glu Ser Asp Glu Val Asn
865                 870                 875                 880

Glu Gly Glu Leu Lys Glu Ile Lys Gln Asp Ile Ser Ser Leu Arg Tyr
                885                 890                 895

Glu Leu Leu Glu Glu Lys Ser Gln Asn Thr Glu Asp Leu Ala Glu Leu
            900                 905                 910

Ile Arg Glu Leu Gly Glu Lys Leu Ser Met Glu Pro Asn Gln Glu Glu
        915                 920                 925

Thr Asn Arg
    930

<210> SEQ ID NO 4
<211> LENGTH: 7777
<212> TYPE: DNA
<213> ORGANISM: Homo sapiens
<220> FEATURE:
<221> NAME/KEY: CDS
<222> LOCATION: (172)..(2907)

<400> SEQUENCE: 4
agtgcgcgcc gagcgaaggg cggcggcggt ggcggcggcg gctcgtgctc ggccccggct      60
gcgattgcgc tcagctccag gttccctgcc gcggcggcg cgcccccagc gctccctgca     120
ccccgcgcca cccgcacccg cgctcggccc gctgcgggcg gaggagcggc c atg ccg     177
                                                        Met Pro
                                                          1 ccg cgg cgc agc atc gtg gag gtg aag gtg cta gac gtg cag aag cgg     225
Pro Arg Arg Ser Ile Val Glu Val Lys Val Leu Asp Val Gln Lys Arg
         5                  10                  15 cgg gtg ccc aac aag cat tat gtc tac atc atc cgg gtc acg tgg tcc     273
Arg Val Pro Asn Lys His Tyr Val Tyr Ile Ile Arg Val Thr Trp Ser
     20                  25                  30 agc ggc tcc acc gag gcc att tac cgg cgc tac agc aag ttt ttt gac     321
Ser Gly Ser Thr Glu Ala Ile Tyr Arg Arg Tyr Ser Lys Phe Phe Asp
 35                  40                  45                  50 ctc cag atg cag atg ttg gac aaa ttt ccc atg gaa gga gga cag aag     369
Leu Gln Met Gln Met Leu Asp Lys Phe Pro Met Glu Gly Gly Gln Lys
```

-continued

|  | 55 | 60 | 65 |  |
|---|---|---|---|---| gac ccc aag cag cgg atc atc ccc ttt ctg cca ggt aag att ctc ttc      417
Asp Pro Lys Gln Arg Ile Ile Pro Phe Leu Pro Gly Lys Ile Leu Phe
         70              75              80 aga cga agc cac atc cgg gac gtg gct gtc aaa cgc ctg ata cca att      465
Arg Arg Ser His Ile Arg Asp Val Ala Val Lys Arg Leu Ile Pro Ile
         85              90              95 gat gaa tac tgt aag gcc ctc atc cag ctg ccc ccc tac atc tct cag      513
Asp Glu Tyr Cys Lys Ala Leu Ile Gln Leu Pro Pro Tyr Ile Ser Gln
        100             105             110 tgt gat gag gtg ctg cag ttc ttt gag aca aga cct gag gac ctg aat      561
Cys Asp Glu Val Leu Gln Phe Phe Glu Thr Arg Pro Glu Asp Leu Asn
115             120             125             130 ccc ccc aaa gag gag cac att ggg aaa aag aaa tct ggg ggt gac caa      609
Pro Pro Lys Glu Glu His Ile Gly Lys Lys Lys Ser Gly Gly Asp Gln
                135             140             145 acc tca gtg gac ccc atg gtc ctg gag cag tat gtg gtg gta gcc aac      657
Thr Ser Val Asp Pro Met Val Leu Glu Gln Tyr Val Val Val Ala Asn
        150             155             160 tac cag aag cag gag agt tcg gag atc agc ctc agc gtg ggg cag gtg      705
Tyr Gln Lys Gln Glu Ser Ser Glu Ile Ser Leu Ser Val Gly Gln Val
        165             170             175 gtg gac atc atc gag aag aat gag tca ggt tgg tgg ttc gtc agc act      753
Val Asp Ile Ile Glu Lys Asn Glu Ser Gly Trp Trp Phe Val Ser Thr
        180             185             190 gcc gag gag caa ggc tgg gtc cct gca acg tgc ctc gaa ggc cag gat      801
Ala Glu Glu Gln Gly Trp Val Pro Ala Thr Cys Leu Glu Gly Gln Asp
195             200             205             210 ggg gtg cag gat gag ttt tct ctg cag cct gaa gaa gag gag aag tac      849
Gly Val Gln Asp Glu Phe Ser Leu Gln Pro Glu Glu Glu Glu Lys Tyr
                215             220             225 aca gtc atc tac ccg tac aca gct cgg gac cag gat gaa atg aac ctg      897
Thr Val Ile Tyr Pro Tyr Thr Ala Arg Asp Gln Asp Glu Met Asn Leu
        230             235             240 gag aga ggg gct gtg gtg gag gtc atc cag aaa aac ctg gaa ggc tgg      945
Glu Arg Gly Ala Val Val Glu Val Ile Gln Lys Asn Leu Glu Gly Trp
        245             250             255 tgg aag atc agg tac cag ggc aaa gaa ggc tgg gcc ccc gcc tcc tac      993
Trp Lys Ile Arg Tyr Gln Gly Lys Glu Gly Trp Ala Pro Ala Ser Tyr
        260             265             270 cta aag aag aac agt ggg gag ccc ttg ccc ccg aag cca ggc cct ggc     1041
Leu Lys Lys Asn Ser Gly Glu Pro Leu Pro Pro Lys Pro Gly Pro Gly
275             280             285             290 tca ccc tcc cac ccg ggt gcc ctt gac ttg gat ggt gtt tcc cgg cag     1089
Ser Pro Ser His Pro Gly Ala Leu Asp Leu Asp Gly Val Ser Arg Gln
                295             300             305 cag aac gcg gtg ggc agg gag aag gag ctg ctc agc agc cag agg gac     1137
Gln Asn Ala Val Gly Arg Glu Lys Glu Leu Leu Ser Ser Gln Arg Asp
        310             315             320 ggg cgg ttt gaa ggc cgc ccg gtg ccc gac ggt gac gcc aag cag aga     1185
Gly Arg Phe Glu Gly Arg Pro Val Pro Asp Gly Asp Ala Lys Gln Arg
        325             330             335 tca cca aag atg agg cag aga ccc cct cct cgc cgg gac atg acc att     1233
Ser Pro Lys Met Arg Gln Arg Pro Pro Pro Arg Arg Asp Met Thr Ile
340             345             350 cct cga ggc ctc aac ctg ccg aag ccg ccc atc ccg ccc caa gtg gag     1281
Pro Arg Gly Leu Asn Leu Pro Lys Pro Pro Ile Pro Pro Gln Val Glu
355             360             365             370 gaa gag tat tac acc atc gcc gaa ttc cag aca acc atc cca gac ggc     1329
Glu Glu Tyr Tyr Thr Ile Ala Glu Phe Gln Thr Thr Ile Pro Asp Gly -continued

```
                    375                 380                 385
atc agc ttc cag gca ggc ctg aag gtc gag gtg atc gag aaa aac ttg    1377
Ile Ser Phe Gln Ala Gly Leu Lys Val Glu Val Ile Glu Lys Asn Leu
            390                 395                 400 agt ggc tgg tgg tac att cag att gaa gat aag gaa ggg tgg gcc ccg    1425
Ser Gly Trp Trp Tyr Ile Gln Ile Glu Asp Lys Glu Gly Trp Ala Pro
        405                 410                 415 gcc acc ttc att gac aag tac aag aag acg agc aac gcg tcg aga ccc    1473
Ala Thr Phe Ile Asp Lys Tyr Lys Lys Thr Ser Asn Ala Ser Arg Pro
420                 425                 430 aac ttt ctg gct ccc ctg ccc cac gag gtg acc cag ctc cgg ctg ggg    1521
Asn Phe Leu Ala Pro Leu Pro His Glu Val Thr Gln Leu Arg Leu Gly
435                 440                 445                 450 gaa gca gca gcg ctg gag aac aac acg ggc agc gaa gcc acg ggc ccc    1569
Glu Ala Ala Ala Leu Glu Asn Asn Thr Gly Ser Glu Ala Thr Gly Pro
                455                 460                 465 tcc cgg ccc ctg cct gac gca ccg cat ggt gtc atg gac tcg ggg ttg    1617
Ser Arg Pro Leu Pro Asp Ala Pro His Gly Val Met Asp Ser Gly Leu
            470                 475                 480 cca tgg tct aaa gac tgg aag ggc agt aag gat gtc ctg agg aag gca    1665
Pro Trp Ser Lys Asp Trp Lys Gly Ser Lys Asp Val Leu Arg Lys Ala
        485                 490                 495 tct tca gac atg tct gcg tca gca ggc tac gag gag atc tca gac ccc    1713
Ser Ser Asp Met Ser Ala Ser Ala Gly Tyr Glu Glu Ile Ser Asp Pro
500                 505                 510 gac atg gag gag aag ccc agc ctc cct ccg cgg aaa gaa tcc atc atc    1761
Asp Met Glu Glu Lys Pro Ser Leu Pro Pro Arg Lys Glu Ser Ile Ile
515                 520                 525                 530 aag tcg gag ggg gag ctg ctg gag cgg gag cgg gag cgg cag agg acg    1809
Lys Ser Glu Gly Glu Leu Leu Glu Arg Glu Arg Glu Arg Gln Arg Thr
                535                 540                 545 gag cag ctc cgg ggc ccc act ccc aag cct ccg ggc gtg att ttg ccg    1857
Glu Gln Leu Arg Gly Pro Thr Pro Lys Pro Pro Gly Val Ile Leu Pro
            550                 555                 560 atg atg cca gcc aaa cac atc cct cca gcc cgg gac agc agg agg cca    1905
Met Met Pro Ala Lys His Ile Pro Pro Ala Arg Asp Ser Arg Arg Pro
        565                 570                 575 gag ccc aaa cct gac aaa agc aga ctg ttc cag ctg aaa aat gac atg    1953
Glu Pro Lys Pro Asp Lys Ser Arg Leu Phe Gln Leu Lys Asn Asp Met
580                 585                 590 ggg ctg gag tgt ggc cac aag gtc ttg gcc aag gaa gtg aag aag ccc    2001
Gly Leu Glu Cys Gly His Lys Val Leu Ala Lys Glu Val Lys Lys Pro
595                 600                 605                 610 aac ctc cgg ccc atc tcc aaa tcc aaa act gac ctg cca gag gag aag    2049
Asn Leu Arg Pro Ile Ser Lys Ser Lys Thr Asp Leu Pro Glu Glu Lys
                615                 620                 625 cca gat gcc act ccc cag aat ccc ttc ttg aag tcc aga cct cag gtt    2097
Pro Asp Ala Thr Pro Gln Asn Pro Phe Leu Lys Ser Arg Pro Gln Val
            630                 635                 640 agg cca aaa cca gct cct tcc ccc aaa acg gag cca cct cag ggc gaa    2145
Arg Pro Lys Pro Ala Pro Ser Pro Lys Thr Glu Pro Pro Gln Gly Glu
        645                 650                 655 gac caa gtc gac atc tgc aac ctc agg agt aag ctc agg cct gcc aag    2193
Asp Gln Val Asp Ile Cys Asn Leu Arg Ser Lys Leu Arg Pro Ala Lys
660                 665                 670 tcc caa gac aag tcc ttg ttg gat ggg gag ggc ccc cag gca gta ggg    2241
Ser Gln Asp Lys Ser Leu Leu Asp Gly Glu Gly Pro Gln Ala Val Gly
675                 680                 685                 690 ggc caa gac gtg gcc ttc agc cga agc ttc ctc cca gga gag ggg cct    2289
Gly Gln Asp Val Ala Phe Ser Arg Ser Phe Leu Pro Gly Glu Gly Pro
```

-continued

```
                    695                 700                 705
ggc cgc gcc cag gac agg acg ggc aaa cag gat ggt ctc agc cca aaa       2337
Gly Arg Ala Gln Asp Arg Thr Gly Lys Gln Asp Gly Leu Ser Pro Lys
            710                 715                 720 gag att tcc tgc aga gcc cct ccg agg cca gcc aag acc aca gat cct       2385
Glu Ile Ser Cys Arg Ala Pro Pro Arg Pro Ala Lys Thr Thr Asp Pro
        725                 730                 735 gtg tct aag agc gtg cct gtt cct ctc caa gag gct ccc cag cag aga       2433
Val Ser Lys Ser Val Pro Val Pro Leu Gln Glu Ala Pro Gln Gln Arg
    740                 745                 750 cct gtg gtc cca ccc cgc aga cca cct ccc cca aag aaa acc tct tcg       2481
Pro Val Val Pro Pro Arg Arg Pro Pro Pro Lys Lys Thr Ser Ser
755                 760                 765                 770 tca tcc agg ccg ctc cca gag gtc aga ggt cca cag tgt gaa ggc cac       2529
Ser Ser Arg Pro Leu Pro Glu Val Arg Gly Pro Gln Cys Glu Gly His
                775                 780                 785 gaa agc agg gca gct ccc acc cca ggc cgt gct ctc ctc gtc cct cca       2577
Glu Ser Arg Ala Ala Pro Thr Pro Gly Arg Ala Leu Leu Val Pro Pro
            790                 795                 800 aaa gcc aaa cct ttt ctc tcc aac tct ttg ggg ggc cag gat gac acg       2625
Lys Ala Lys Pro Phe Leu Ser Asn Ser Leu Gly Gly Gln Asp Asp Thr
        805                 810                 815 cga ggc aaa ggc agc ctg ggg cca tgg ggg acc ggc aag att gga gaa       2673
Arg Gly Lys Gly Ser Leu Gly Pro Trp Gly Thr Gly Lys Ile Gly Glu
    820                 825                 830 aac agg gag aaa gca gct gca gcc tct gtc ccc aat gcc gac ggc ctg       2721
Asn Arg Glu Lys Ala Ala Ala Ala Ser Val Pro Asn Ala Asp Gly Leu
835                 840                 845                 850 aag gac tct ttg tat gtg gcc gtg gcc gac ttt gaa gga gac aaa gac       2769
Lys Asp Ser Leu Tyr Val Ala Val Ala Asp Phe Glu Gly Asp Lys Asp
                855                 860                 865 acc agc agc ttc cag gaa ggg aca gtg ttt gaa gtc cgg gag aag aac       2817
Thr Ser Ser Phe Gln Glu Gly Thr Val Phe Glu Val Arg Glu Lys Asn
            870                 875                 880 agc agt ggc tgg tgg ttc tgc cag gtc ctg agc gga gcc cct tcc tgg       2865
Ser Ser Gly Trp Trp Phe Cys Gln Val Leu Ser Gly Ala Pro Ser Trp
        885                 890                 895 gaa ggg tgg att cct tcc aac tat ctc aga aag aag ccg tag               2907
Glu Gly Trp Ile Pro Ser Asn Tyr Leu Arg Lys Lys Pro
    900                 905                 910 ccgactccct ttctgcctag agggcccgct ggtccttgct ggctttaccc acgtatttaa    2967
tacgcctctt aatttatcat tctccacgca gcttccaagg cagacagact ctggggtact    3027
gtgacttctt gcctcccatg ggtggagagt gagtttcgga cacctcgggc gcccctgggc    3087
ctgatccctc ctatcacagc atcactggag gctcagaacc cacagccttt gctttctgtc    3147
catgtcagca tccctgcctt aagagaactc ctcctggcca atggcattgc cacccagcag    3207
tgggaccaag actctccaag acctccagga ctggatccca ttgcctggag aaactccagc    3267
aagggtctct catggcttgg acatggcaca gtaagggca gccaacccag tccatgatga     3327
cttttgctcc aacttcttca tgtttctaaa agcccagtgg ctttattcac tcctcctaaa    3387
ttgcctgcta ccagaaggaa cttcatcctg aagaaatgca ttccattacc agttccaggg    3447
aaagtgtccc cttccccaaa gcctcaggcc cgtgggcctc tgaggttcca ctggatgcgg    3507
ctcccccagg agtgggcctg gagatccgct cagccgccct gcctcccacc ttctatcttg    3567
ggaccgtggt cagccctgaa gggtggttcc agccccgcgt atgctgcgct ttgctgctgc    3627
aggctccggt ccctccaggg cttttcaatg agagttccca ccccaacttg gagcatttca    3687
```

```
tttttgccta cctaaagcaa gaatctcaaa gtttgtttga ataagaggcc cattcacaag   3747
tcgtgccctt gtgagcaccc ctttgctgag tgcctcgtgg gtgccaaaca ctgtacttgg   3807
cgctttgcat tcatgctttg accctcacaa cctcccttta tagatgagga aattcacgct   3867
ccatgtgccc aaggacacac cagccaggag gaagagggaa gaggatttga gtccaggcct   3927
gcctgacttc agtgcctgtg ccctcccctc tgtaaaagac aaaccaggca gggaagagat   3987
agaagctggc taagtggtgg ccaagtggct tcattgtgag gggggtgagg gggcattcgt   4047
ggctgctccc acacccacca tccctccagc ccacagcagc ctataccaaa ggctgccctg   4107
gactcaacag ctgcatctcc atgacaggag aatgccaggg tcctggtggt tgacacagag   4167
ccctgttccc tcttctaagc tgttgccccc tggggaatag agcttatgga gcaacgggag   4227
ctgaggtggc ctcgagggcc agcctggagg gctctgagca tagcatgcag cggtcccata   4287
gggaggcagg taaccaaggg ccaggcagag ctgcttcctg tgcctctccg gcatttgtaa   4347 tgttttttc tttttcacg cactgccaaa tctgtttct cccttgaaga aacccagggc   4407
agatgtggtc atctgtcaaa ctgaggtctg gagaggcatg actaaatcac tgcagaagca   4467
aaatcaggac ccagcatttc tagctcccag cccagagtaa gagagcagag cagaaccct   4527 tcccattcta cccgaccgag gcagccctgc cctgccctgc cccgccctc cccaccctgc   4587 cctgccccag agatctccag ttcacagtgt tcatcaggcg agatactttt ggacccacaa   4647
agccagtttt ttgggggat gctcagtgtc tacctgcagt gccaaagtttt tgcttgaaca   4707 gccctcttct gccgcgcctc ccagctccac cccctatcac gtgggtgctg gctgcttctg   4767
cgtgaggagc ttcctctgat cacctgtagc atctttagtg ccttcgtcca gtcggcctgc   4827
aaatcccatt tcccagagag gcttgggcag ggcccacttg ccacttggcc ctgtgcccag   4887
agcgttgggg gcagatggca gccaggggaa gaagggaggg gggaagggc cgccaccgct   4947 tgagggtccc ctcccttgag aggaggcccc atggcagttt tcctgagttc ttgatccact   5007
ttggtttaaa caacttttgt gaagctatgt gagatttgac tgcatttcaa aagacaaaac   5067
acatgttttt ttctgatttg ctcttttgcct ttcagcgacg ctttcagata ctttgtgagt   5127
gtctactctg tgctaggtgc tgagtagact gggatgtgtg tggctccatc cctggctgga   5187
agagctttga gtcctgtctg ctgacttcac tgaaggagtt tctctcttgc ttcattcctt   5247
cctcccgggg gtcagctggg taggagcaga cttgccctgc cttcctctag gcagaaagtt   5307
ttcctgcaaa tgaaagaatc tgccattctc ttttgctatg atgatgatga ttattctgac   5367
atgacccgcg ggtactgaag ccacagtcct ctctgttcac tgttctctcc ttgagtcata   5427
tctatggcct gaggacgtct gtatccagct ccttttccta caatggtaga cacttcccca   5487
ggcagtgggt gggtcagggt ggccagtcac tctcctagct gtccttgcct ggggacttag   5547 atttaccca tccaggactg tggtcgctat tctgtgagcg attgatggcg catatgcaga   5607
actcccctgg agtcatggct ctagaaagtg tccaggccca tcgtgacaat ggtgccaagc   5667
accgggctgg tgaccagtgc ctaaacacac acgctccttt aatccttacg gcaagcctgt   5727
gaggcggata ggaccagccc tgatctatag tgagaaaatt aaggttcaga gggagaaggt   5787
ccaaatagtg gccaagctgg gactgagatc tcgagtttgg gtttgtttgg ttttgttgtt   5847
gttgttcttt ccctcgtgtc catgactttt ctctgccatt agcagggaag tgtgcggagg   5907
gcttccaggg aatcaagtga ccctccctct gaatttcggt gcctcttccc cccgcccctt   5967
gctcacacat ttcagtaggt cacaggccaa atggcagccc aaaaggtggg cagagatttt   6027
tttttcttcc cctcacccct gcttattaac acaattgtga caactacttt accttacatc   6087
```

```
ccagggcaaa cggacagctt gcggtacctc caaaaatttg gaaaaccctg agtctaagac    6147
cacctcttga taaaagaggc ctttgctcac atgttctgct cggaatcttt ctttgccatt    6207
ggtgggtgta tgtcgtccca gctgagactg cgggagagct gagctccagc ttaaaccgct    6267
tttaatggcc cttccctact gggggatcgc tggagcccat gccaggttac ggtagtcatt    6327
ttaaacctct gccacaaggc cacgccatag aatcaatttc caagtcaatg ttcttggccc    6387
taaaatgttt gcgcccactg aggatttcat taccaggtgg aagatggggg aacatatgcc    6447
acgttaaaga gcaagtgctg agtgtgccag gacttgagaa ggaccttagg ctgaggagtg    6507
gacagtctgg tatttatttc gcctctccca agtacccagc acagagtggg aaaaagaaga    6567
aactgctcct gccttccagt agctggcaac ttgacatcaa gaacaaaaac attcgtagct    6627 ggaccccgt cctttcatcg tgcccaagtc ttacatgttg gcttaagctg ccccttgga     6687 ggccgtacct ttctctttgg actgtgacag tggacaccta acagcctgag ccatgtgtgg    6747
ctgtcttatc ccccaagggt tgtccaggcc cgttctgcag ggctgttgtg tagactgcag    6807
acatccatac ctcaccacag accaaagatg acctcgtgtc agactgtggg ctgatgagag    6867
gtagagcagc atgcatcgag gcctgagggt gcagggcgcc ctctcttggc ctggaggaat    6927
tgctcctaac tagagtaagt ttccacgagg gtcccaggca gagctgcaga gctggaaccg    6987
gaggctccac agtccttgcc tgctcatgga cctccttcag agcacctttc tacagactgg    7047 actgccagc tccgtggggt ggcatctggt ttctggtgct attctgccaa gttatcgagc     7107
tcctcctcat gtttcaacat tccatcttcc cgtttctatc ctcgactcca aagtaagcct    7167
tcttagctcc aatcagggat gaggggctca acctcttctg tcctcaaaga ggccaaacgc    7227
agtgccacag tcggtagcct tcactttag atgtcctatt catgtaaaaa agaaggtgcc     7287
cccaccaggc ttacatcagc aataagcaat tctaatgcaa cgatggtgtc cacattttac    7347
cccagtgtgt gcccatgtat gccttgtgc ccgtgtaatt attgttagcg ccccttcac      7407 ttagagggt gatgataaac tgtggccacc ttgattacaa cccacatttc ctgctttggg     7467
gagcttccaa gtaacaggcc atttcttacc tccctccagg aacagtgggc actgcccacc    7527
acctcgtgtc tgctcatagg atgacgctgg agatccccac acttactcta ccctcttggc    7587
aaattggcat tccggtggtg gttttttgttt cctttaacac attaaataaa tgagtatata   7647
ggatgtgagg ggaggggtga gaacaactag ctgtagcatg tgtaggctat atactttacc    7707
atttgacttc tttcctttt tttttttaa ataaaaaaag tgcttgactg gtttcaagct      7767
tcatcatgaa                                                           7777
```

<210> SEQ ID NO 5
<211> LENGTH: 911
<212> TYPE: PRT
<213> ORGANISM: Homo sapiens

<400> SEQUENCE: 5

Met Pro Pro Arg Arg Ser Ile Val Glu Val Lys Val Leu Asp Val Gln
1               5                   10                  15

Lys Arg Arg Val Pro Asn Lys His Tyr Val Tyr Ile Ile Arg Val Thr
            20                  25                  30

Trp Ser Ser Gly Ser Thr Glu Ala Ile Tyr Arg Arg Tyr Ser Lys Phe
        35                  40                  45

Phe Asp Leu Gln Met Gln Met Leu Asp Lys Phe Pro Met Glu Gly Gly
    50                  55                  60

Gln Lys Asp Pro Lys Gln Arg Ile Ile Pro Phe Leu Pro Gly Lys Ile
65                  70                  75                  80

```
Leu Phe Arg Arg Ser His Ile Arg Asp Val Ala Val Lys Arg Leu Ile
                85                  90                  95

Pro Ile Asp Glu Tyr Cys Lys Ala Leu Ile Gln Leu Pro Pro Tyr Ile
            100                 105                 110

Ser Gln Cys Asp Glu Val Leu Gln Phe Phe Glu Thr Arg Pro Glu Asp
            115                 120                 125

Leu Asn Pro Pro Lys Glu Glu His Ile Gly Lys Lys Ser Gly Gly
130                 135                 140

Asp Gln Thr Ser Val Asp Pro Met Val Leu Glu Gln Tyr Val Val
145                 150                 155                 160

Ala Asn Tyr Gln Lys Gln Glu Ser Ser Glu Ile Ser Leu Ser Val Gly
                165                 170                 175

Gln Val Val Asp Ile Ile Glu Lys Asn Glu Ser Gly Trp Trp Phe Val
                180                 185                 190

Ser Thr Ala Glu Glu Gln Gly Trp Val Pro Ala Thr Cys Leu Glu Gly
                195                 200                 205

Gln Asp Gly Val Gln Asp Glu Phe Ser Leu Gln Pro Glu Glu Glu
            210                 215                 220

Lys Tyr Thr Val Ile Tyr Pro Tyr Thr Ala Arg Asp Gln Asp Glu Met
225                 230                 235                 240

Asn Leu Glu Arg Gly Ala Val Val Glu Val Ile Gln Lys Asn Leu Glu
                245                 250                 255

Gly Trp Trp Lys Ile Arg Tyr Gln Gly Lys Glu Gly Trp Ala Pro Ala
                260                 265                 270

Ser Tyr Leu Lys Lys Asn Ser Gly Glu Pro Leu Pro Pro Lys Pro Gly
            275                 280                 285

Pro Gly Ser Pro Ser His Pro Gly Ala Leu Asp Leu Asp Gly Val Ser
            290                 295                 300

Arg Gln Gln Asn Ala Val Gly Arg Glu Lys Glu Leu Leu Ser Ser Gln
305                 310                 315                 320

Arg Asp Gly Arg Phe Glu Gly Arg Pro Val Pro Asp Gly Asp Ala Lys
                325                 330                 335

Gln Arg Ser Pro Lys Met Arg Gln Arg Pro Pro Arg Arg Asp Met
            340                 345                 350

Thr Ile Pro Arg Gly Leu Asn Leu Pro Lys Pro Ile Pro Pro Gln
            355                 360                 365

Val Glu Glu Glu Tyr Tyr Thr Ile Ala Glu Phe Gln Thr Thr Ile Pro
    370                 375                 380

Asp Gly Ile Ser Phe Gln Ala Gly Leu Lys Val Glu Val Ile Glu Lys
385                 390                 395                 400

Asn Leu Ser Gly Trp Trp Tyr Ile Gln Ile Glu Asp Lys Glu Gly Trp
                405                 410                 415

Ala Pro Ala Thr Phe Ile Asp Lys Tyr Lys Lys Thr Ser Asn Ala Ser
            420                 425                 430

Arg Pro Asn Phe Leu Ala Pro Leu Pro His Glu Val Thr Gln Leu Arg
            435                 440                 445

Leu Gly Glu Ala Ala Ala Leu Glu Asn Asn Thr Gly Ser Glu Ala Thr
    450                 455                 460

Gly Pro Ser Arg Pro Leu Pro Asp Ala Pro His Gly Val Met Asp Ser
465                 470                 475                 480

Gly Leu Pro Trp Ser Lys Asp Trp Lys Gly Ser Lys Asp Val Leu Arg
                485                 490                 495

Lys Ala Ser Ser Asp Met Ser Ala Ser Ala Gly Tyr Glu Glu Ile Ser
```

```
                500             505             510
Asp Pro Asp Met Glu Glu Lys Pro Ser Leu Pro Pro Arg Lys Glu Ser
            515                 520                 525
Ile Ile Lys Ser Glu Gly Glu Leu Leu Glu Arg Glu Arg Glu Arg Gln
        530                 535                 540
Arg Thr Glu Gln Leu Arg Gly Pro Thr Pro Lys Pro Pro Gly Val Ile
545                 550                 555                 560
Leu Pro Met Met Pro Ala Lys His Ile Pro Pro Ala Arg Asp Ser Arg
                565                 570                 575
Arg Pro Glu Pro Lys Pro Asp Lys Ser Arg Leu Phe Gln Leu Lys Asn
            580                 585                 590
Asp Met Gly Leu Glu Cys Gly His Lys Val Leu Ala Lys Glu Val Lys
        595                 600                 605
Lys Pro Asn Leu Arg Pro Ile Ser Lys Ser Lys Thr Asp Leu Pro Glu
    610                 615                 620
Glu Lys Pro Asp Ala Thr Pro Gln Asn Pro Phe Leu Lys Ser Arg Pro
625                 630                 635                 640
Gln Val Arg Pro Lys Pro Ala Pro Ser Pro Lys Thr Glu Pro Pro Gln
                645                 650                 655
Gly Glu Asp Gln Val Asp Ile Cys Asn Leu Arg Ser Lys Leu Arg Pro
            660                 665                 670
Ala Lys Ser Gln Asp Lys Ser Leu Leu Asp Gly Glu Gly Pro Gln Ala
        675                 680                 685
Val Gly Gly Gln Asp Val Ala Phe Ser Arg Ser Phe Leu Pro Gly Glu
    690                 695                 700
Gly Pro Gly Arg Ala Gln Asp Arg Thr Gly Lys Gln Asp Gly Leu Ser
705                 710                 715                 720
Pro Lys Glu Ile Ser Cys Arg Ala Pro Pro Arg Pro Ala Lys Thr Thr
                725                 730                 735
Asp Pro Val Ser Lys Ser Val Pro Val Pro Leu Gln Glu Ala Pro Gln
            740                 745                 750
Gln Arg Pro Val Val Pro Pro Arg Arg Pro Pro Pro Lys Lys Thr
        755                 760                 765
Ser Ser Ser Ser Arg Pro Leu Pro Glu Val Arg Gly Pro Gln Cys Glu
770                 775                 780
Gly His Glu Ser Arg Ala Ala Pro Thr Pro Gly Arg Ala Leu Leu Val
785                 790                 795                 800
Pro Pro Lys Ala Lys Pro Phe Leu Ser Asn Ser Leu Gly Gly Gln Asp
                805                 810                 815
Asp Thr Arg Gly Lys Gly Ser Leu Gly Pro Trp Gly Thr Gly Lys Ile
            820                 825                 830
Gly Glu Asn Arg Glu Lys Ala Ala Ala Ala Ser Val Pro Asn Ala Asp
        835                 840                 845
Gly Leu Lys Asp Ser Leu Tyr Val Ala Val Ala Asp Phe Glu Gly Asp
    850                 855                 860
Lys Asp Thr Ser Ser Phe Gln Glu Gly Thr Val Phe Glu Val Arg Glu
865                 870                 875                 880
Lys Asn Ser Ser Gly Trp Trp Phe Cys Gln Val Leu Ser Gly Ala Pro
                885                 890                 895
Ser Trp Glu Gly Trp Ile Pro Ser Asn Tyr Leu Arg Lys Lys Pro
            900                 905                 910

<210> SEQ ID NO 6
<211> LENGTH: 3504
```

```
<212> TYPE: DNA
<213> ORGANISM: Homo sapiens
<220> FEATURE:
<221> NAME/KEY: CDS
<222> LOCATION: (1)..(3378)

<400> SEQUENCE: 6 atg tcg aag acg ctg aag aag aag agg cac tgg ctc agc aag gtg cag         48
Met Ser Lys Thr Leu Lys Lys Lys Arg His Trp Leu Ser Lys Val Gln
1               5                   10                  15 gag tgc gcc gtg tcc tgg gcc ggg ccc ccg gga gac ttc ggc gcg gag         96
Glu Cys Ala Val Ser Trp Ala Gly Pro Pro Gly Asp Phe Gly Ala Glu
                20                  25                  30 atc cgc ggt ggc gcg gag cgt ggc gag ttc ccc tac ctg ggg cgg ctc        144
Ile Arg Gly Gly Ala Glu Arg Gly Glu Phe Pro Tyr Leu Gly Arg Leu
            35                  40                  45 cgc gag gag ccc ggc ggg ggc acc tgc tgc gtc gtc tcg ggc aag gcg        192
Arg Glu Glu Pro Gly Gly Gly Thr Cys Cys Val Val Ser Gly Lys Ala
50                  55                  60 ccc agc cca ggc gat gtg ctg ctg gag gta aac ggg acg cct gtc agc        240
Pro Ser Pro Gly Asp Val Leu Leu Glu Val Asn Gly Thr Pro Val Ser
65                  70                  75                  80 ggg ctc acc aac cgg gac acc ctg gct gtc atc cgc cac ttc cgc gag        288
Gly Leu Thr Asn Arg Asp Thr Leu Ala Val Ile Arg His Phe Arg Glu
                85                  90                  95 ccc atc cgt ctc aag act gtg aaa cca gga aaa gtc att aat aaa gat        336
Pro Ile Arg Leu Lys Thr Val Lys Pro Gly Lys Val Ile Asn Lys Asp
                100                 105                 110 ttg cgg cat tac cta agt ctt cag ttt caa aaa gga tca att gac cac        384
Leu Arg His Tyr Leu Ser Leu Gln Phe Gln Lys Gly Ser Ile Asp His
            115                 120                 125 aaa ctg cag caa gtg atc aga gat aat ctc tac ttg aga acc att cca        432
Lys Leu Gln Gln Val Ile Arg Asp Asn Leu Tyr Leu Arg Thr Ile Pro
130                 135                 140 tgc act aca agg gcc ccc agg gat gga gaa gta cca gga gtg gat tat        480
Cys Thr Thr Arg Ala Pro Arg Asp Gly Glu Val Pro Gly Val Asp Tyr
145                 150                 155                 160 aat ttc att tcc gtt gaa cag ttc aaa gca ctg gaa gag agt gga gca        528
Asn Phe Ile Ser Val Glu Gln Phe Lys Ala Leu Glu Glu Ser Gly Ala
                165                 170                 175 ttg tta gaa agt ggg aca tat gat gga aac ttc tat gga act ccc aag        576
Leu Leu Glu Ser Gly Thr Tyr Asp Gly Asn Phe Tyr Gly Thr Pro Lys
                180                 185                 190 cct cca gca gaa ccc agc cct ttt cag cca gat cca gtt gat caa gtc        624
Pro Pro Ala Glu Pro Ser Pro Phe Gln Pro Asp Pro Val Asp Gln Val
            195                 200                 205 ctc ttt gat aat gag ttt gat gca gaa tct caa aga aaa cga acg aca        672
Leu Phe Asp Asn Glu Phe Asp Ala Glu Ser Gln Arg Lys Arg Thr Thr
210                 215                 220 tct gtc agc aag atg gaa aga atg gat agc tct ctt cct gaa gag gaa        720
Ser Val Ser Lys Met Glu Arg Met Asp Ser Ser Leu Pro Glu Glu Glu
225                 230                 235                 240 gaa gat gag gac aag gaa gct att aat ggc agt gga aac gca gaa aac        768
Glu Asp Glu Asp Lys Glu Ala Ile Asn Gly Ser Gly Asn Ala Glu Asn
                245                 250                 255 gga gag agg cat tct gag tca tct gac tgg atg aag act gtt cca agt        816
Gly Glu Arg His Ser Glu Ser Ser Asp Trp Met Lys Thr Val Pro Ser
                260                 265                 270 tac aac caa aca aat agc tcc atg gac ttt aga aat tat atg atg aga        864
Tyr Asn Gln Thr Asn Ser Ser Met Asp Phe Arg Asn Tyr Met Met Arg
            275                 280                 285
```

```
gat gag act ctg gaa cca ctg ccc aaa aac tgg gaa atg gcc tac act    912
Asp Glu Thr Leu Glu Pro Leu Pro Lys Asn Trp Glu Met Ala Tyr Thr
    290             295             300 gac aca ggg atg atc tac ttc att gac cac aat acc aag aca acc acc    960
Asp Thr Gly Met Ile Tyr Phe Ile Asp His Asn Thr Lys Thr Thr Thr
305             310             315             320 tgg ttg gat cct cgt ctt tgt aag aaa gcc aaa gcc cct gaa gac tgt   1008
Trp Leu Asp Pro Arg Leu Cys Lys Lys Ala Lys Ala Pro Glu Asp Cys
                325             330             335 gaa gat gga gag ctt cct tat ggc tgg gag aaa ata gag gac cct cag   1056
Glu Asp Gly Glu Leu Pro Tyr Gly Trp Glu Lys Ile Glu Asp Pro Gln
            340             345             350 tat ggg aca tac tat gtt gat cac ctt aac cag aaa acc cag ttt gaa   1104
Tyr Gly Thr Tyr Tyr Val Asp His Leu Asn Gln Lys Thr Gln Phe Glu
        355             360             365 aat cca gtg gag gaa gcc aaa agg aaa aag cag tta gga cag gtt gaa   1152
Asn Pro Val Glu Glu Ala Lys Arg Lys Lys Gln Leu Gly Gln Val Glu
    370             375             380 att ggg tct tca aaa cca gat atg gaa aaa tca cac ttc aca aga gat   1200
Ile Gly Ser Ser Lys Pro Asp Met Glu Lys Ser His Phe Thr Arg Asp
385             390             395             400 cca tcc cag ctt aaa ggt gtc ctt gtt cga gca tca ctg aaa aaa agc   1248
Pro Ser Gln Leu Lys Gly Val Leu Val Arg Ala Ser Leu Lys Lys Ser
                405             410             415 aca atg gga ttt ggt ttt act att att ggt gga gat aga cct gat gag   1296
Thr Met Gly Phe Gly Phe Thr Ile Ile Gly Gly Asp Arg Pro Asp Glu
            420             425             430 ttc cta caa gtg aaa aat gtg ctg aaa gat ggt ccc gca gct cag gat   1344
Phe Leu Gln Val Lys Asn Val Leu Lys Asp Gly Pro Ala Ala Gln Asp
        435             440             445 ggg aaa att gca cca ggc gat gtt att gta gac atc aat ggc aac tgt   1392
Gly Lys Ile Ala Pro Gly Asp Val Ile Val Asp Ile Asn Gly Asn Cys
    450             455             460 gtc ctc ggt cac act cat gca gat gtt gtc cag atg ttt caa ttg gta   1440
Val Leu Gly His Thr His Ala Asp Val Val Gln Met Phe Gln Leu Val
465             470             475             480 cct gtc aat cag tat gta aac ctc act tta tgt cgt ggt tat cca ctt   1488
Pro Val Asn Gln Tyr Val Asn Leu Thr Leu Cys Arg Gly Tyr Pro Leu
                485             490             495 cct gat gac agt gaa gat cct gtt gtg gac att gtt gct gcc acc cct   1536
Pro Asp Asp Ser Glu Asp Pro Val Val Asp Ile Val Ala Ala Thr Pro
            500             505             510 gtc atc aat gga cag tca tta acc aag gga gag act tgc atg aat cct   1584
Val Ile Asn Gly Gln Ser Leu Thr Lys Gly Glu Thr Cys Met Asn Pro
        515             520             525 cag gat ttt aag cca gga gca atg gtt ctg gag cag aat gga aaa tcg   1632
Gln Asp Phe Lys Pro Gly Ala Met Val Leu Glu Gln Asn Gly Lys Ser
    530             535             540 gga cac act ttg act ggt gat ggt ctc aat gga cca tca gat gca agt   1680
Gly His Thr Leu Thr Gly Asp Gly Leu Asn Gly Pro Ser Asp Ala Ser
545             550             555             560 gag cag aga gta tcc atg gca tcg tca ggc agc tcc cag cct gaa cta   1728
Glu Gln Arg Val Ser Met Ala Ser Ser Gly Ser Ser Gln Pro Glu Leu
                565             570             575 gtg act atc cct ttg att aag ggc cct aaa ggg ttt ggg ttt gca att   1776
Val Thr Ile Pro Leu Ile Lys Gly Pro Lys Gly Phe Gly Phe Ala Ile
            580             585             590 gct gac agc cct act gga cag aag gtg aaa atg ata ctg gat agt cag   1824
Ala Asp Ser Pro Thr Gly Gln Lys Val Lys Met Ile Leu Asp Ser Gln
        595             600             605
```

```
tgg tgt caa ggc ctt cag aaa gga gat ata att aag gaa ata tac cat    1872
Trp Cys Gln Gly Leu Gln Lys Gly Asp Ile Ile Lys Glu Ile Tyr His
610                 615                 620 caa aat gtg cag aat tta aca cat ctc caa gtg gta gag gtg cta aag    1920
Gln Asn Val Gln Asn Leu Thr His Leu Gln Val Val Glu Val Leu Lys
625                 630                 635                 640 cag ttt cca gta ggt gct gat gta cca ttg ctt atc tta aga gga ggt    1968
Gln Phe Pro Val Gly Ala Asp Val Pro Leu Leu Ile Leu Arg Gly Gly
                645                 650                 655 cct cct tca cca acc aaa act gcc aaa atg aaa aca gat aaa aag gaa    2016
Pro Pro Ser Pro Thr Lys Thr Ala Lys Met Lys Thr Asp Lys Lys Glu
660                 665                 670 aat gca gga agt ttg gag gcc ata aat gag cct att cct cag cct atg    2064
Asn Ala Gly Ser Leu Glu Ala Ile Asn Glu Pro Ile Pro Gln Pro Met
            675                 680                 685 cct ttt cca ccg agc att atc agg tca gga tcc cca aaa ttg gat cct    2112
Pro Phe Pro Pro Ser Ile Ile Arg Ser Gly Ser Pro Lys Leu Asp Pro
690                 695                 700 tct gag gtc tac ctg aaa tct aag act tta tat gaa gat aaa cca cca    2160
Ser Glu Val Tyr Leu Lys Ser Lys Thr Leu Tyr Glu Asp Lys Pro Pro
705                 710                 715                 720 aac acc aaa gat ttg gat gtt ttt ctt cga aaa caa gag tca ggg ttt    2208
Asn Thr Lys Asp Leu Asp Val Phe Leu Arg Lys Gln Glu Ser Gly Phe
                725                 730                 735 ggc ttc agg gtg cta gga gga gat gga cct gac cag tct ata tat att    2256
Gly Phe Arg Val Leu Gly Gly Asp Gly Pro Asp Gln Ser Ile Tyr Ile
                740                 745                 750 ggg gct att att ccc ctg gga gca gct gag aaa gat ggt cgg ctc cgc    2304
Gly Ala Ile Ile Pro Leu Gly Ala Ala Glu Lys Asp Gly Arg Leu Arg
            755                 760                 765 gca gct gat gaa cta atg tgc gtt gat gga att cct gtt aaa ggg aaa    2352
Ala Ala Asp Glu Leu Met Cys Val Asp Gly Ile Pro Val Lys Gly Lys
770                 775                 780 tca cac aaa caa gtc ttg gac ctc atg aca act gct gct cca aat ggc    2400
Ser His Lys Gln Val Leu Asp Leu Met Thr Thr Ala Ala Pro Asn Gly
785                 790                 795                 800 cat gtg tta cta act gtc aga cgg aag atc ttc tat gga gaa aaa caa    2448
His Val Leu Leu Thr Val Arg Arg Lys Ile Phe Tyr Gly Glu Lys Gln
                805                 810                 815 ccc gag gac gac agc tct cag gcc ttc att tca aca cag aat gga tct    2496
Pro Glu Asp Asp Ser Ser Gln Ala Phe Ile Ser Thr Gln Asn Gly Ser
                820                 825                 830 ccc cgc ctg aac cgg gca gag gtc cca gcc agg cct gca ccc cag gag    2544
Pro Arg Leu Asn Arg Ala Glu Val Pro Ala Arg Pro Ala Pro Gln Glu
            835                 840                 845 ccc tat gat gtt gtc ttg caa cga aaa gaa aat gaa gga ttt ggc ttt    2592
Pro Tyr Asp Val Val Leu Gln Arg Lys Glu Asn Glu Gly Phe Gly Phe
850                 855                 860 gtc atc ctc acc tcc aaa aac aaa cca cct cca gga gtt att cct cat    2640
Val Ile Leu Thr Ser Lys Asn Lys Pro Pro Pro Gly Val Ile Pro His
865                 870                 875                 880 aaa att ggc cga gtc ata gaa gga agt ccg gct gac cgc tgt gga aaa    2688
Lys Ile Gly Arg Val Ile Glu Gly Ser Pro Ala Asp Arg Cys Gly Lys
                885                 890                 895 ctg aaa gtt gga gat cat atc tct gca gtg aat ggg cag tcc att gtt    2736
Leu Lys Val Gly Asp His Ile Ser Ala Val Asn Gly Gln Ser Ile Val
                900                 905                 910 gaa ctg tct cat gat aac att gtt cag ctg atc aaa gat gct ggt gtc    2784
Glu Leu Ser His Asp Asn Ile Val Gln Leu Ile Lys Asp Ala Gly Val
            915                 920                 925
```

```
acc gtc aca cta acg gtc att gct gaa gaa gag cat cat ggt cca cca    2832
Thr Val Thr Leu Thr Val Ile Ala Glu Glu Glu His His Gly Pro Pro
    930                 935                 940 tca gga aca aac tca gcc agg caa agc cca gcc ctg cag cac agg ccc    2880
Ser Gly Thr Asn Ser Ala Arg Gln Ser Pro Ala Leu Gln His Arg Pro
945                 950                 955                 960 atg gga cag tca cag gcc aac cac ata cct ggg gac aga agt gcc cta    2928
Met Gly Gln Ser Gln Ala Asn His Ile Pro Gly Asp Arg Ser Ala Leu
                965                 970                 975 gaa ggt gaa att gga aaa gat gtc tcc act tct tac aga cat tct tgg    2976
Glu Gly Glu Ile Gly Lys Asp Val Ser Thr Ser Tyr Arg His Ser Trp
            980                 985                 990 cca gac cac aag cac ctt gca cag  cct gac acc gca gta  att tca gtt  3024
Pro Asp His Lys His Leu Ala Gln  Pro Asp Thr Ala Val  Ile Ser Val
                995              1000                1005 gta ggc agt cgg cac aat cag  aac ctt ggt tgt tat  cca gta gag       3069
Val Gly Ser Arg His Asn Gln  Asn Leu Gly Cys Tyr  Pro Val Glu
    1010                1015                1020 ctg gag aga ggc ccc cgg ggc  ttt gga ttc agc ctc  cga ggg ggg       3114
Leu Glu Arg Gly Pro Arg Gly  Phe Gly Phe Ser Leu  Arg Gly Gly
1025                1030                1035 aag gag tac aac atg ggg ctg  ttc atc ctt cgt ctt  gct gaa gat       3159
Lys Glu Tyr Asn Met Gly Leu  Phe Ile Leu Arg Leu  Ala Glu Asp
    1040                1045                1050 ggt cct gcc atc aaa gat ggc  aga att cat gtt ggt  gac cag att       3204
Gly Pro Ala Ile Lys Asp Gly  Arg Ile His Val Gly  Asp Gln Ile
    1055                1060                1065 gtt gaa atc aat ggg gaa cct  aca caa gga atc aca  cat act cga       3249
Val Glu Ile Asn Gly Glu Pro  Thr Gln Gly Ile Thr  His Thr Arg
1070                1075                1080 gca att gag ctc att cag gct  ggt gga aat aaa gtt  ctt ctt ctt       3294
Ala Ile Glu Leu Ile Gln Ala  Gly Gly Asn Lys Val  Leu Leu Leu
    1085                1090                1095 ttg agg cca gga act ggc ttg  ata cct gac cat ggt  ttg gct cct       3339
Leu Arg Pro Gly Thr Gly Leu  Ile Pro Asp His Gly  Leu Ala Pro
    1100                1105                1110 tcc ggt ctg tgc tcc tac gtg  aaa ccc gag caa cat  taa ggctttcagg    3388
Ser Gly Leu Cys Ser Tyr Val  Lys Pro Glu Gln His
    1115                1120                1125 gcttttcttg gtctttcctt aaaaagactt ggtaaatttg catgtcttgt aaatcacttt   3448
cttcttttgt tttcttttaa attaaaaatg atgctattaa atacatctat ttctat       3504

<210> SEQ ID NO 7
<211> LENGTH: 1125
<212> TYPE: PRT
<213> ORGANISM: Homo sapiens

<400> SEQUENCE: 7

Met Ser Lys Thr Leu Lys Lys Lys Arg His Trp Leu Ser Lys Val Gln
1               5                   10                  15

Glu Cys Ala Val Ser Trp Ala Gly Pro Pro Gly Asp Phe Gly Ala Glu
                20                  25                  30

Ile Arg Gly Gly Ala Glu Arg Gly Glu Phe Pro Tyr Leu Gly Arg Leu
            35                  40                  45

Arg Glu Glu Pro Gly Gly Gly Thr Cys Cys Val Val Ser Gly Lys Ala
        50                  55                  60

Pro Ser Pro Gly Asp Val Leu Leu Glu Val Asn Gly Thr Pro Val Ser
65                  70                  75                  80

Gly Leu Thr Asn Arg Asp Thr Leu Ala Val Ile Arg His Phe Arg Glu
```

```
                    85                  90                  95
Pro Ile Arg Leu Lys Thr Val Lys Pro Gly Lys Val Ile Asn Lys Asp
                100                 105                 110
Leu Arg His Tyr Leu Ser Leu Gln Phe Gln Lys Gly Ser Ile Asp His
                115                 120                 125
Lys Leu Gln Gln Val Ile Arg Asp Asn Leu Tyr Leu Arg Thr Ile Pro
                130                 135                 140
Cys Thr Thr Arg Ala Pro Arg Asp Gly Glu Val Pro Gly Val Asp Tyr
145                 150                 155                 160
Asn Phe Ile Ser Val Glu Gln Phe Lys Ala Leu Glu Glu Ser Gly Ala
                165                 170                 175
Leu Leu Glu Ser Gly Thr Tyr Asp Gly Asn Phe Tyr Gly Thr Pro Lys
                180                 185                 190
Pro Pro Ala Glu Pro Ser Pro Phe Gln Pro Asp Pro Val Asp Gln Val
                195                 200                 205
Leu Phe Asp Asn Glu Phe Asp Ala Glu Ser Gln Arg Lys Arg Thr Thr
                210                 215                 220
Ser Val Ser Lys Met Glu Arg Met Asp Ser Ser Leu Pro Glu Glu Glu
225                 230                 235                 240
Glu Asp Glu Asp Lys Glu Ala Ile Asn Gly Ser Gly Asn Ala Glu Asn
                245                 250                 255
Gly Glu Arg His Ser Glu Ser Ser Asp Trp Met Lys Thr Val Pro Ser
                260                 265                 270
Tyr Asn Gln Thr Asn Ser Ser Met Asp Phe Arg Asn Tyr Met Met Arg
                275                 280                 285
Asp Glu Thr Leu Glu Pro Leu Pro Lys Asn Trp Glu Met Ala Tyr Thr
                290                 295                 300
Asp Thr Gly Met Ile Tyr Phe Ile Asp His Asn Thr Lys Thr Thr Thr
305                 310                 315                 320
Trp Leu Asp Pro Arg Leu Cys Lys Lys Ala Lys Ala Pro Glu Asp Cys
                325                 330                 335
Glu Asp Gly Glu Leu Pro Tyr Gly Trp Glu Lys Ile Glu Asp Pro Gln
                340                 345                 350
Tyr Gly Thr Tyr Tyr Val Asp His Leu Asn Gln Lys Thr Gln Phe Glu
                355                 360                 365
Asn Pro Val Glu Glu Ala Lys Arg Lys Lys Gln Leu Gly Gln Val Glu
                370                 375                 380
Ile Gly Ser Ser Lys Pro Asp Met Glu Lys Ser His Phe Thr Arg Asp
385                 390                 395                 400
Pro Ser Gln Leu Lys Gly Val Leu Val Arg Ala Ser Leu Lys Lys Ser
                405                 410                 415
Thr Met Gly Phe Gly Phe Thr Ile Ile Gly Gly Asp Arg Pro Asp Glu
                420                 425                 430
Phe Leu Gln Val Lys Asn Val Leu Lys Asp Gly Pro Ala Ala Gln Asp
                435                 440                 445
Gly Lys Ile Ala Pro Gly Asp Val Ile Val Asp Ile Asn Gly Asn Cys
                450                 455                 460
Val Leu Gly His Thr His Ala Asp Val Val Gln Met Phe Gln Leu Val
465                 470                 475                 480
Pro Val Asn Gln Tyr Val Asn Leu Thr Leu Cys Arg Gly Tyr Pro Leu
                485                 490                 495
Pro Asp Asp Ser Glu Asp Pro Val Val Asp Ile Val Ala Ala Thr Pro
                500                 505                 510
```

-continued

```
Val Ile Asn Gly Gln Ser Leu Thr Lys Gly Glu Thr Cys Met Asn Pro
            515                 520                 525

Gln Asp Phe Lys Pro Gly Ala Met Val Leu Glu Gln Asn Gly Lys Ser
        530                 535                 540

Gly His Thr Leu Thr Gly Asp Gly Leu Asn Gly Pro Ser Asp Ala Ser
545                 550                 555                 560

Glu Gln Arg Val Ser Met Ala Ser Ser Gly Ser Gln Pro Glu Leu
                565                 570                 575

Val Thr Ile Pro Leu Ile Lys Gly Pro Lys Gly Phe Gly Phe Ala Ile
            580                 585                 590

Ala Asp Ser Pro Thr Gly Gln Lys Val Lys Met Ile Leu Asp Ser Gln
            595                 600                 605

Trp Cys Gln Gly Leu Gln Lys Gly Asp Ile Ile Lys Glu Ile Tyr His
        610                 615                 620

Gln Asn Val Gln Asn Leu Thr His Leu Gln Val Val Glu Val Leu Lys
625                 630                 635                 640

Gln Phe Pro Val Gly Ala Asp Val Pro Leu Leu Ile Leu Arg Gly Gly
                645                 650                 655

Pro Pro Ser Pro Thr Lys Thr Ala Lys Met Lys Thr Asp Lys Lys Glu
            660                 665                 670

Asn Ala Gly Ser Leu Glu Ala Ile Asn Glu Pro Ile Pro Gln Pro Met
            675                 680                 685

Pro Phe Pro Pro Ser Ile Ile Arg Ser Gly Ser Pro Lys Leu Asp Pro
        690                 695                 700

Ser Glu Val Tyr Leu Lys Ser Lys Thr Leu Tyr Glu Asp Lys Pro Pro
705                 710                 715                 720

Asn Thr Lys Asp Leu Asp Val Phe Leu Arg Lys Gln Glu Ser Gly Phe
                725                 730                 735

Gly Phe Arg Val Leu Gly Gly Asp Gly Pro Asp Gln Ser Ile Tyr Ile
            740                 745                 750

Gly Ala Ile Ile Pro Leu Gly Ala Ala Glu Lys Asp Gly Arg Leu Arg
            755                 760                 765

Ala Ala Asp Glu Leu Met Cys Val Asp Gly Ile Pro Val Lys Gly Lys
770                 775                 780

Ser His Lys Gln Val Leu Asp Leu Met Thr Thr Ala Ala Pro Asn Gly
785                 790                 795                 800

His Val Leu Leu Thr Val Arg Arg Lys Ile Phe Tyr Gly Glu Lys Gln
                805                 810                 815

Pro Glu Asp Asp Ser Ser Gln Ala Phe Ile Ser Thr Gln Asn Gly Ser
            820                 825                 830

Pro Arg Leu Asn Arg Ala Glu Val Pro Ala Arg Pro Ala Pro Gln Glu
        835                 840                 845

Pro Tyr Asp Val Val Leu Gln Arg Lys Glu Asn Glu Gly Phe Gly Phe
    850                 855                 860

Val Ile Leu Thr Ser Lys Asn Lys Pro Pro Pro Gly Val Ile Pro His
865                 870                 875                 880

Lys Ile Gly Arg Val Ile Glu Gly Ser Pro Ala Asp Arg Cys Gly Lys
                885                 890                 895

Leu Lys Val Gly Asp His Ile Ser Ala Val Asn Gly Gln Ser Ile Val
            900                 905                 910

Glu Leu Ser His Asp Asn Ile Val Gln Leu Ile Lys Asp Ala Gly Val
        915                 920                 925

Thr Val Thr Leu Thr Val Ile Ala Glu Glu Glu His His Gly Pro Pro
    930                 935                 940
```

```
Ser Gly Thr Asn Ser Ala Arg Gln Ser Pro Ala Leu Gln His Arg Pro
945                 950                 955                 960

Met Gly Gln Ser Gln Ala Asn His Ile Pro Gly Asp Arg Ser Ala Leu
                965                 970                 975

Glu Gly Glu Ile Gly Lys Asp Val Ser Thr Ser Tyr Arg His Ser Trp
            980                 985                 990

Pro Asp His Lys His Leu Ala Gln Pro Asp Thr Ala Val Ile Ser Val
        995                 1000                1005

Val Gly Ser Arg His Asn Gln Asn Leu Gly Cys Tyr Pro Val Glu
    1010                1015                1020

Leu Glu Arg Gly Pro Arg Gly Phe Gly Phe Ser Leu Arg Gly Gly
    1025                1030                1035

Lys Glu Tyr Asn Met Gly Leu Phe Ile Leu Arg Leu Ala Glu Asp
    1040                1045                1050

Gly Pro Ala Ile Lys Asp Gly Arg Ile His Val Gly Asp Gln Ile
    1055                1060                1065

Val Glu Ile Asn Gly Glu Pro Thr Gln Gly Ile Thr His Thr Arg
    1070                1075                1080

Ala Ile Glu Leu Ile Gln Ala Gly Gly Asn Lys Val Leu Leu Leu
    1085                1090                1095

Leu Arg Pro Gly Thr Gly Leu Ile Pro Asp His Gly Leu Ala Pro
    1100                1105                1110

Ser Gly Leu Cys Ser Tyr Val Lys Pro Glu Gln His
    1115                1120                1125

<210> SEQ ID NO 8
<211> LENGTH: 3285
<212> TYPE: DNA
<213> ORGANISM: Homo sapiens
<220> FEATURE:
<221> NAME/KEY: CDS
<222> LOCATION: (147)..(836)

<400> SEQUENCE: 8
taggacagcc ttctcaagaa gattctgcca actcaaaaat attattcttt tttttttttt      60 ttttttgct gttgtttctg agaaactagg tgtcttacca ttttaaaatt tcatatttta     120
tttaaaagga aaccagtgaa ttgaaa atg aga cta aat atc gct atc ttc ttt     173
                             Met Arg Leu Asn Ile Ala Ile Phe Phe
                             1               5 gga gct ctc ttt ggt gct ttg ggg gtg tta ctc ttt ttg gtg gct ttt     221
Gly Ala Leu Phe Gly Ala Leu Gly Val Leu Leu Phe Leu Val Ala Phe
10                  15                  20                  25 gga tcg gat tat tgg ctt ctt gca act gaa gtg ggg aga tgt tca ggt     269
Gly Ser Asp Tyr Trp Leu Leu Ala Thr Glu Val Gly Arg Cys Ser Gly
                30                  35                  40 gaa aag aat ata gag aac gtc act ttt cac cat gaa ggg ttc ttc tgg     317
Glu Lys Asn Ile Glu Asn Val Thr Phe His His Glu Gly Phe Phe Trp
            45                  50                  55 agg tgt tgg ttt aat ggg att gtg gaa gag aat gac tcc aat att tgg     365
Arg Cys Trp Phe Asn Gly Ile Val Glu Glu Asn Asp Ser Asn Ile Trp
        60                  65                  70 aag ttc tgg tac acc aat cag cca ccg tcc aag aac tgc aca cat gct     413
Lys Phe Trp Tyr Thr Asn Gln Pro Pro Ser Lys Asn Cys Thr His Ala
    75                  80                  85 tac ctg tct ccg tac ccc ttc atg aga ggc gag cac aac tcg acc tcc     461
Tyr Leu Ser Pro Tyr Pro Phe Met Arg Gly Glu His Asn Ser Thr Ser
90                  95                  100                 105
```

```
tat gac tct gca gtt att tac cgt ggt ttc tgg gca gtc ctg atg ctc    509
Tyr Asp Ser Ala Val Ile Tyr Arg Gly Phe Trp Ala Val Leu Met Leu
                110                 115                 120 ctg ggg gta gtt gct gta gtc atc gca agc ttt ttg atc atc tgt gca    557
Leu Gly Val Val Ala Val Val Ile Ala Ser Phe Leu Ile Ile Cys Ala
        125                 130                 135 gcc ccc ttc gcc agc cat ttt ctc tac aaa gct ggg gga ggc tca tat    605
Ala Pro Phe Ala Ser His Phe Leu Tyr Lys Ala Gly Gly Gly Ser Tyr
        140                 145                 150 att gct gca ggc atc cta ttt tca ttg gtg gtg atg ctg tat gtc atc    653
Ile Ala Ala Gly Ile Leu Phe Ser Leu Val Val Met Leu Tyr Val Ile
    155                 160                 165 tgg gtc cag gca gtg gct gac atg gaa agc tac cga aac atg aaa atg    701
Trp Val Gln Ala Val Ala Asp Met Glu Ser Tyr Arg Asn Met Lys Met
170                 175                 180                 185 aag gac tgc ctg gat ttc acc cct tct gtt ctg tat ggc tgg tca ttt    749
Lys Asp Cys Leu Asp Phe Thr Pro Ser Val Leu Tyr Gly Trp Ser Phe
                190                 195                 200 ttc ctg gcc cca gct ggg ata ttt ttt tct ttg cta gct gga tta cta    797
Phe Leu Ala Pro Ala Gly Ile Phe Phe Ser Leu Leu Ala Gly Leu Leu
                205                 210                 215 ttt ctg gtt gtt gga cgg cat att cag ata cat cac taa atcaactgtt    846
Phe Leu Val Val Gly Arg His Ile Gln Ile His His
                220                 225 gtcacaagta ttttcttgag agattttaaa acaaggaata cttttttttcc attttgtttc    906 attgatccca gcataaagtt agtagatata acttttttagt tgctattcaa attaatcatt    966
ttactaaaat tttcttcagt aagaaggtcc tagaatctct ccagacacca gcaagcctct    1026
atcttgtcta agtgctgtca aggacctagt tctttaggga ataggtaaac aggtctccct    1086
ttcattgaac atgttagagt tcatgcaggt cgcaaaggcc tgataatagc ttaataccat    1146
gacatgggga aaatctcgat agatttggct taaagtctcc ttggcattca cttctgctaa    1206
ttaaaaaaaa tccttgaaga ataattaaga atgggcaagg ttgtcagaga atttattttg    1266
tttcttgccc acacagataa tatccacata cacattcact ggctcttgtg agcaaatgaa    1326
tttaaaaata gacagcagtt gttctaatta gtgggagcca tgtactcacc agttaaaatg    1386
ggccacaaca aacaagactg agagcatgta cttatcttgc tttttcacca acagtggttt    1446
ggttacctag ttttattcac ttaattgtgc atgcttacat aaactttaaa ctacatttaa    1506
aactagcaaa tctgcatacc aaattatgta taacgtagat tgaattttta tgaacttaaa    1566
gtgagttaat tgtataatgt aatattgttt aaaaatgta aaaaccaagc atttccgctt    1626
ggtccataat tctatttgat attttaaaat tctcatttaa aaattatatt gctatcattc    1686
agcatgtgaa aatttattga taaaatgtga ttttaatatt ctttagatat aaactttcag    1746
cgtacttcca tatgaggatt ataatagccc tgctttatta aagaccataa aatattaact    1806
ttccccaaga tgttatgggt tccagttctt ctgatcattt gattccttta attactgtcc    1866
ctcaatttct tcatctttac aatagatata ttaacattta cagatcgact atttccttta    1926
acctcctaga agaagttttt tgtggggaaa gatgattctg tattattcag tagcatagac    1986
attttgcata tcaaagatgt tcatttggca ctaatgttga ttgaaatcaa atccatctga    2046
gatgcctagc tcgtatttgc attctggaag cctccatcgc aggggagctc ggcagggtat    2106
gtgagctttg ttggaggtgc ggtgtttcat tctgcagctg ttgtgaggac agagaggcat    2166
ggccacaggg caaaaaaagt caccacccag aagatgctct gggatagagg aactgctcct    2226
tttcatcagc tcttccaatg ccgtgggaga ggtgatccca gtcttctctg tacatcttgt    2286
```

```
gcttttccat taagacttgt tccagtggga aggagctttg gaaaaattgc aaaggtctga    2346
atcttcaggg cattttcatg acaggacttg ccaataataa taataataat aataataata    2406
ataataataa taataaagct ccagaggcct aactggtttc tcaagtcatt tcagtgatat    2466
cattgaaacg tttttgtggt acttcccttt gtctttcact gtttcatttt tatattgctt    2526
catttacttc tttgcttttg gctttgttat tagaaaaaat aattatgagg tctgttgtgc    2586
atgttgactg tgatattaag ttatggcatg ccattaagtt ttccagacga tgttggatgt    2646
atctgattag ttcatgtcat ctgtaaatac aattcttttt tgtagtactt ggaatggag    2706 ccttttttctg gtgtactgta tgccatttaa gtttcacata caagctgctt tcggcaaagg    2766
ctcgaatatt tataaatttc agatggttat cctcacttta tagtacactt aagtggctac    2826
catatatttt ttatatgaca attggctgaa tagctgatgt gtatgacact tttacacaga    2886
tttgcacttt ggaactattt tatagttgta atgcatcaat caaatacatt tcaagcacat    2946
ttcttgatca atttaccagc aaccctctga aggaatgaag gagagttgtg attgctatgt    3006
caatgagtga aatatactta aaaatggcag agatatatag tacattattg tagcaacctt    3066
atatctgatt tgagatactg tgttgccaaa tgtccatgtt atgtttattt ctctattggt    3126
tgtatttatt aattttttaga agcctttaaa ctgtgttaga atctttttga aaaatgttga    3186
ttttgcatca taaagtttca atttatcaag gatatctttt cagttacact tttagaaaga    3246
gtgaataaaa agggcagtga gttatgctct tggacttgg                            3285

<210> SEQ ID NO 9
<211> LENGTH: 229
<212> TYPE: PRT
<213> ORGANISM: Homo sapiens

<400> SEQUENCE: 9

Met Arg Leu Asn Ile Ala Ile Phe Phe Gly Ala Leu Phe Gly Ala Leu
1               5                   10                  15

Gly Val Leu Leu Phe Leu Val Ala Phe Gly Ser Asp Tyr Trp Leu Leu
            20                  25                  30

Ala Thr Glu Val Gly Arg Cys Ser Gly Glu Lys Asn Ile Glu Asn Val
        35                  40                  45

Thr Phe His His Glu Gly Phe Phe Trp Arg Cys Trp Phe Asn Gly Ile
    50                  55                  60

Val Glu Glu Asn Asp Ser Asn Ile Trp Lys Phe Trp Tyr Thr Asn Gln
65                  70                  75                  80

Pro Pro Ser Lys Asn Cys Thr His Ala Tyr Leu Ser Pro Tyr Pro Phe
                85                  90                  95

Met Arg Gly Glu His Asn Ser Thr Ser Tyr Asp Ser Ala Val Ile Tyr
            100                 105                 110

Arg Gly Phe Trp Ala Val Leu Met Leu Leu Gly Val Ala Val Val
        115                 120                 125

Ile Ala Ser Phe Leu Ile Ile Cys Ala Ala Pro Phe Ala Ser His Phe
    130                 135                 140

Leu Tyr Lys Ala Gly Gly Gly Ser Tyr Ile Ala Ala Gly Ile Leu Phe
145                 150                 155                 160

Ser Leu Val Val Met Leu Tyr Val Ile Trp Val Gln Ala Val Ala Asp
                165                 170                 175

Met Glu Ser Tyr Arg Asn Met Lys Met Lys Asp Cys Leu Asp Phe Thr
            180                 185                 190

Pro Ser Val Leu Tyr Gly Trp Ser Phe Phe Leu Ala Pro Ala Gly Ile
        195                 200                 205
```

Phe Phe Ser Leu Leu Ala Gly Leu Leu Phe Leu Val Val Gly Arg His
    210                 215                 220

Ile Gln Ile His His
225

<210> SEQ ID NO 10
<211> LENGTH: 25
<212> TYPE: RNA
<213> ORGANISM: Artificial
<220> FEATURE:
<223> OTHER INFORMATION: siRNA oligo sequence

<400> SEQUENCE: 10
ugaauucgag cucgguaccc gggga                                             25

<210> SEQ ID NO 11
<211> LENGTH: 24
<212> TYPE: RNA
<213> ORGANISM: Artificial
<220> FEATURE:
<223> OTHER INFORMATION: siRNA oligo

<400> SEQUENCE: 11
caggaaagaa caugugagca aaag                                              24

<210> SEQ ID NO 12
<211> LENGTH: 25
<212> TYPE: RNA
<213> ORGANISM: Artificial
<220> FEATURE:
<223> OTHER INFORMATION: siRNA oligo

<400> SEQUENCE: 12
cuuuuaaauu aaaaaugaag uuuua                                             25

<210> SEQ ID NO 13
<211> LENGTH: 5521
<212> TYPE: DNA
<213> ORGANISM: Artificial
<220> FEATURE:
<223> OTHER INFORMATION: pCDNA3 cloning vector with mutation, deletion
      and insertions

<400> SEQUENCE: 13
gacggatcgg gagatctccc gatcccctat ggtcgactct cagtacaatc tgctctgatg       60
ccgcatagtt aagccagtat ctgctccctg cttgtgtgtt ggaggtcgct gagtagtgcg      120
cgagcaaaat ttaagctaca caaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggac tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780

-continued

```
gtaggcgtgt acggtgggag gtctatataa gcagagctct ctggctaact agagaaccca      840
ctgcttactg gcttatcgaa attaatacga ctcactatag ggagacccaa gcttctcgag      900
gccgccacca tgggatccac catgtacgac gttcctgatt acgctagcct cccgagatat      960
ccggaattcg gtaccgagct cggatccact agtaacggcc gccagtgtgc tggaattctg     1020
cagatatcca tcacactggc ggccgctcga gcatgcatct agagggccct attctatagt     1080
gtcacctaaa tgctagagct cgctgatcag cctcgactgt gccttctagt tgccagccat     1140
ctgttgtttg cccctccccc gtgccttcct gaccctggaa ggtgccact cccactgtcc      1200 tttcctaata aaatgaggaa attgcatcgc attgtctgag taggtgtcat tctattctgg     1260
ggggtggggt ggggcaggac agcaaggggg aggattggga agacaatagc aggcatgctg     1320
gggatgcggt gggctctatg gcttctgagg cggaaagaac cagctgggc tctagggggt      1380 atccccacgc gccctgtagc ggcgcattaa gcgcggcggg tgtggtggtt acgcgcagcg     1440
tgaccgctac acttgccagc gccctagcgc ccgctccttt cgctttcttc ccttcctttc     1500
tcgccacgtt cgccggcttt ccccgtcaag ctctaaatcg gggcatccct ttagggttcc     1560
gatttagtgc tttacggcac ctcgacccca aaaaacttga ttagggtgat ggttcacgta     1620
gtgggccatc gccctgatag acggtttttc gccctttgac gttggagtcc acgttcttta     1680
atagtggact cttgttccaa actggaacaa cactcaaccc tatctcggtc tattcttttg     1740
atttataagg gattttgggg atttcggcct attggttaaa aaatgagctg atttaacaaa     1800
aatttaacgc gaattaattc tgtggaatgt gtgtcagtta gggtgtggaa agtccccagg     1860
ctccccaggc aggcagaagt atgcaaagca tgcatctcaa ttagtcagca accaggtgtg     1920
gaaagtcccc aggctcccca gcaggcagaa gtatgcaaag catgcatctc aattagtcag     1980
caaccatagt cccgccccta actccgccca tcccgcccct aactccgccc agttccgccc     2040
attctccgcc ccatggctga ctaatttttt tatttatgc agaggccgag gccgcctctg      2100
cctctgagct attccagaag tagtgaggag cttttttgg aggcctaggc ttttgcaaaa      2160
agctcccggg agcttgtata tccatttcg gatctgatca agagacagga tgaggatcgt      2220
ttcgcatgat tgaacaagat ggattgcacg caggttctcc ggccgcttgg gtggagaggc     2280
tattcggcta tgactgggca caacagacaa tcggctgctc tgatgccgcc gtgttccggc     2340
tgtcagcgca ggggcgcccg gttcttttg tcaagaccga cctgtccggt gccctgaatg      2400
aactgcagga cgaggcagcg cggctatcgt ggctggccac gacgggcgtt ccttgcgcag     2460
ctgtgctcga cgttgtcact gaagcggaa gggactggct gctattgggc gaagtgccgg     2520 gcaggatct cctgtcatct caccttgctc ctgccgagaa agtatccatc atggctgatg      2580
caatgcggcg gctgcatacg cttgatccgg ctacctgccc attcgaccac caagcgaaac     2640
atcgcatcga gcgagcacgt actcggatgg aagccggtct tgtcgatcag gatgatctgg     2700
acgaagagca tcaggggctc gcgccagccg aactgttcgc caggctcaag gcgcgcatgc     2760
ccgacggcga ggatctcgtc gtgacccatg gcgatgcctg cttgccgaat atcatggtgg     2820
aaaatggccg cttttctgga ttcatcgact gtggccggct gggtgtggcg gaccgctatc     2880
aggacatagc gttggctacc cgtgatattg ctgaagagct tggcggcgaa tgggctgacc     2940
gcttcctcgt gctttacggt atcgccgctc ccgattcgca gcgcatcgcc ttctatcgcc     3000
ttcttgacga gttcttctga gcgggactct ggggttcgaa atgaccgacc aagcgacgcc     3060
caacctgcca tcacgagatt tcgattccac cgccgccttc tatgaaaggt tgggcttcgg     3120
aatcgttttc cgggacgccg gctggatgat cctccagcgc ggggatctca tgctggagtt     3180
```

```
cttcgcccac cccaacttgt ttattgcagc ttataatggt tacaaataaa gcaatagcat    3240
cacaaatttc acaaataaag catttttttc actgcattct agttgtggtt tgtccaaact    3300
catcaatgta tcttatcatg tctgtatacc gtcgacctct agctagagct tggcgtaatc    3360
atggtcatag ctgtttcctg tgtgaaattg ttatccgctc acaattccac acaacatacg    3420
agccggaagc ataaagtgta aagcctgggg tgcctaatga gtgagctaac tcacattaat    3480
tgcgttgcgc tcactgcccg ctttccagtc gggaaacctg tcgtgccagc tgcattaatg    3540
aatcggccaa cgcgcgggga gaggcggttt gcgtattggg cgctcttccg cttcctcgct    3600
cactgactcg ctgcgctcgg tcgttcggct gcggcgagcg gtatcagctc actcaaaggc    3660
ggtaatacgg ttatccacag aatcagggga taacgcagga agaacatgt gagcaaaagg    3720 ccagcaaaag gccaggaacc gtaaaaaggc cgcgttgctg gcgttttcc ataggctccg    3780 cccccctgac gagcatcaca aaatcgacg ctcaagtcag aggtggcgaa acccgacagg    3840
actataaaga taccaggcgt ttccccctgg aagctccctc gtgcgctctc ctgttccgac    3900
cctgccgctt accggatacc tgtccgcctt tctcccttcg ggaagcgtgg cgctttctca    3960
atgctcacgc tgtaggtatc tcagttcggt gtaggtcgtt cgctccaagc tgggctgtgt    4020
gcacgaaccc cccgttcagc ccgaccgctg cgccttatcc ggtaactatc gtcttgagtc    4080
caacccggta agacacgact tatcgccact ggcagcagcc actggtaaca ggattagcag    4140
agcgaggtat gtaggcggtg ctacagagtt cttgaagtgg tggcctaact acggctacac    4200
tagaaggaca gtatttggta tctgcgctct gctgaagcca gttaccttcg aaaaagagt    4260 tggtagctct tgatccggca aacaaaccac cgctggtagc ggtggttttt ttgtttgcaa    4320
gcagcagatt acgcgcagaa aaaaaggatc tcaagaagat cctttgatct tttctacggg    4380
gtctgacgct cagtggaacg aaaactcacg ttaagggatt ttggtcatga gattatcaaa    4440
aaggatcttc acctagatcc ttttaaatta aaaatgaagt tttaaatcaa tctaaagtat    4500
atatgagtaa acttggtctg acagttacca atgcttaatc agtgaggcac ctatctcagc    4560
gatctgtcta tttcgttcat ccatagttgc ctgactcccc gtcgtgtaga taactacgat    4620
acgggagggc ttaccatctg gccccagtgc tgcaatgata ccgcgagacc cacgctcacc    4680
ggctccagat ttatcagcaa taaaccagcc agccggaagg gccgagcgca gaagtggtcc    4740
tgcaacttta tccgcctcca tccagtctat taattgttgc cgggaagcta gagtaagtag    4800
ttcgccagtt aatagtttgc gcaacgttgt tgccattgct acaggcatcg tggtgtcacg    4860
ctcgtcgttt ggtatggctt cattcagctc cggttcccaa cgatcaaggc gagttacatg    4920
atcccccatg ttgtgcaaaa aagcggttag ctccttcggt cctccgatcg ttgtcagaag    4980
taagttggcc gcagtgttat cactcatggt tatggcagca ctgcataatt ctcttactgt    5040
catgccatcc gtaagatgct tttctgtgac tggtgagtac tcaaccaagt cattctgaga    5100
atagtgtatg cggcgaccga gttgctcttg cccggcgtca atacgggata ataccgcgcc    5160
acatagcaga actttaaaag tgctcatcat tggaaaacgt tcttcggggc gaaaactctc    5220
aaggatctta ccgctgttga gatccagttc gatgtaaccc actcgtgcac ccaactgatc    5280
ttcagcatct tttactttca ccagcgtttc tgggtgagca aaaacaggaa ggcaaaatgc    5340
cgcaaaaaag ggaataaggg cgacacgaa atgttaata tcatactct tccttttca    5400 atattattga agcatttatc agggttattg tctcatgagc ggatacatat ttgaatgtat    5460
ttagaaaaat aaacaaatag gggttccgcg cacatttccc cgaaaagtgc cacctgacgt    5520
c                                                                    5521
```